US008815562B2

(12) United States Patent
Sherman et al.

(10) Patent No.: US 8,815,562 B2
(45) Date of Patent: Aug. 26, 2014

(54) BIOSYNTHETIC PATHWAY FOR HETEROLOGOUS EXPRESSION OF A NONRIBOSOMAL PEPTIDE SYNTHETASE DRUG AND ANALOGS

(75) Inventors: David H. Sherman, Ann Arbor, MI (US); Garth D. Ehrlich, Pittsburgh, PA (US); Benjamin Janto, Pittsburgh, PA (US); Robert M. Williams, Fort Collins, CO (US); Christopher M. Rath, San Diego, CA (US)

(73) Assignees: The Regenys of the University of Michigan, Ann Arbor, MI (US); Allegheny-Singer Research Institute, Pittsburgh, PA (US); Colorado State University Research Foundation, Fort Collins, CO (US)

( * ) Notice: Subject to any disclaimer, the term of this patent is extended or adjusted under 35 U.S.C. 154(b) by 12 days.

(21) Appl. No.: 13/640,815

(22) PCT Filed: Apr. 15, 2011

(86) PCT No.: PCT/US2011/032796
§ 371 (c)(1),
(2), (4) Date: Dec. 26, 2012

(87) PCT Pub. No.: WO2011/130719
PCT Pub. Date: Oct. 20, 2011

(65) Prior Publication Data

US 2013/0095533 A1 Apr. 18, 2013

Related U.S. Application Data

(60) Provisional application No. 61/324,639, filed on Apr. 15, 2010.

(51) Int. Cl.

| | |
|---|---|
| ***C12N 9/88*** | (2006.01) |
| ***C12N 15/00*** | (2006.01) |
| ***C12N 1/20*** | (2006.01) |
| ***C07K 1/00*** | (2006.01) |
| ***C07H 21/04*** | (2006.01) |
| ***C12P 17/18*** | (2006.01) |
| ***C12N 15/52*** | (2006.01) |

(52) U.S. Cl.
CPC ............. *C12P 17/188* (2013.01); *C12P 17/182* (2013.01); *C12N 15/52* (2013.01)
USPC ..................... 435/232; 435/320.1; 435/252.3; 530/350; 536/23.2

(58) Field of Classification Search
USPC .................... 435/232, 320.1, 252.3; 530/350; 536/23.2
See application file for complete search history.

(56) References Cited

U.S. PATENT DOCUMENTS

| | | | |
|---|---|---|---|
| 5,089,273 | A | 2/1992 | Rinehart et al. |
| 7,309,601 | B2 | 12/2007 | Perez Esteban et al. |
| 7,442,720 | B2 | 10/2008 | Chan et al. |
| 7,973,073 | B2 | 7/2011 | Mylari et al. |
| 2006/0089389 | A1 | 4/2006 | Allison et al. |
| 2007/0293562 | A1 | 12/2007 | Mylari et al. |
| 2008/0221210 | A1 | 9/2008 | Garcia Collazo et al. |
| 2009/0048154 | A1 | 2/2009 | Chan et al. |
| 2010/0227797 | A1 | 9/2010 | Axelson et al. |
| 2011/0052678 | A1 | 3/2011 | Shantha et al. |

FOREIGN PATENT DOCUMENTS

WO WO-2004/015143 2/2004

OTHER PUBLICATIONS

Arai et al., The structure of a novel antitumor antibiotic, saframycin A,Cell. Mol. Life. Sci., 36:1025-7 (1980).
Arroyo et al., Biotechnological applications of penicillin acylases: state-of-the-art, Appl. Microbiol. Biotechnol., 60(5):507-14 (2003).
Bachmann et al., Chapter 8. Methods for in silico prediction of microbial polyketide and nonribosomal peptide biosynthetic pathways from DNA sequence data, Methods Enzymol., 458:181-217 (2007).
Bocs et al., AMIGene: Annotation of Microbial Genes, Nucleic Acids Res., 31(13):3723-6 (2003).
Brady et al., Metagenomic approaches to natural products from free-living and symbiotic organisms, Nat. Prod. Rep., 26(11):1488-503 (2009).
Brown et al., The MerR family of transcriptional regulators, FEMS Microbiol. Rev., 27(2-3):145-63 (2003).
Cane et al., Harnessing the biosynthetic code: combinations, permutations, and mutations, Science, 282(5386):63-8 (1998).
Carballo, Production of *Ecteinascidia turbinata* (Ascidiacea: Perophoridae) for obtaining anticancer compounds, J. World Aquaculture Soc., 31:481-90 (2000).
Chen et al., Total synthesis of Ecteinascidin 743, J. Am. Chem. Soc., 128:87-9 (2005).
Chuk et al., Trabectedin, Oncologist, 14(8):794-9 (2009).
Corey et al., Enantioselective total synthesis of Ecteinascidin, J. Am. Chem. Soc., 118:9202-3 (1996).
Cuevas et al., Development of Yondelis® (trabectedin, ET-743). A semisynthetic process solves the supply problem, Nat. Prod. Rep. 26:322-37 (2009).
Cuevas et al., Synthesis of ecteinascidin ET-743 and phthalascidin Pt-650 from cyanosafracin B, Org. Lett., 2(16):2545-8 (2000).
D'Agostino et al., A multicenter phase II study of the cryptophycin analog LY355703 in patients with platinum-resistant ovarian cancer, Int. J. Gynecol. Cancer, 16(1):71-6 (2006).
D'Incalci et al., Unique features of the mode of action of ET-743, Oncologist, 7(3):210-6 (2002).
DeSantis et al., Greengenes, a chimera-checked 16S rRNA gene database and workbench compatible with ARB, Appl. Environ. Microbiol., 72(7):5069-72 (2006).

(Continued)

*Primary Examiner* — Maryam Monshipouri
(74) *Attorney, Agent, or Firm* — Marshall, Gerstein & Borun LLP

(57) ABSTRACT

The present invention is directed to the biosynthetic pathway for a nonribosomal peptide synthetase (NRPS) derived drug and analogs thereof. The invention also discloses polynucleotide sequences useful for heterologous expression in a convenient microbial host for the synthesis of the NRPS derived drug.

18 Claims, 4 Drawing Sheets

(56) References Cited

OTHER PUBLICATIONS

DeSantis et al., NAST: a multiple sequence alignment server for comparative analysis of 16S rRNA genes, Nucleic Acids Res., 34 (Web Server Issue): W394-9 (2006).
Endo et al., Total synthesis of ecteinascidin 743, J. Am. Chem. Soc., 124:6552-4 (2002).
Fischbach et al., Assembly-line enzymology for polyketide and nonribosomal Peptide antibiotics: logic, machinery, and mechanisms, Chem. Rev., 106(8):3468-96 (2006).
Fishlock et al., Synthetic Studies on Et-743. Assembly of the Pentacyclic Core and a Formal Total Synthesis, 73(24):9594-600 (2008).
Fu et al., Biosynthesis of 3-hydroxy-5-methyl-o-methyltyrosine in the saframycin/ safracin biosynthetic pathway, J. Microbiol. Biotechnol., 19(5):439-46 (2009).
GenBank Accession No. AY061859, *Pseudomonas fluorescens* safracin biosynthesis gene cluster, complete sequence (May 11, 2005).
GenBank Accession No. DQ838002.1, *Streptomyces lavendulae* strain NRRL 11002 tyrosinase, tyrosinase co-factor, putative translation initiation inhibitor, putative transcriptional regulator, hypothetical protein, putative methyltransferase, hypothetical protein, and glyoxalase/bleomycin resistance protein/dioxygenase genes, complete cds; and saframycin A biosynthetic gene cluster, complete sequence (Jan. 2, 2008).
GenBank Accession No. HQ609499, Uncultured organism clone ET_Etu_NRPS ET-743 non-ribosomal peptide synthase biosynthetic gene cluster, partial sequence (Mar. 14, 2012).
GenBank Accession No. MXU24657, *Myxococcus xanthus* saframycin Mx1 synthetase B (safB), saframycin Mx1 synthetase A (safA), and safC genes, complete cds, Jun. 19, 1996.
Guindon et al., A simple, fast, and accurate algorithm to estimate large phylogenies by maximum likelihood, Syst. Biol., 52(5):696-704 (2003).
Hahn et al., Selective interaction between nonribosomal peptide synthetases is facilitated by short communication-mediating domains, Proc. Natl. Acad. Sci. USA, 101 (44):15585-90 (2004).
Hicks et al., Structural characterization of in vitro and in vivo intermediates on the loading module of microcystin synthetase, ACS Chem. Biol., 1(2):93-102 (2006).
Ikeda et al., Safracins, new antitumor antibiotics. III. Biological activity, J. Antibiot (Tokyo): 36(10):1290-4 (1983).
International Preliminary Report on Patentability for corresponding international application No. PCT/US2011/032796, issuance date Oct. 16, 2012.
International Search Report and Written Opinion for corresponding international application No. PCT/US2011/032796, mailing date Dec. 7, 2011.
Irschik et al., Saframycin Mx1, a new natural saframycin isolated from a myxobacterium, J. Antibiot (Tokyo), 41(8):993-8 (1988).
Izbicka et al., In vitro antitumor activity of the novel marine agent, ecteinascidin-743 (ET-743, NSC-648766) against human tumors explanted from patients, Ann. Oncol., 9(9):981-7 (1998).
Jack et al., The drug/metabolite transporter superfamily, Eur. J. Biochem., 268(13):3620-39 (2001).
Keane et al., Assessment of methods for amino acid matrix selection and their use on empirical data shows that ad hoc assumptions for choice of matrix are not justified, BMC Evol. Biol., 6:29 (2006).
Kerr et al., Biosynthetic studies of ecteinascidins in the marine tunicate *Ecteinascidia turbinata*, J. Nat. Prod., 58(10):1618-21 (1995).
Kittendorf et al., Interrogating the molecular basis for multiple macrolactone ring formation by the pikromycin polyketide synthase, Chem. Biol., 14(8):944-54 (2007).
Koketsu et al., Reconstruction of the saframycin core scaffold defines dual Pictet-Spengler mechanisms, Nat. Chem. Biol., 6:408-10 (2010).
Kopp et al., Peptide macrocyclization: the reductase of the nostocyclopeptide synthetase triggers the self-assembly of a macrocyclic imine, J. Am. Chem. Soc., 128(51):16478-9 (2006).
Li et al., Characterization of the saframycin A gene cluster from *Streptomyces lavendulae* NRRL 11002 revealing a nonribosomal peptide synthetase system for assembling the unusual tetrapeptidyl skeleton in an iterative manner, J. Bacteriol., 190(1):251-63 (2008).
Lopanik et al., In vivo and in vitro trans-acylation by BryP, the putative bryostatin pathway acyltransferase derived from an uncultured marine symbiont, Chem. Biol., 15(11):1175-86 (2008).
Lopanik et al., Potent cytotoxins produced by a microbial symbiont protect host larvae from predation, Oecologia, 139(1):131-9 (2004).
Magarvey et al., Biosynthetic characterization and chemoenzymatic assembly of the cryptophycins. Potent anticancer agents from cyanobionts, ACS Chem. Biol., 1(12):766-79 (2006).
Marahiel et al., Modular peptide synthetases involved in nonribosomal peptide synthesis, Chem. Rev., 97(7):2651-4 (1997).
Mendola, "Aquacultural production of bryostatin I and ecteinascidin 743", pp. 120-133 In: Fusetani (ed.), Drugs from the Sea, Basel: Karger (2000).
Meyer et al., The metagenomics RAST server—a public resource for the automatic phylogenetic and functional analysis of metagenomes, BMC Bioinformatics, 9:386 (2008).
Minuzzo et al., Interference of transcriptional activation by the antineoplastic drug ecteinascidin-743, Proc. Natl. Acad. Sci. USA, 97(12):6780-4 (2000).
Mootz et al., Biosynthetic systems for nonribosomal peptide antibiotic assembly, Curr. Opin. Chem. Biol., 1(4):543-51 (1997).
Moss et al., Intracellular bacteria associated with the ascidian *Ecteinascidia turbinata*: phylogenetic and in situ hybridisation analysis, Marine Biology, 143:99-110 (2003).
Nelson et al., Characterization of SafC, a catechol 4-O-methyltransferase involved in saframycin biosynthesis, Appl. Environ. Microbiol., 73(11):3575-80 (2007).
Nguyen et al., Combinatorial biosynthesis of novel antibiotics related to daptomycin, Proc. Natl. Acad. Sci. USA, 103(46):17462-7 (2006).
Pak et al., A symbiont-produced protein and bacterial symbiosis in *Amoeba proteus*, J. Eukaryotic Microbiol., 44(6):614-9 (1997).
Pak et al., The s29x gene of symbiotic bacteria in *Amoeba proteus* with a novel promote, Gene, 171 (1):89-93 (1996).
Partida-Martinez et al., *Burkholderia rhizoxinica* sp. nov. and *Burkholderia endofungorum* sp. nov., bacterial endosymbionts of the plant-pathogenic fungus *Rhizopus microsporus*, Int. J. Syst. Evol. Microbiol., 57(Pt.11):2583-90 (2007).
Partida-Martinez et al., Pathogenic fungus harbours endosymbiotic bacteria for toxin production, Nature, 437(7060):884-8 (2005).
Perez-Matos et al., Bacterial diversity associated with the Caribbean tunicate *Ecteinascidia turbinata*, Antonie Van Leeuwenhoek, 92(2):155-64 (2007).
Piel et al., Antitumor polyketide biosynthesis by an uncultivated bacterial symbiont of the marine sponge *Theonella swinhoei*, Proc. Natl. Acad. Sci. USA, 101(46):16222-7 (2004).
Piel, A polyketide synthase-peptide synthetase gene cluster from an uncultured bacterial symbiont of Paederus beetles, Proc. Natl. Acad. Sci. USA, 99(22):14002-7 (2002).
Piel, Bacterial symbionts: prospects for the sustainable production of invertebrate-derived pharmaceuticals, Curr. Med. Chem., 13(1):39-50 (2006).
Pommier et al., DNA sequence- and structure-selective alkylation of guanine N2 in the DNA minor groove by ecteinascidin 743, a potent antitumor compound from the Caribbean tunicate *Ecteinascidia turbinata*, Biochemistry, 35(41):13303-9 (1996).
Pospiech et al., A new *Myxococcus xanthus* gene cluster for the biosynthesis of the antibiotic saframycin Mx1 encoding a peptide synthetase, Microbiology, 141(Pt. 8):1793-803 (1995).
Ragin et al., Mapping and analysis of HPV16 integration sites in a head and neck cancer cell line, Int. J. Cancer, 110(5):701-9 (2004).
Rath et al., Meta-omic analysis of a marine invertebrate microbial consortium provides a direct route to identify and characterize natural product biosynthetic systems, ACS Chem. Biol., 6(11):1244-56 (2011).
Rinehart et al., Eceteinascidins 729, 743, 759A, 759B, and 770: Potenti antitumor agents from the Caribbean tunicate *Ecteinascidia turbinata*, J. Org. Chem., 55:4512-5 (1990).
Rinehart, Antitumor compounds from tunicates, Med. Res. Rev., 20(1):1-27 (2000).

(56) References Cited

OTHER PUBLICATIONS

Sakai et al., Ecteinascidins: putative biosynthetic precursors and absolute stereochemistry, J. Am. Chem. Soc., 118(38):9017-23 (1996).
Scherlach et al., Antimitotic rhizoxin derivatives from a cultured bacterial endosymbiont of the rice pathogenic fungus *Rhizopus microsporus*, J. Am. Chem. Soc., 128(35):11529-36 (2006).
Schloss et al., Metagenomics for studying unculturable microorganisms: cutting the Gordian knot, Genome Biology, 6:229 (2005).
Schmidt, Trading molecules and tracking targets in symbiotic interactions, Nat. Chem. Biol., 4(8):466-73 (2008).
Schwarzer et al., Nonribosomal peptides: from genes to products, Nat. Prod. Rep., 20(3):275-87 (2003).
Seaman et al., Molecular basis for the DNA sequence selectivity of Ecteinascidin 736 and 743: Evidence for the dominant role of direct readout via hydrogen bonding, J. Am. Chem. Soc., 120:13028-41 (1991).
Sharp et al., Localization of 'Candidatus Endobugula sertula' and the bryostatins throughout the life cycle of the bryozoan *Bugula neritina*, ISME J., 1(8):693-702 (2007).
Stachelhaus et al., Biochemical characterization of peptidyl carrier protein (PCP), the thiolation domain of multifunctional peptide synthetases, Chem. Biol., 3(11):913-21 (1996).
Stachelhaus et al., Peptide bond formation in nonribosomal peptide biosynthesis. Catalytic role of the condensation domain, J. Biol. Chem., 273(35):22773-81 (1998).
Stachelhaus et al., The specificity-conferring code of adenylation domains in nonribosomal peptide synthetases, Chem. Biol., 6(8):493-505 (1999).
Sudek et al., Identification of the putative bryostatin polyketide synthase gene cluster from "Candidatus Endobugula sertula", the uncultivated microbial symbiont of the marine bryozoan *Bugula neritina*, J. Nat. Prod., 70(1):67-74 (2007).
Takebayashi et al., Poisoning of human DNA topoisomerase I by ecteinascidin 743, an anticancer drug that selectively alkylates DNA in the minor groove, Proc. Natl. Acad. Sci. USA, 96(13):7196-201 (1999).
Tang et al., Cloning and heterologous expression of the epothilone gene cluster, Science, 287(5453):640-2 (2000).
Trauger et al., Peptide cyclization catalysed by the thioesterase domain of tyrocidine synthetase, Nature, 407(6801):215-8 (2000).
Udwary et al., Genome sequencing reveals complex secondary metabolome in the marine actinomycete *Salinispora tropica*, Proc. Natl. Acad. Sci. USA, 104(25):10376-81 (2007).
Velasco et al., Molecular characterization of the safracin biosynthetic pathway from *Pseudomonas fluorescens* A2-2: designing new cytotoxic compounds, Mol. Microbiol., 56(1):144-54 (2005).
Walsh et al., Tailoring enzymes that modify nonribosomal peptides during and after chain elongation on NRPS assembly lines, Curr. Opin. Chem. Biol., 5(5):525-34 (2001).
Wang et al., Discovery of platencin, a dual FabF and FabH inhibitor with in vivo antibiotic properties, Proc. Natl. Acad. Sci. USA, 104(18):7612-6 (2007).
Wang et al., Naive Bayesian classifier for rapid assignment of rRNA sequences into the new bacterial taxonomy, Appl. Environ. Microbiol., 73(16):5261-7 (2007).
Wenzel et al., Recent developments towards the heterologous expression of complex bacterial natural product biosynthetic pathways, Curr. Opin. Biotechnol., 16(6):594-606 (2005).
Wexler et al., TatD is a cytoplasmic protein with DNase activity. No requirement for TatD family proteins in sec-independent protein export, J. Biol. Chem., 275(22):16717-22 (2000).
Yamamoto et al., Gamma-butyrolactone-dependent expression of the *Streptomyces* antibiotic regulatory protein gene srrY plays a central role in the regulatory cascade leading to lankacidin and lankamycin production in *Streptomyces rochei*, J. Bacteriol., 190(4):1308-16 (2008).
Yin et al., Genome-wide high-throughput mining of natural-product biosynthetic gene clusters by phage display, Chem. Biol., 14(3):303-12 (2007).
Young et al., Chemical defense and aposematic coloration in tadpole larvae of the ascidian *Ecteinascidia turbinata*, Marine Biology. 96:539-544 (1987).
Zewail-Foote et al., Ecteinascidin 743: a minor groove alkylator that bends DNA toward the major groove, J. Med. Chem., 42(14):2493-7 (1999).
Zheng et al., Stereospecific formal total synthesis of ecteinascidin 743, Angew. Chem. Int. Ed. Engl., 45(11):1754-9 (2006).

SEQUENCE LISTING

```
<160> NUMBER OF SEQ ID NOS: 57

<210> SEQ ID NO 1
<211> LENGTH: 648
<212> TYPE: PRT
<213> ORGANISM: Ecteinascidia turbinata hologenome

<400> SEQUENCE: 1

Met Asn Glu Lys Asp Thr Leu Lys Gly Ser Tyr Ile Phe Ser Ala Ser
1               5                   10                  15

Pro Gly Gln Glu Arg Leu Trp Phe Leu Lys Glu Leu Asn Ser Gln Phe
            20                  25                  30

Gly Pro Ala Tyr Asn Ile Pro Ala Leu Phe Lys Ile Asn Gly Phe Leu
        35                  40                  45

Asn Ile Ile Ser Leu Gln Lys Ser Ile Asn Lys Ile Val Glu Arg His
    50                  55                  60

Glu Ile Leu Arg Thr Ala Leu Ile Tyr Asp Gly Thr Lys Leu Leu Gln
65                  70                  75                  80

Val Ile Lys Pro Asn Phe Leu Lys Thr Ile Arg Tyr Val Asp Cys Thr
                85                  90                  95

Ile Lys Glu Lys Arg Lys Lys Phe Leu Glu Ser Ser Leu Ile Gln Glu
            100                 105                 110

Ser Ser Val His Phe Asn Phe Thr Gln Pro Gly Ile Phe Asp Leu Ile
        115                 120                 125

Leu Tyr Lys Phe Gln Glu Lys Val Tyr Tyr Ile Leu Ile Asn Ile His
    130                 135                 140

His Ile Ile Ser Asp Gly Ile Ser Leu Glu Ile Phe Val Tyr Glu Leu
145                 150                 155                 160

Phe Glu Tyr Tyr Tyr Phe Ile Glu Asn Lys Ile Lys Ile Lys Lys Lys
                165                 170                 175
```

```
Asp Leu Glu Ile Gln Phe Ala Asp Phe Val Lys Trp Asn Glu Lys Trp
            180                 185                 190

Val Ser Ser Ser Lys Tyr Leu Glu Tyr Glu Leu Phe Trp Lys Lys Lys
        195                 200                 205

Gln Lys Asp Phe Val Leu Asn Leu Thr Leu Pro Lys Arg Asn Arg Asn
    210                 215                 220

Ile Asp Thr Ile Ile Gly Asn Asn Val Asn Phe Glu Leu Ser Thr Ser
225                 230                 235                 240

Ile Ile Asp Leu Leu Ile Lys Glu Ser Lys Lys Leu His Val Ser Leu
                245                 250                 255

Tyr Ala Phe Tyr Leu Ser Ile Phe Ala Ile Leu Ile Tyr Phe Phe Ser
            260                 265                 270

Asn Gln Lys Lys Phe Leu Ile Gly Ile Pro Leu Ala Asn Arg Lys Asn
        275                 280                 285

Gln Gln Thr Gln Asn Ile Met Gly Phe Leu Ala Asn Thr Leu Val Leu
    290                 295                 300

Asn Ile Ala Ile Asp Leu Asn Gln Asn Leu Ser Asp Phe Ile Lys Asn
305                 310                 315                 320

Asn His Lys Asn Ile Leu Lys Leu Ile Lys Leu Glu Arg Phe Pro Tyr
                325                 330                 335

Ser Ser Leu His Lys Ile Ser Thr Asn Asn Ile His Asn Ser Glu Pro
            340                 345                 350

Ile Phe Lys Val Met Phe Gly Tyr Gln Glu Leu Glu Asn Lys Lys Phe
        355                 360                 365

Asn Ile Lys Glu Leu Asn Ile Glu Arg Ile Asn Phe Asn Thr Ile Phe
    370                 375                 380

Ser Lys Phe Asp Ile Ser Leu Phe Met Phe Gln Lys Gly Lys Gln His
385                 390                 395                 400

Arg Gly Leu Leu Glu Cys Arg Ser His Ile Phe Ser Lys Lys Glu Ser
                405                 410                 415

Glu Asn Phe Tyr Arg Tyr Phe Ser Asn Ile Cys Arg Ile Ala Lys Asn
            420                 425                 430

Thr Asn Ile Leu Ile Lys Asn Ile Gln Phe Tyr Glu Asn Asn Asp Ile
        435                 440                 445

Lys Phe Ala Lys Asn Leu Leu Lys Asn Pro Asp Asn Leu Tyr Leu Asn
    450                 455                 460

Lys Lys Leu Leu Glu Lys Val Val Asn Phe Asn Ile Lys Asn Lys Lys
465                 470                 475                 480

Phe Ser Ile Leu Asp Ala Thr Tyr Lys Gln Val Pro Ile Asn Ile Pro
                485                 490                 495

Gly Ile Leu Phe Ile Asn His His Asn Thr Tyr Leu Lys Val Arg Leu
            500                 505                 510

Thr Tyr Asp Lys Arg Leu Asn Leu Ile Glu Asp Asn Glu Lys Asp Gln
        515                 520                 525

Ser Asn Ile Ile Glu Asn Lys Tyr His Asp Phe Ile Lys Ala Asn Ser
    530                 535                 540

Lys Thr Glu Lys Ile Leu Glu Asn Ile Trp Lys Ser Leu Leu Arg Leu
545                 550                 555                 560

Asn Ser Ser Leu Ser Ile His Gln Ser Phe Phe Ser Ile Gly Gly His
                565                 570                 575

Ser Ile Leu Val Ala Lys Met Val Asn Asn Ile Asn Lys Lys Phe Asn
            580                 585                 590
```

```
Ile Val Ile Ser Ile Arg Asp Ile Phe Leu His Pro Thr Ile Ser His
        595                 600                 605

Ile Ala Ser Lys Ile Glu Ser Leu Lys Glu Lys Glu Ile His Asn Thr
    610                 615                 620

Asn Ile Asn Pro Gln Asn Leu Lys Lys Glu Asp Ile Val Glu Ile Tyr
625                 630                 635                 640

Lys Asp Ile Asn Gly Lys Lys Ile
                645


<210> SEQ ID NO 2
<211> LENGTH: 1444
<212> TYPE: PRT
<213> ORGANISM: Ecteinascidia turbinata hologenome

<400> SEQUENCE: 2

Met Asp Ser Asn Phe Pro Ser Ser Asp Ala Tyr Phe Phe Glu Ala Asn
1               5                   10                  15

Ile Phe Phe Asp Lys Ala Ile Leu Gln Gln Ser Ile Ala Phe Ser Ile
            20                  25                  30

Thr Asn Phe Pro Ile Phe Arg Ser Ile Phe Ile Asn Ile Phe Gly Ser
        35                  40                  45

Pro Ile Arg Lys Thr Gln Leu Ser Ser Ile Ile Ser Ile Lys Leu Asp
    50                  55                  60

Asn Leu Tyr Gln Asp Asn Asn Lys Ile Asp Lys Val Lys Trp Ile Ser
65                  70                  75                  80

Asn Asn Lys Lys Asn Asn Thr Ile Asn Ile Ser Gln Gly Pro Leu Phe
                85                  90                  95

Asn Ile Phe Cys Leu Lys His Ser Asp Lys Lys Phe Asn Ile Leu Phe
            100                 105                 110

Leu Val Ser Arg Leu Val Ser Asn Lys Lys Leu Ile Ile Ser Phe Met
        115                 120                 125

Lys Asn Ile Phe Phe Arg Tyr Gln Asn Phe Leu Tyr His Asn Glu Asn
    130                 135                 140

Glu Lys Ile Ile Ser Tyr Glu Arg Asn Ile Ser Glu Lys Phe Phe Tyr
145                 150                 155                 160

Leu Glu Asn Gln Trp Ile Glu Thr Glu Asn Phe Lys Asn His Ile Lys
                165                 170                 175

Phe Trp Lys Lys Glu Val Lys Asp Leu Ser Asp Leu Asp Leu Gln Thr
            180                 185                 190

Asp Phe Lys Arg Pro Glu Ile Lys Thr Asn Lys Gln Lys Ser Val Phe
        195                 200                 205

Leu Lys Leu Glu Lys Tyr Lys Ile Leu Asn Ile Phe Asn Lys Ile Lys
    210                 215                 220

Lys Glu Lys Tyr Asn Tyr Glu Glu Phe Phe Leu Ser Ile Phe Val Thr
225                 230                 235                 240

Ile Leu Tyr Lys Tyr Ser Asn Asn Asn Asn Phe Ala Ile Gly Leu Lys
                245                 250                 255

Ala Asn Lys Leu Glu Lys Tyr Phe Asp Lys Asn Asn Ile Ser Pro Ile
            260                 265                 270

Glu Asn Glu Leu Pro Phe Lys Ile Asn Leu Asn Ser Ser Phe Ser Phe
        275                 280                 285

Lys Lys Ile Leu Ser Ile Ile Ser Lys Lys Tyr Asn Leu Phe Leu Arg
    290                 295                 300

Tyr Ser Thr Leu Pro Ile Lys Ile Leu Leu Asp Lys Ile Gly Val Asn
305                 310                 315                 320
```

```
Arg Asp Leu Lys Lys Thr Pro Phe Phe Gln Val Ser Phe Gln Tyr Glu
                325                 330                 335

Asn Phe Ser Phe Pro Ile Trp Asn Asn Lys Lys Asn Asn Phe Leu Lys
            340                 345                 350

Gln Ile Pro Ile Leu Glu Gly Ile Asn Ile Met Asp Phe Thr Phe Cys
        355                 360                 365

Ala Ile Glu Thr Lys Ser Ser Phe Ile Leu Arg Ile Asp Phe Asn Pro
    370                 375                 380

Asp Leu Phe Leu Asp Ser Ser Met Ile Phe Leu Leu Ser Ala Ile Glu
385                 390                 395                 400

Glu Leu Leu Met Phe Ile Ser Asn Asn Ser Trp Asp Ile Ser Ile Arg
                405                 410                 415

Asp Leu Ser Ile Ile Ser Asn Met Met Leu Lys Lys Ile Glu Lys Arg
            420                 425                 430

Trp Asn Ala Pro Lys Lys Ile Leu Phe Glu Asn Phe Glu Val His Lys
        435                 440                 445

Asn Phe Glu Asn Gln Cys Lys Lys Thr Pro Ser Asn Ile Ala Ile Ile
    450                 455                 460

Cys Gln Gly Glu Thr Ile Thr Tyr Arg Glu Leu Asn Glu Arg Ala Asn
465                 470                 475                 480

Gln Ile Ser His Tyr Leu Ile His Lys Lys Leu Leu Phe Asn Glu Lys
                485                 490                 495

Val Gly Ile Leu Met Asp Arg Ser Ile Glu Phe Ile Ile Ser Ile Leu
            500                 505                 510

Ala Ile Leu Lys Ile Asn Cys Ile Tyr Val Pro Ile Asp Glu Lys Tyr
        515                 520                 525

Pro Ile Glu Arg Ile Asn Tyr Ile Ile Asn Asp Ser Gln Ile Lys Leu
    530                 535                 540

Leu Ile Thr Lys Ser Tyr Ile Gln Lys Asn Lys Asn Ile Ile Tyr Lys
545                 550                 555                 560

Asn Leu Ile Tyr Leu Asp Lys Asp Trp Pro Leu Ile Glu Ile Lys Ser
                565                 570                 575

Arg Glu Asn Leu Asn Phe Ser Thr Asn Ile Gln Lys Asn Gly Met Tyr
            580                 585                 590

Met Ile Tyr Thr Ser Gly Ser Thr Gly Gln Pro Lys Gly Val Ile Leu
        595                 600                 605

Asn His Phe Gly Val Leu Asn Asn Ile Ser Trp Arg Gln Asn Lys Trp
    610                 615                 620

Asn Leu Asn Glu Lys Asp Arg Ile Leu Leu Asn Thr Ser Phe Ser Phe
625                 630                 635                 640

Asp Pro Ser Ile Trp Ser Ile Phe Trp Pro Leu Leu Phe Gly Gly Ala
                645                 650                 655

Phe Ile Ile Val Pro Leu Ser Ile Gln Asn Asp Ile Tyr Glu Leu Ile
            660                 665                 670

Lys Leu Ile Lys Lys Tyr Asn Ile Ser Ile Ile Gly Thr Ile Pro His
        675                 680                 685

Ile Ile Asp Leu Leu Val Ser Asn Ile Ala Ile Arg Asn Cys Asn Ser
    690                 695                 700

Leu Arg Leu Ile Leu Ser Gly Gly Glu Pro Leu Ser Gln Lys Ile Val
705                 710                 715                 720

Gln Lys Val Phe Asn Arg Thr Asn Ala Lys Leu Phe Ser Leu Tyr Gly
                725                 730                 735
```

```
Pro Thr Glu Thr Thr Ile Asp Ala Gly Ile Tyr Glu Cys Lys Pro Asp
            740                 745                 750

Asp Ile Val Gln Thr Ala Pro Ile Gly Lys Ala Ile Asp Asn Thr Arg
        755                 760                 765

Ile Tyr Ile Leu Asp Glu Asn Leu Arg His Val Pro Asp Gly Val Lys
    770                 775                 780

Gly Glu Ile Tyr Ile Ser Gly Pro Gly Val Ala Ile Gly Tyr His Asn
785                 790                 795                 800

Arg Lys Asp Leu Asn Ala Lys Ser Phe Leu Lys Asp Asn Ile Phe Tyr
                805                 810                 815

Ser Glu Leu Lys Tyr Met Tyr Lys Thr Gly Asp Leu Gly Val Phe Cys
            820                 825                 830

Tyr Asp Asp Asn Ile Lys Phe Leu Gly Arg Ile Asp Asn Gln Val Lys
        835                 840                 845

Ile His Gly Asn Arg Ile Glu Cys Ser Glu Ile Glu Ser Val Leu Ile
    850                 855                 860

Asn Ile Lys Lys Val Lys Glu Ser Ala Val Ile Val Asp Asn Pro Tyr
865                 870                 875                 880

Thr Glu Lys Thr Lys Leu Ile Ala Phe Leu Ala Val Ser Glu Leu Asp
                885                 890                 895

Val Lys Lys Glu Asp Ile Gln Lys Lys Leu Lys Asn Lys Leu Pro Lys
            900                 905                 910

Tyr Met Leu Pro Asp Lys Ile Ile Leu Leu Ile Ser Leu Pro Lys Leu
        915                 920                 925

Glu Asn Gly Lys Ile Asp Lys Asn Ala Leu Phe Arg Ile Tyr Asn Thr
    930                 935                 940

Ser Lys Asn Asn Lys Ser Ala Leu Leu Glu Asn Lys Leu Pro Asn Asn
945                 950                 955                 960

Pro Ile Glu Lys Ile Val Phe Lys Tyr Phe Cys Asp Val Leu Ser Leu
                965                 970                 975

Ser Asn Ile Ser Ile His Asp Asp Phe Phe Lys Leu Gly Gly Thr Ser
            980                 985                 990

Ile Leu Leu Ala Arg Leu Ser Asn  Leu Leu Phe Asn His  Phe Asp Ile
        995                 1000                 1005

Ser Leu  Pro Leu His Gln Phe  Phe Lys Ile Pro Thr  Val Leu Gly
    1010                 1015                 1020

Val Ser  Asn Ile Ile Val Thr  Leu Gln Lys Glu Gly  Ile Asp Lys
    1025                 1030                 1035

Ala Leu  Leu Asp Lys His Ile  Ser Lys Leu Glu Glu  Asp Ala Glu
    1040                 1045                 1050

Leu Ile  Lys Asp Ile Ser Pro  Lys Asn Leu Pro Lys  Gly Asn Phe
    1055                 1060                 1065

Tyr Asn  Pro Lys Asn Ile Leu  Ile Thr Gly Ser Thr  Gly Tyr Ile
    1070                 1075                 1080

Gly Ser  Phe Ile Leu Gln Glu  Leu Leu Ile Asn Thr  Asn Ala Thr
    1085                 1090                 1095

Ile Tyr  Cys Leu Ile Arg Ser  Lys Asn Pro Glu Lys  Ala Leu Ile
    1100                 1105                 1110

Lys Leu  Lys Asn Lys Met Lys  Glu Phe Tyr Ile Trp  Lys Glu Val
    1115                 1120                 1125

Tyr Thr  Lys Arg Ile Val Cys  Leu Val Gly Asp Leu  Gly Glu Lys
    1130                 1135                 1140

Asn Ile  Gly Leu Asn Lys Lys  Ile Trp Glu Asn Leu  Ser Lys Lys
```

```
    1145                1150                1155

Ile Glu  Val Ile Phe His Ala  Gly Ala Leu Val Asn  Phe Ala Tyr
    1160                1165                1170

Pro Tyr  Ser Ala Leu Lys Ala  Ala Asn Val Glu Gly  Thr Lys Glu
    1175                1180                1185

Ile Phe  Arg Phe Ser Cys Lys  Asn Leu Leu Lys Ser  Val His Tyr
    1190                1195                1200

Ile Ser  Thr Ile Asp Val Leu  Leu Ala Thr His Ile  Pro Arg Pro
    1205                1210                1215

Phe Leu  Glu Asn Asp Ala Pro  Leu Lys Val Ser Ile  Asp Ile Pro
    1220                1225                1230

Gly Gly  Tyr Thr Gly Ser Lys  Trp Val Ala Glu Lys  Ile Ala His
    1235                1240                1245

Ser Ala  Met Ile Arg Gly Ile  Pro Thr Ser Ile Tyr  Arg Pro Gly
    1250                1255                1260

Leu Val  Met Ser His Ser Glu  Thr Gly Ala Thr Gln  Thr Asn Asp
    1265                1270                1275

Tyr Leu  Leu Val Ala Phe Lys  Gly Phe Ile Pro Lys  Lys Val Ile
    1280                1285                1290

Pro Glu  Tyr Ala Arg Ile Phe  Asp Ile Val Pro Val  Asp Phe Val
    1295                1300                1305

Ala Lys  Ser Ile Val Tyr Ala  Ser Met Gln Lys Asn  Val His Gly
    1310                1315                1320

Lys Phe  Tyr His Ile Phe Asn  Pro Lys Pro Thr Thr  Leu Tyr Gln
    1325                1330                1335

Phe Cys  Asn Trp Ile Lys Asn  Tyr Gly Tyr Ser Phe  Asp Ile Ile
    1340                1345                1350

Pro Phe  Glu Ile Gly Arg Lys  Ile Ala Leu Asp Ser  Lys Glu Ser
    1355                1360                1365

Asp Pro  Leu Tyr Pro Leu Val  Pro Leu Ile Arg Asp  Ala Asp Pro
    1370                1375                1380

Asn Pro  His Arg Pro Leu Asp  Pro Lys Tyr Ile Asn  Glu Val Gln
    1385                1390                1395

Pro Glu  Ile Glu Cys Lys Asn  Met Asn Thr Ile Leu  Gln Lys Ser
    1400                1405                1410

Gly Ile  Ile Cys Pro Asn Met  Asn Glu Lys Leu Thr  His Leu Cys
    1415                1420                1425

Leu Lys  Tyr Leu Ile Asn Ile  Gly Tyr Phe Pro His  Pro Lys Lys
    1430                1435                1440

Ile


<210> SEQ ID NO 3
<211> LENGTH: 1790
<212> TYPE: PRT
<213> ORGANISM: Ecteinascidia turbinata hologenome

<400> SEQUENCE: 3

Met Lys Lys Met Ile Asn Tyr Lys Glu His Glu Ile Thr Ser Phe Val
1               5                   10                  15

Asp Ile Ile Leu Leu Arg Ser His Thr Val Pro Asp Lys Lys Met Leu
            20                  25                  30

Thr Tyr Leu Thr Ser Phe Asp Glu Lys Lys Glu Leu Thr Tyr Lys Lys
        35                  40                  45

Ile Asn Lys Ile Ser Gln Gln Ile Ala Val Lys Ile Leu His Tyr Leu
```

```
    50                  55                  60

Ser Pro Gly Asp Arg Ala Leu Ile Phe His Lys Pro Ser Ile Asp Tyr
65                  70                  75                  80

Ile Thr Ala Leu Phe Gly Cys Leu Tyr Ala Gly Ile Ile Ala Ile Pro
                85                  90                  95

Val Tyr Gly Pro Glu His Gly Ile Asn Lys Asn Lys Leu Tyr Arg Leu
            100                 105                 110

Lys Asn Ile Ile Lys Asp Ser Gly Ala Lys Gly Ile Leu Leu Ser Tyr
        115                 120                 125

Lys Glu Leu Lys Asn Cys Gln His Phe Phe Ser Asn Phe Tyr Ile His
    130                 135                 140

Lys Glu Lys Ile His Tyr Ile Thr Thr Asp Asp Thr Ser Asn Ile Asp
145                 150                 155                 160

Phe Gln Asp Trp Lys Lys Pro Tyr Phe Asn Lys Asn His Thr Ser Ile
                165                 170                 175

Ile Gln Tyr Thr Ser Gly Ser Thr Ser Asp Pro Lys Gly Val Met Leu
            180                 185                 190

Asn His Thr Asn Leu Ile Ser Asn Ile Leu Ser Ile Gln Asn Ile Phe
        195                 200                 205

Glu Met Lys Lys Asn Lys Gly Lys Ala Val Ile Trp Leu Pro Pro Tyr
    210                 215                 220

His Asp Met Gly Leu Ile Gly Gly Ile Leu Thr Pro Ile Phe Val Asp
225                 230                 235                 240

Phe Pro Leu Ile Leu Ile Ser Pro Leu Leu Phe Ile Gln Asn Pro Ile
                245                 250                 255

Phe Trp Leu Lys Leu Ile Ser Met Glu Lys Ala Thr Ile Thr Gly Gly
            260                 265                 270

Pro Asn Phe Ala Phe Asp Leu Cys Ser Asn Lys Ala Ile Ile Arg Lys
        275                 280                 285

Leu Asn Asn Ile Asp Leu Ser Ser Ile Lys His Ile Phe Ser Gly Ala
    290                 295                 300

Glu Pro Ile Asn Pro Glu Val Ile Asn Lys Phe Phe Glu Ile Tyr Glu
305                 310                 315                 320

Lys Phe Gly Leu Ser Lys Lys Ser Phe Ser Thr Cys Tyr Gly Leu Ala
                325                 330                 335

Glu Ser Thr Leu Met Val Thr Ser Ser Lys Ile Glu Asn Asn Lys Glu
            340                 345                 350

Ile Lys Glu Lys Glu Phe Phe Phe Lys Lys Asn Ile Val Glu Val Phe
        355                 360                 365

Lys Lys Asn Gln Lys Ser Phe Ser Leu Ser Lys Lys Leu Phe Ser Cys
    370                 375                 380

Gly Lys Ile Ile Pro Asn His Lys Leu Ala Ile Val Asp Pro Lys Lys
385                 390                 395                 400

Ser Lys Lys Leu Asn Glu Lys Val Ile Gly Glu Ile Tyr Val Lys Gly
                405                 410                 415

Pro Ser Val Ser Lys Gly Tyr Trp Lys Asn Pro Lys Lys Thr Lys Asn
            420                 425                 430

Ile Phe Gln Asn Phe Phe Ile Lys Glu Asn Lys Lys Lys Ser Tyr Gly
        435                 440                 445

Trp Leu Lys Thr Gly Asp Leu Gly Phe Leu Tyr Asn Ser Gln Leu Tyr
    450                 455                 460

Val Thr Gly Arg Ile Lys Asp Leu Ile Ile Ile Arg Gly Glu Asn Phe
465                 470                 475                 480
```

```
Tyr Pro Gln Asp Ile Glu Asn Tyr Val Lys Glu Leu Asn Ser Lys Ile
                485                 490                 495

Gln Leu Cys Asn Ser Ala Ala Phe Glu Ile Asp Lys Asn His Ile Lys
            500                 505                 510

Glu Val Val Leu Leu Gln Glu Ile Arg Lys Lys Asn Leu Ser Glu Asn
        515                 520                 525

Phe Glu Asn Leu Ala Leu Asp Ile Arg Lys Ser Ile Leu Asp Lys Leu
    530                 535                 540

Asn Leu Leu Ile His Asn Ile Ile Phe Ile Glu Lys Gly Ala Leu Pro
545                 550                 555                 560

Lys Thr Thr Ser Gly Lys Ile Gln Arg Phe Leu Ala Lys Lys Tyr Tyr
                565                 570                 575

Leu Ser Asn Ser Phe Asn Ile Ile Phe Ser Phe Asn Ser Gln Leu Lys
            580                 585                 590

Glu Lys Tyr Lys Lys Ile Asn Tyr Val Gln Lys Tyr Tyr Ile Gln Ser
        595                 600                 605

Leu Lys Lys Glu Glu Lys Lys Ile Tyr Tyr Ser Ile Ile Lys Phe Ile
    610                 615                 620

Gln Arg Tyr Gln Asn Leu Asn Lys Asp Ile Ile Asn Phe Thr Ile Leu
625                 630                 635                 640

Glu Ile Gly Leu Asp Ser Leu His Met Met Glu Leu Lys Asn Phe Leu
                645                 650                 655

Glu Glu Lys Tyr Lys Ile Ile Leu Asn Met His Ser Phe Leu Glu Asp
            660                 665                 670

Thr Lys Ile Phe Thr Leu Val Lys Glu Val Phe Asn Lys His Lys Glu
        675                 680                 685

Asn Ile Gln Lys Ile Tyr Ile Lys Lys Glu Lys Lys Lys Asn Val Leu
    690                 695                 700

Lys Asn Gln Val Ser Lys Tyr Phe Ser Val Asp Pro Gly Lys Ser Ser
705                 710                 715                 720

Ile Tyr Tyr Asn Tyr Leu Val Gln Lys Glu Asn Ser Ile Tyr Glu Ile
                725                 730                 735

Phe Arg Ile Ile Lys Ile Ser Lys Ser Ile Asn Ile Lys Leu Leu Glu
            740                 745                 750

Lys Ser Ile His Ile Leu Leu Asn Met Tyr Pro Thr Leu Lys Ser Arg
        755                 760                 765

Phe Ile Val Lys Asn Thr Gly Ile Val Tyr Gln Glu Tyr Pro Val Glu
    770                 775                 780

Leu Ser Phe Ser Ser Ile Phe Arg Lys Ile Asn Cys Lys Asp Ile Asp
785                 790                 795                 800

Leu Lys Glu Thr Cys Asn Ile Phe Leu Lys Glu Arg Phe Asn Met Glu
                805                 810                 815

Lys Gly Pro Leu Phe Asn Ile Ile His Ile Asn Asn Ile Lys Leu Asp
            820                 825                 830

Tyr Asn Ile Leu Ile Phe Lys Ile His His Ile Ile Ala Asp Phe Trp
        835                 840                 845

Ser Ile Ile Ile Ile Tyr Gln Asn Ile Glu Asn Ile Tyr Asn Asn Leu
    850                 855                 860

Leu Lys Asn Asn Ser Ile Lys Asn Ile Lys Ile Tyr Glu Thr Phe Gln
865                 870                 875                 880

Asp Val Gln Asn Lys Lys Tyr Lys Lys Tyr Ile Gln Ser Asn Gln Phe
                885                 890                 895
```

```
Ile Glu Asp Asn Leu Phe Trp Lys Arg Tyr Leu Ser Lys Tyr Asn Leu
            900                 905                 910

Leu Glu Asn Thr Asn Asn Ile Lys Arg Lys Asn Ile Gln Ser Phe Gln
        915                 920                 925

Phe Asn Leu Asn Phe Asn Phe Tyr Asn Asn Leu Leu Ile Phe Ser Lys
    930                 935                 940

Lys Lys Lys Ile Thr Pro Tyr Thr Ile Leu Leu Ile Ile Tyr Gln Ile
945                 950                 955                 960

Thr Tyr Tyr Arg Ile Tyr Lys Arg Asp Tyr Phe Ile Thr Gly Thr Pro
                965                 970                 975

Val Ala Leu Arg Asp Asp Tyr Leu Leu Arg Asn Tyr Ile Gly Tyr Cys
            980                 985                 990

Val Asn Ile Leu Pro Ile Val Ser  Asp Phe Ser Lys Gln  Asn Asp Ile
        995                 1000                 1005

Tyr Ser  Phe Thr Glu Lys Val  Lys Asn Asp Ile Lys  Asn Ile Leu
    1010                 1015                 1020

Gln His  Lys Tyr Phe Tyr Phe  Ser Lys Ile Ile Glu  Leu Leu Lys
    1025                 1030                 1035

Leu Pro  Arg Asn Thr Asp Tyr  Ile Pro Leu Phe Asn  Ser Leu Phe
    1040                 1045                 1050

Ile Tyr  Gln Thr Asp His Ile  Gly Ser Phe His Phe  Leu Asn Thr
    1055                 1060                 1065

Ile Ala  Ala Asn Ile Lys Asp  Ser Glu Phe Gln Phe  Leu Gly Tyr
    1070                 1075                 1080

Pro Ala  Ser Ile Trp Tyr Thr  Asn Asn Phe Asn Leu  Met His His
    1085                 1090                 1095

Phe Ile  Phe Asn Ile Ser Val  Asn Lys Glu Ser Tyr  Ser Ile Asn
    1100                 1105                 1110

Ile Glu  Tyr Asp Glu Asn Ile  His Asn Lys Ile Leu  Ile Lys Lys
    1115                 1120                 1125

Phe Ser  Glu Gln Phe Lys Leu  Thr Phe Gln Ala Ile  Ile Phe Asn
    1130                 1135                 1140

Lys Pro  Lys Ala Ile Ile Glu  Glu Lys Gln Tyr Leu  Phe Tyr Gln
    1145                 1150                 1155

Asn Ile  Asn Ser Thr Asn Lys  Lys Phe Phe Lys Ser  Gln Tyr Phe
    1160                 1165                 1170

Leu Asp  Gln Leu Phe Arg Lys  Gln Val Ile Lys Asn  Pro Asn Ala
    1175                 1180                 1185

Ser Ala  Ile Ile Phe Asp Asp  Ile Asn Ile Thr Tyr  Lys Lys Leu
    1190                 1195                 1200

Asn Lys  Tyr Val Asn Arg Val  Ser His Tyr Leu Ile  Asn His Ile
    1205                 1210                 1215

Leu Lys  Asn Glu Ile Leu Ile  Ala Ile Leu Met Glu  Lys Gly Ile
    1220                 1225                 1230

Glu Gln  Ile Val Ala Cys Leu  Ala Ile Leu Ser Ile  Gly Lys Ala
    1235                 1240                 1245

Tyr Leu  Pro Ile Asn Ile Asn  Phe Ser Lys Asn Lys  Ile His Glu
    1250                 1255                 1260

Ile Met  Val Leu Gly Lys Val  Lys Arg Phe Leu Ile  Gln Lys Lys
    1265                 1270                 1275

Tyr Leu  Lys Lys Phe Asn Phe  Lys Asp Phe Gln Ser  Ile Asp Val
    1280                 1285                 1290

Thr Ser  Ile Ile Glu Asn Ser  Ser Phe Lys Lys Ser  Gln Glu Tyr
```

```
    1295                1300                1305

Phe Pro  Lys Tyr Gln Leu Arg  Lys Leu Asn Asp Leu  Ala Tyr Val
    1310                1315                1320

Ile Phe  Thr Ser Gly Ser Thr  Gly Thr Pro Lys Gly  Val Met Ile
    1325                1330                1335

Glu His  Lys Gln Val Val Asn  Thr Ile Leu Asp Ile  Asn Glu Lys
    1340                1345                1350

Phe Gln  Val Asn Asn Leu Asp  Arg Ile Leu Ala Ile  Ser Asn Leu
    1355                1360                1365

Asp Phe  Asp Leu Ser Val Tyr  Asp Ile Phe Gly Ile  Leu Ser Ala
    1370                1375                1380

Gly Gly  Thr Leu Val Ile Val  Pro Ser Lys Phe Thr  Lys Glu Pro
    1385                1390                1395

Lys Tyr  Trp Leu Tyr Ala Ile  Gln Lys Tyr Gln Ile  Thr Ile Trp
    1400                1405                1410

Asn Ser  Val Pro Met Phe Lys  Gln Met Phe Ile Glu  Tyr Leu Gln
    1415                1420                1425

Gly Ile  Asp Lys Glu Ser Phe  Tyr Lys Lys Ile Lys  Leu Lys Leu
    1430                1435                1440

Ile Leu  Leu Ser Gly Asp Trp  Ile Pro Leu Asp Leu  Pro Glu Lys
    1445                1450                1455

Ile Phe  Lys Ile Tyr Lys Lys  Asn Phe Asp Ser Leu  Lys Val Val
    1460                1465                1470

Ser Leu  Gly Gly Ala Thr Glu  Cys Ser Ile Trp Ser  Asn Tyr Phe
    1475                1480                1485

Ile Ile  Asn Lys Asn Ile Lys  Tyr Lys Thr Ser Ile  Pro Tyr Gly
    1490                1495                1500

Lys Pro  Leu Ser Asn Gln His  Leu Tyr Ile Leu Asp  Ala Leu Met
    1505                1510                1515

Leu Pro  Thr Asn Ile Leu Val  Pro Gly Tyr Leu Tyr  Ile Gly Gly
    1520                1525                1530

Phe Gly  Val Ala Arg Gly Tyr  Trp Asp Asp Ile Lys  Lys Thr Asn
    1535                1540                1545

Glu Ser  Phe Tyr Phe His Lys  Glu Ile Gly Lys Arg  Ile Tyr Phe
    1550                1555                1560

Thr Gly  Asp Met Gly Gln Tyr  His Pro Asp Gly Asn  Ile Glu Phe
    1565                1570                1575

Leu Gly  Arg Lys Asp Arg Gln  Ile Lys Ile Asn Gly  Tyr Arg Ile
    1580                1585                1590

Glu Leu  Glu Glu Ile Gln Asn  Lys Leu Lys Ser His  Val Tyr Val
    1595                1600                1605

Lys Asp  Ser Phe Ile Thr Val  Asn Gln Asn Asn Ile  Ser Ala Lys
    1610                1615                1620

Ile Leu  Ala Phe Ile Ile Leu  His Asn Asn Ser Ser  Met Met Ser
    1625                1630                1635

His Thr  Asn Ile Lys Lys Glu  Leu Lys Ser Phe Leu  Tyr Lys Asn
    1640                1645                1650

Leu Ser  Glu Tyr Met Ile Pro  Asn His Phe Gln Phe  Leu Lys Lys
    1655                1660                1665

Phe Pro  Leu Ser Lys Asn Gly  Lys Ile Asp Glu Asn  Lys Leu Tyr
    1670                1675                1680

Lys Met  His Asp Ile Pro Ile  Leu Asn Ile Gln Lys  Ser Ala Asn
    1685                1690                1695
```

```
Thr Lys  Leu Gln Lys Ser Leu  Lys Glu Ile Trp Lys  Asp Leu Leu
    1700                 1705                 1710

Lys Ile  Lys Lys Asp Ile Tyr  Ile Asn Asp Asn Phe  Phe Gln Leu
    1715                 1720                 1725

Gly Gly  Ser Ser Leu Leu Ala  Val Arg Met Thr Asn  Leu Ile Ser
    1730                 1735                 1740

Lys Lys  Leu Asn Leu Asn Ile  Asp Val Ser Ala Val  Phe Lys Tyr
    1745                 1750                 1755

Gln Thr  Ile Glu Ser Leu Glu  Lys Phe Leu Gln Lys  Asp Lys Ile
    1760                 1765                 1770

Lys Ile  Glu Lys Asn Asn Ile  Thr Lys Gln Glu Arg  Ile Leu Tyr
    1775                 1780                 1785

Tyr Glu
    1790


<210> SEQ ID NO 4
<211> LENGTH: 262
<212> TYPE: PRT
<213> ORGANISM: Ecteinascidia turbinata hologenome

<400> SEQUENCE: 4

Met Pro Ile Leu Val Asp Ser His Cys His Leu Asp Ile Leu Asn Leu
1               5                   10                  15

Lys Glu Leu Lys Met Asn Leu Ala Asp Ile Ile Asp Glu Ala Tyr His
            20                  25                  30

Lys Asn Val Lys Tyr Leu Leu Ser Ile Cys Leu Asn Ile Glu Asn Leu
        35                  40                  45

Lys Thr Ile Ile Pro Ile Thr Glu Lys Phe Asn Asn Ile Tyr Ala Ser
    50                  55                  60

Ile Gly Lys His Pro Asn Glu Ile Lys Gly Lys Glu Pro Ser Thr Leu
65                  70                  75                  80

Asp Leu Ile Asn Ile Phe Asn Ala His Ser Lys Ile Ile Ala Val Gly
                85                  90                  95

Glu Ser Gly Leu Asp Tyr Tyr Arg Thr Lys Ser Glu Lys His Ile Leu
            100                 105                 110

Val Gln Lys Lys Arg Phe Ile Asn His Ile Gln Ala Ser Lys Lys Leu
        115                 120                 125

Asn Ala Pro Leu Ile Ile His Thr Arg Ser Ala Ser Gln Asp Thr Ile
    130                 135                 140

Ser Ile Leu Glu Lys Tyr Asn Val Asn Leu Gly Val Val His Cys Phe
145                 150                 155                 160

Thr Glu Ser Trp Glu Met Ala Lys Ile Ile Leu Asp Met Gly Leu Tyr
                165                 170                 175

Ile Ser Phe Ser Gly Ile Leu Thr Phe Lys Asn Ser Ala Asn Leu Arg
            180                 185                 190

Asp Leu Val Arg Lys Ile Pro Leu Asn Arg Ile Leu Ile Glu Thr Asp
        195                 200                 205

Ser Pro Tyr Leu Thr Pro His Pro Phe Arg Gly Lys Ser Asn Lys Pro
    210                 215                 220

Ser Tyr Val Asn Tyr Val Ala Lys Cys Ile Ser Lys Ile Lys Asn Leu
225                 230                 235                 240

Ser Tyr Ser Asp Ile Cys His Ala Thr Thr Asp Asn Phe Ser Gln Leu
                245                 250                 255

Phe Asn Ile Gln Ile Phe
```

260

<210> SEQ ID NO 5
<211> LENGTH: 304
<212> TYPE: PRT
<213> ORGANISM: Ecteinascidia turbinata hologenome

<400> SEQUENCE: 5

```
Met Ile Phe Phe Trp Gln Lys Thr Leu Trp Lys Lys Phe Asn Trp His
1               5                   10                  15

Leu Gln Asn Asn Lys Ile Pro Tyr Gly Leu Leu Leu Thr Gly Phe Pro
            20                  25                  30

Gly Thr Gly Lys Leu His Phe Val Lys Leu Cys Ala Gln Lys Ile Leu
        35                  40                  45

Ser Cys Asn Ser Ser Glu Leu Ser Glu His Pro Asp Leu Leu Tyr Ile
    50                  55                  60

Lys Pro Gln Gly Lys Leu Asn Gln Ile Gln Ile Asp Gln Ile Arg Asn
65                  70                  75                  80

Ile Ile Phe Phe Leu Gln Arg Thr Ser Trp Ile Gly Gly Tyr Arg Val
                85                  90                  95

Val Ile Ile Asp Lys Ser His Asn Met Asn Leu Phe Ala Tyr Asn Ala
            100                 105                 110

Phe Leu Lys Ile Leu Glu Glu Lys Arg Glu Lys Thr Ile Leu Ile Leu
        115                 120                 125

Thr Ala Asp Tyr Leu Glu Ser Ile Pro Leu Thr Ile Arg Ser Arg Cys
    130                 135                 140

Gln Ile Trp Tyr Met Asn Phe Phe Leu Glu Glu Lys Asn Gln Asn Leu
145                 150                 155                 160

Lys Asn Phe Phe Trp Glu Tyr Glu Ile Asn Asn Ser Lys Asn Leu Leu
                165                 170                 175

Asn Ile Phe Asn Ile Pro Gly Phe Gly Pro Ile Tyr Leu Glu Ile Trp
            180                 185                 190

Lys Lys Lys Gly Tyr Leu Lys Lys Ile Asn Ser Val Phe Gln Asn Phe
        195                 200                 205

Leu Asp Lys Lys Thr Pro Ile Phe Gln Thr Lys Lys Leu Gln Asp Ile
    210                 215                 220

Asp Leu Val Leu Ile Ile Asn Ser Leu Ile Gln Leu Val Tyr Asn Leu
225                 230                 235                 240

Ile Tyr Ile Leu Ile Leu Lys Lys Lys Asn Ser Ile Phe Trp Lys Leu
                245                 250                 255

Ala Lys Lys Lys Ser Leu Ser Gln Trp Phe Tyr Leu Ile Asp Phe Tyr
            260                 265                 270

Leu Val Glu Arg Lys Lys Ile Ile Lys Ile Asp Tyr Leu Phe Asn Thr
        275                 280                 285

Glu Leu Phe Leu Glu Gly Leu Phe Ile Glu Trp Tyr Leu Tyr Asn Glu
    290                 295                 300
```

<210> SEQ ID NO 6
<211> LENGTH: 207
<212> TYPE: PRT
<213> ORGANISM: Ecteinascidia turbinata hologenome

<400> SEQUENCE: 6

```
Met Arg Lys Leu Tyr Tyr Phe Phe Lys Ser Lys His Ile Ile Phe Ala
1               5                   10                  15

Cys Asp Ser Thr Gln Tyr Tyr Trp Arg Ser Lys Tyr Phe Ser Glu Tyr
```

```
            20                  25                  30

Lys Lys Asn Arg Lys Met Thr Thr Leu Arg Lys Asn Val Arg Asn Ser
        35                  40                  45

Ile Lys Phe Phe Lys Glu Lys Asn Phe Lys Leu Cys Ile Glu Val Pro
    50                  55                  60

Gly Cys Glu Ala Asp Asp Ile Ile Tyr Cys Leu Ile Asn Tyr Lys Ile
65                  70                  75                  80

His Asn Asn Ile Ile Ile Val Ser Ser Asp Arg Asp Phe Ile Gln Leu
                85                  90                  95

Gln Ser Thr Arg Val Arg Leu Phe Asn Pro His Thr Tyr Lys Phe Arg
            100                 105                 110

Lys Ile Pro Glu Lys Leu Glu Tyr Glu Leu Phe Ile Lys Cys Ile Arg
        115                 120                 125

Gly Asp Val Ser Asp Asn Ile Pro Ser Ala Tyr Pro Tyr Val Arg Glu
    130                 135                 140

Ser Leu Ile Lys Glu Ala Tyr Tyr Asn Pro Ser Lys Phe Phe Ile Phe
145                 150                 155                 160

Met Lys Lys Lys Leu Ser Asp Asn Ile Ala Val Tyr Lys Lys Tyr Gln
                165                 170                 175

Arg Asn Arg Leu Leu Ile Asp Met Lys Phe Leu Pro Lys Lys Tyr Ile
            180                 185                 190

Ser Leu Ile Lys Ile Leu Ile Asp Lys Leu Ser Leu Ile Glu Asp
        195                 200                 205


<210> SEQ ID NO 7
<211> LENGTH: 389
<212> TYPE: PRT
<213> ORGANISM: Ecteinascidia turbinata hologenome

<400> SEQUENCE: 7

Met Ile Lys Lys Leu Leu Ile Ala Asn Arg Gly Glu Ile Ala Leu Arg
1               5                   10                  15

Ile Leu Arg Ala Cys Arg Glu Leu Gln Ile Lys Thr Val Ala Val His
            20                  25                  30

Ser Thr Thr Asp Arg Asn Leu Lys His Val Lys Leu Ser Asp Glu Ser
        35                  40                  45

Val Cys Ile Gly Pro Ser Asn Ser Leu Lys Ser Tyr Leu Asn Ile Pro
    50                  55                  60

Ala Ile Ile Ser Ala Ala Glu Leu Thr Asp Ser Asp Ser Ile His Pro
65                  70                  75                  80

Gly Tyr Gly Phe Leu Ser Glu Ser Ser Asp Phe Val Ser Ala Val Glu
                85                  90                  95

Asn Ser Gly Phe Ile Phe Val Gly Pro Thr Ile Lys Asn Met Lys Asn
            100                 105                 110

Met Gly Asp Lys Ile Ser Ala Ile Asn Ile Met Lys Glu His Gly Ile
        115                 120                 125

Ser Cys Ile Glu Gly Ser Leu Gly Lys Leu Asp Thr Asp Thr Lys Lys
    130                 135                 140

Asn Gln Ile Leu Ala Lys Lys Ile Gly Tyr Pro Ile Ile Leu Lys Ala
145                 150                 155                 160

Ala Lys Gly Gly Gly Gly Leu Gly Ile Arg Val Val Tyr Asp Pro Glu
                165                 170                 175

Lys Leu Ser Asn Ser Ile Asp Met Thr Lys Thr Glu Ala Lys Ala Ser
            180                 185                 190
```

```
Phe Gly Asp Glu Asn Ile Tyr Met Glu Lys Phe Leu Glu Asn Pro Arg
        195                 200                 205

His Ile Glu Ile Gln Val Leu Gly Asp Gly Lys Gly Asn Ala Ile His
    210                 215                 220

Leu Gly Glu Arg Asp Cys Ser Ile Gln Arg Arg Asn Gln Lys Val Leu
225                 230                 235                 240

Glu Glu Ala Pro Ser Thr Leu Asn Arg Lys Asp Cys Glu Asn Leu Ala
                245                 250                 255

Lys Lys Cys Val Glu Val Cys Lys Lys Ile Met Tyr Arg Gly Ala Gly
            260                 265                 270

Thr Phe Glu Phe Leu Tyr Glu Lys Gly Glu Phe Phe Phe Ile Glu Met
        275                 280                 285

Asn Thr Arg Ile Gln Val Glu His Pro Val Thr Glu Phe Val Thr Gly
    290                 295                 300

Ile Asp Ile Val Lys Glu Gln Leu Gln Ile Ala Ser Asn Gln Thr Ile
305                 310                 315                 320

Thr Tyr His Gln Asn Asp Ile Asn Ile Lys Gly His Ser Ile Gln Cys
                325                 330                 335

Arg Ile Asn Ala Glu Asp Pro Lys Thr Phe Leu Pro Ser Pro Gly Thr
            340                 345                 350

Leu Asn Ile Tyr His Pro Pro Gly Gly Pro Gly Ile Arg Val Asp Ser
        355                 360                 365

His Ile Tyr Ser Gly Tyr Thr Ile Pro Pro Tyr Tyr Asp Ser Met Ile
    370                 375                 380

Gly Lys Ile Ile Ser
385


<210> SEQ ID NO 8
<211> LENGTH: 152
<212> TYPE: PRT
<213> ORGANISM: Ecteinascidia turbinata hologenome

<400> SEQUENCE: 8

Met Lys Ile Asn His Lys Asp Ile Gln Lys Leu Leu Glu Leu Met Asp
1               5                   10                  15

Asn Phe Ser Leu Ser Asp Met Lys Ile Val Gln Gly Glu Glu Ser Ile
            20                  25                  30

Gln Leu Ser Lys Lys Ser Asp Val Ser Asn Ile Leu Ser Ser Glu Arg
        35                  40                  45

Glu Thr Lys Lys Lys Leu Lys Lys Ser Asn Ser Ile Glu Phe Leu Lys
    50                  55                  60

Lys Glu Lys Lys Val Ser Asp Ile Tyr Ser Ser Ile Asn Ile Ile Lys
65                  70                  75                  80

Ser Pro Met Val Gly Thr Phe Tyr Arg Ser Pro Ser Pro Thr Ala Lys
                85                  90                  95

Pro Phe Ile Glu Val Gly Ser Val Ile Lys Ile Gly Gln Val Ile Gly
            100                 105                 110

Ile Ile Glu Ala Met Lys Thr Met Asn His Ile Glu Ser Asp Lys Ser
        115                 120                 125

Gly Ile Ile Lys Ser Ile Leu Ile Glu Asp Ser Ser Pro Val Glu Phe
    130                 135                 140

Asp Gln Pro Leu Ile Ile Leu Glu
145                 150


<210> SEQ ID NO 9
```

```
<211> LENGTH: 748
<212> TYPE: PRT
<213> ORGANISM: Ecteinascidia turbinata hologenome

<400> SEQUENCE: 9

Met Leu Asn Ser Lys Lys Ser Leu Leu Ile Gln Gly Leu Tyr Gly Lys
1               5                   10                  15

Ile Gln Ile Asn Leu Asp Ser Tyr Gly Ile Pro His Ile Phe Ala Ser
            20                  25                  30

Lys Asn Asp Ile Asp Ala Phe Tyr Gly Leu Gly Tyr Met His Ala Lys
        35                  40                  45

Asp Arg Phe Trp Gln Met Glu Leu Gln Arg His Ile Ala Ser Gly Thr
    50                  55                  60

Leu Ser Glu Ile Phe Gly Lys Arg Thr Ile Lys Glu Asp Lys Tyr Leu
65                  70                  75                  80

Lys Thr Trp Gly Phe Tyr Arg Cys Ala Lys Glu Asn Trp Lys His Phe
                85                  90                  95

Asn Ile Lys Thr Lys Lys Ile Ile Asn Gly Tyr Thr Ala Gly Val Asn
            100                 105                 110

Ala Tyr Ile Lys Ser Gly Lys Arg Pro Ile Glu Leu Arg Ile Leu Phe
        115                 120                 125

Tyr Lys Pro Lys Tyr Trp Lys Asn Ile Asp Ser Phe Ile Trp Ser Lys
    130                 135                 140

Ile Ile Ala Trp Gln Leu Gln Tyr His Thr Trp Gln Asp Lys Leu Asn
145                 150                 155                 160

Asn Ser Leu Ile Met Glu Lys Ser Ser Asp Ile Asn Ile Glu Asp Ile
                165                 170                 175

Arg Ile Gln Tyr Pro Glu Asn Ala Pro Thr Thr Leu Asn Ile Glu Glu
            180                 185                 190

Leu Asn Asn Ser Asn Leu Leu Asp Tyr Thr Gln Lys Ser Ser Asp Asn
        195                 200                 205

Leu Asn Thr Asn Lys Lys Asn Gln Val Leu Tyr Asn Asn Asn Met Gln
    210                 215                 220

Ser Phe Ile Asn Ile Ser Gln Glu Ile Gln Asn Asn Leu Asn Ile Gln
225                 230                 235                 240

Asn Leu Pro Gly Lys Gly Ser Asn Gly Trp Val Val Ser Gly Lys Leu
                245                 250                 255

Thr Lys Ser Gly Lys Pro Ile Leu Ala Asn Asp Ile His Leu Glu Leu
            260                 265                 270

Ser Ser Pro Asn Ile Cys Tyr Leu Ala Asn Ile Gln Gly Pro Ser Leu
        275                 280                 285

Asn Ile Arg Gly Ser Ser Ile Pro Gly Ile Pro Cys Ile Ile Ser Gly
    290                 295                 300

Glu Asn Lys Asn Ile Ala Trp Gly Ile Thr Asp Ala Gly Leu Asp Cys
305                 310                 315                 320

Ser Asp Leu Phe Leu Ile Asp Lys Thr Arg Pro Thr Lys Lys Ile Phe
                325                 330                 335

Glu Lys Ile Lys Val Arg Lys Lys Lys Thr Ile Gln His Glu Ile Glu
            340                 345                 350

Leu Ser Asp Ile Gly Pro Ile Ile Asn Asn Leu Ile Gln Glu Asn Asn
        355                 360                 365

Gln Ile Asn Lys Lys Ile Ile Asn Gln Lys Ile Ala Ile Arg Trp Thr
    370                 375                 380

Gly Leu Asp Ser Asp Asp Lys Thr Ile Gln Ser Leu Ile Glu Ile Asn
```

```
385                 390                 395                 400

Tyr Ala Ser Asn Trp Lys Glu Phe Lys Asn Ala Leu Lys Asp Phe Thr
                405                 410                 415

Ala Ala Pro Met Asn Phe Leu Tyr Ala Asp Ile Leu Gly Asn Ile Gly
            420                 425                 430

Tyr Tyr Leu Pro Gly Arg Ile Pro Ile Arg Lys Lys Glu Asn Leu Lys
        435                 440                 445

Tyr Val Ile Pro Phe Asn Ser Lys Asn Ala Trp Asn Glu Phe Ile Pro
    450                 455                 460

Phe Asn Lys Leu Pro His Val Phe Asn Pro Ser Lys Gly Tyr Ile Val
465                 470                 475                 480

Asn Ala Asn Asn Lys Ile Ile Pro Asn Glu Tyr Pro Tyr Asn Leu Thr
                485                 490                 495

Tyr Ile Trp Lys Gly Pro Pro Tyr Arg Ala Glu Lys Ile Glu Asn Met
            500                 505                 510

Ile Asn Asn Met Asn Lys Met Thr Ile Lys Asn Met Lys Asp Ile Gln
        515                 520                 525

Ile Asn Thr Asn Asn Leu Leu Trp Tyr Glu Leu Lys Asp Phe Leu Leu
    530                 535                 540

Lys Ile Ile Pro Gln Asn Lys Phe Glu Lys Lys Ile Leu Val Tyr Leu
545                 550                 555                 560

Lys Lys Trp Asn Gly Asn Met Ser Ser Asn Ser Ile Ser Ala Thr Val
                565                 570                 575

Phe Ser Phe Trp Phe Gln Glu Ile Ile Lys Ile Gln Pro Lys Leu Pro
            580                 585                 590

Ile Asn Tyr Gln Asn Phe Pro Asn Pro Leu Phe Ile Ile Asp Gln Leu
        595                 600                 605

Lys Lys Asn Gly Lys Phe Ile Cys Leu Asn Lys Lys Lys Asn Ile Thr
    610                 615                 620

Asp Val Leu Tyr Ile Leu Phe Lys Lys Ala Ile Ile Asn Ile Lys Asn
625                 630                 635                 640

Ile Leu Gly Asn Asn Ile Glu Lys Trp Lys Trp Gly Arg Ile His Gln
                645                 650                 655

Ala Lys Phe Ile Asn Pro Ile Phe Gly Lys Ile Trp Gly Ile Lys Tyr
            660                 665                 670

Leu Trp Asn Arg Lys Ile Ser Thr Glu Gly Asn Ala Tyr Thr Ile Asn
        675                 680                 685

Ala Ser Pro Tyr Asp Glu Asn Phe Ile Gln Lys Ala Gly Pro Val Tyr
    690                 695                 700

Arg Gln Ile Ile Asp Leu Asn Lys Lys Asn Lys Ser Cys Phe Ile Cys
705                 710                 715                 720

Pro Leu Gly Gln Ser Gly Asn Pro Phe Ser Lys Asn Tyr Asn Asn Met
                725                 730                 735

Leu Lys Phe Trp Lys Leu Gly Lys Tyr Ile Lys Leu
            740                 745


<210> SEQ ID NO 10
<211> LENGTH: 159
<212> TYPE: PRT
<213> ORGANISM: Ecteinascidia turbinata hologenome

<400> SEQUENCE: 10

Met Ile Ile Ile Gln Gly Leu Ile Ile Ser Leu Gln Cys Phe Ile Phe
1               5                   10                  15
```

```
Glu Tyr Ser Lys Lys Lys Phe Leu Gln Ser Leu Leu Tyr Leu Asn Asn
            20                  25                  30

Ala Ile Lys Leu Met Lys Ala Thr Glu Val Ala Leu Tyr Tyr Thr Gly
        35                  40                  45

Glu Phe Ser Ser Lys Ser Tyr Asn Glu Asn Val Arg Pro Thr Leu Met
    50                  55                  60

Pro Pro Ile Ser Gln Pro Glu Met Ser Gly Leu Asn Trp Arg Asp His
65                  70                  75                  80

Gln Phe Met Val Lys Asn Cys Met Arg Ser Ile Gly Lys Leu Asn Phe
                85                  90                  95

Thr Ser Tyr Pro Ile Ile Gln Lys Lys Tyr Asn Ile Phe Ile Ile Ser
            100                 105                 110

Leu Lys Lys Ala Tyr His Ala His Lys Tyr Val Cys Gly Lys Phe Val
        115                 120                 125

Gly Pro Ala Ser Gly Ser Leu Arg Ser Asn Glu Tyr Ser Ala Val Gln
    130                 135                 140

Glu Ile Glu Lys Phe Lys Lys Leu Arg Leu Lys Ile Leu Lys Gly
145                 150                 155


<210> SEQ ID NO 11
<211> LENGTH: 361
<212> TYPE: PRT
<213> ORGANISM: Ecteinascidia turbinata hologenome

<400> SEQUENCE: 11

Met Asp Lys Lys Ile Leu Lys Pro Cys Tyr Arg Ser Asp Ser Ile Leu
1               5                   10                  15

Asp His Asn Gln Leu Asn Lys Leu His Glu Leu Thr Pro Ile Ile Phe
            20                  25                  30

Gly Ala Ser Ala Phe Gln Tyr Leu Asn Ala Gly Ser Glu Ile Gly Leu
        35                  40                  45

Phe Glu Leu Leu Tyr Tyr Ser Gly Pro Lys Lys Lys Ser Glu Leu Met
    50                  55                  60

Ile Glu Leu Ser Leu Lys Glu Arg Ala Ile Asp Ile Leu Leu Leu Gly
65                  70                  75                  80

Asn Thr Ser Leu Asn Leu Ile Asn Lys Glu Lys Ser Phe Tyr Lys Asn
                85                  90                  95

Ser Leu Ile Ile Gln Thr Ile Phe Glu Asn Asn Ile Trp Asp Ile Phe
            100                 105                 110

Lys Asp Leu Ile Ala Phe Glu Gln Tyr Ile Val Tyr Leu Gly Gln Phe
        115                 120                 125

Asp Phe Thr Asp Ser Leu Arg Lys Asn Thr Asn Ile Gly Leu Gln Arg
    130                 135                 140

Ile Ser Asn Thr Ser Asn Ser Leu Tyr Lys Ser Phe Asn Lys Asn Lys
145                 150                 155                 160

Lys Leu Glu Lys Ile Phe Tyr Asn Tyr Met Asn Ser Trp Thr Arg Leu
                165                 170                 175

Ser Asn Tyr Tyr Leu Ile Lys Tyr Ile Asn Phe Asn Asn Val His Arg
            180                 185                 190

Leu Leu Asp Val Gly Gly Gly Thr Ala Ile Asn Ala Ile Ala Leu Ala
        195                 200                 205

Lys Lys Tyr Pro Lys Leu Lys Ile Thr Val Phe Glu Ile Asp Ala Ser
    210                 215                 220

Ala Lys Ile Ala Gln Lys Asn Ile Gln Ser Ser Gly Leu Ser Asn Gln
225                 230                 235                 240
```

```
Ile Asn Val Ile His Gly Asp Ile Phe Lys Asp Gln Phe Pro Thr Gly
                245                 250                 255

Tyr Asp Cys Val Leu Phe Ser His Gln Leu Val Ile Trp Thr Pro Glu
            260                 265                 270

Glu Asn Ile Glu Leu Leu His Lys Ala Tyr Lys Ile Leu Ser Ser His
        275                 280                 285

Gly Leu Val Ile Ile Phe Asn Ser Ile Ser Asn Asp Asp Gly Lys Gly
    290                 295                 300

Pro Leu Leu Ala Ala Leu Asp Ser Val Tyr Phe Ala Ser Ile Pro Ser
305                 310                 315                 320

Glu Gly Gly Met Ile Tyr Ser Trp Asn Gln Tyr Glu Glu Trp Leu Lys
                325                 330                 335

Lys Ser Lys Phe Gln Lys Ile Ser Arg Ile Asn Cys His His Trp Thr
            340                 345                 350

Pro His Gly Ile Ile Lys Ala Tyr Lys
        355                 360


<210> SEQ ID NO 12
<211> LENGTH: 220
<212> TYPE: PRT
<213> ORGANISM: Ecteinascidia turbinata hologenome

<400> SEQUENCE: 12

Met Ile Asn His Ile Gln Ile Asn Glu Asn Ile Leu Gln Tyr Ile Arg
1               5                   10                  15

Asn Thr Ser Leu Arg Glu Ser His Thr Leu Lys Lys Leu Arg Tyr Ile
            20                  25                  30

Thr Asn Lys Leu Pro Glu Arg Asn Met Gln Ile Phe Pro Glu Gln Ala
        35                  40                  45

Gln Phe Ile Ser Leu Leu Ile Lys Leu Met Lys Ala Lys Met Ala Leu
    50                  55                  60

Glu Ile Gly Val Phe Thr Gly Tyr Ser Ser Ile Cys Ile Ala Lys Ser
65                  70                  75                  80

Leu Pro Glu Asn Gly Lys Leu Ile Ala Cys Asp Asn Asn Ile Lys Trp
                85                  90                  95

Thr Asp Ile Ala Lys Lys Phe Trp Lys Ile Glu Lys Ile Asn His Lys
            100                 105                 110

Ile Ser Leu His Ile Asn Asp Ala Leu Leu Thr Leu Lys Lys Leu Leu
        115                 120                 125

Leu His Lys Lys Glu Tyr Phe Asp Phe Ile Phe Ile Asp Ala Asp Lys
    130                 135                 140

Glu Asn Tyr Ile Asn Tyr Tyr Glu Tyr Ser Leu Lys Leu Leu Lys Ala
145                 150                 155                 160

Gly Gly Leu Ile Leu Phe Asp Asn Thr Leu Trp Ser Gly Lys Val Thr
                165                 170                 175

Val Ser Gln Asn Ile Lys Tyr Asn Ala Asp Thr Lys Ile Ile Asn Asp
            180                 185                 190

Leu Asn Asn Phe Leu Leu Ser Asp Asn Arg Val Glu Ile Ser Leu Leu
        195                 200                 205

Pro Phe Ala Asp Gly Ile Thr Leu Ala Leu Lys Lys
    210                 215                 220


<210> SEQ ID NO 13
<211> LENGTH: 486
<212> TYPE: PRT
```

<213> ORGANISM: Ecteinascidia turbinata hologenome

<400> SEQUENCE: 13

```
Met Ile Lys Trp Asn Ile Ala Ile Gly Leu Glu Val His Ile Gln Leu
1               5                   10                  15

Ser Thr Glu Ser Lys Ile Phe Ser Lys Ala Lys Asn Gln Tyr Gly Asn
            20                  25                  30

Ala Pro Asn Thr Gln Val Ser Gly Ile Asp Leu Gly Leu Pro Gly Thr
        35                  40                  45

Leu Pro Ile Leu Asn Lys Arg Ala Ile Glu Phe Ala Ile Arg Leu Gly
    50                  55                  60

Leu Ala Ile Asn Ala Lys Ile Pro Thr Tyr Phe Leu Phe Val Arg Lys
65                  70                  75                  80

Asn Tyr Phe Tyr Pro Asp Leu Ser Lys Gly Tyr Gln Ile Ser Gln Asn
                85                  90                  95

Lys Ile Pro Ile Leu Met Gly Gly Tyr Ile Pro Ile Ala Ile Asn Asp
            100                 105                 110

Ser Lys Lys Tyr Ile Lys Lys Ile Phe Ile His His Ala His Leu Glu
        115                 120                 125

Glu Asp Ala Gly Lys Leu Val His Thr Lys Lys Asn Ala Gln Ile Asp
    130                 135                 140

Phe Asn Arg Ser Gly Asn Pro Leu Leu Glu Val Val Thr Lys Pro Asn
145                 150                 155                 160

Ile Thr Ser Ala Lys Glu Ala Ile Ser Phe Leu Lys Glu Leu His Leu
                165                 170                 175

Leu Val Arg Tyr Leu Lys Ile Ser His Ala Asn Met Glu Lys Gly Glu
            180                 185                 190

Phe Arg Cys Asp Val Asn Ile Ser Val Ser Pro Leu Gly Ser Ser Ile
        195                 200                 205

Leu Gly Thr Lys Thr Glu Cys Lys Asn Leu Asn Ser Phe Lys Phe Ile
    210                 215                 220

Glu Lys Ser Ile Ile Phe Glu Ser Lys Arg Gln Ile Ala Leu Leu Glu
225                 230                 235                 240

Ser Gly Lys Phe Ile Ile Gln Glu Thr Arg Leu Phe Asp Ser Lys Lys
                245                 250                 255

Asn Ile Thr Lys Lys Met Arg Ile Lys Glu His Glu His Asp Tyr Arg
            260                 265                 270

Tyr Phe Pro Glu Pro Asp Leu Leu Pro Val Lys Ile Thr Tyr Ser Tyr
        275                 280                 285

Ile Lys Lys Ile His Leu Leu Leu Pro Glu Leu Pro Asn Ser Ile Arg
    290                 295                 300

Asn Arg Leu Lys Leu Glu His Tyr Leu Asp Lys Lys Glu Ile Glu Met
305                 310                 315                 320

Phe Leu Glu Asn Pro Gln Leu Leu Asn Phe Tyr Glu Lys Leu Val Phe
                325                 330                 335

Ser Val Gly Leu Glu Asn Ser Gln Leu Ala Ser Asn Trp Ile Thr Ser
            340                 345                 350

Met Leu Leu Ser Lys Leu Lys Lys Tyr Lys Leu Ser Ile Ile Asp Ser
        355                 360                 365

Pro Ile Lys Ile His His Leu Ser Asn Ile Ile Phe Lys Ile Lys Lys
    370                 375                 380

Lys Leu Leu Ser Asn Lys Thr Ala Lys Ile Val Phe Asp Asn Leu Trp
385                 390                 395                 400
```

-continued

Ile Thr Asn Gly Lys Ser His Ile Asp Asp Ile Ile His Lys Lys Lys
                405                 410                 415

Leu Leu Gln Ile Asn Asp Ile Asn Ile Ile Glu Lys Thr Val Asn Glu
            420                 425                 430

Val Ile Asp Ser Phe Pro Lys Glu Ile Ile Lys Tyr His Asn Gly Lys
        435                 440                 445

Thr Lys Ile Leu Asp Phe Leu Phe Gly Lys Ile Ile Gln Lys Asn Lys
    450                 455                 460

Lys Ala Asn Pro Lys Lys Ile Lys Glu Ile Leu Ile Gln Lys Leu Phe
465                 470                 475                 480

Leu Lys Lys Asn Ala Asn
                485

<210> SEQ ID NO 14
<211> LENGTH: 393
<212> TYPE: PRT
<213> ORGANISM: Ecteinascidia turbinata hologenome

<400> SEQUENCE: 14

Met Leu Lys Asn Phe Ile Ser Pro Tyr Asp Ala His Ile Val Lys Leu
1               5                   10                  15

Cys Lys Lys Ser Gly Leu Val Leu Leu Gly Lys Thr Asn Leu Asp Glu
            20                  25                  30

Phe Ala Met Gly Ser Ser Asn Glu Ser Ser Tyr Phe Gly Pro Cys Lys
        35                  40                  45

Asn Pro Trp Asp Leu Ser Arg Ile Pro Gly Gly Ser Ser Gly Gly Ser
    50                  55                  60

Ala Ala Ala Ile Ser Ala Asn Leu Thr Pro Ile Ala Thr Gly Thr Asp
65                  70                  75                  80

Thr Gly Gly Ser Ile Arg Gln Pro Ala Ser Met Cys Asn Ile Thr Gly
                85                  90                  95

Leu Lys Pro Thr Tyr Gly Leu Val Ser Arg Tyr Gly Ile Ile Ala Tyr
            100                 105                 110

Ala Ser Ser Leu Asp Gln Ala Gly Pro Met Gly Asn Ser Ala Glu Asp
        115                 120                 125

Cys Ala Leu Leu Leu Asn Ile Ile Ser Gly Tyr Asp Lys Lys Asp Ser
    130                 135                 140

Thr Ser Ser Phe Ala His Lys Lys Asp Phe Thr Lys Ile Leu Asn Asn
145                 150                 155                 160

Ser Ile Lys Gly Ile Lys Ile Gly Ile Pro Glu Asp Tyr Phe Ser Lys
                165                 170                 175

Gly Leu Asp Pro Lys Ile Glu Leu Thr Ile Gln His Ala Leu Lys Lys
            180                 185                 190

Tyr Glu Ser Met Gly Ala Lys Leu Lys Ser Ile Arg Met Lys His Asn
        195                 200                 205

Asp Ile Cys Ile Ser Ala Tyr Tyr Ile Ile Ala Gln Ala Glu Ala Ser
    210                 215                 220

Ser Asn Leu Ala Lys Tyr Asp Gly Ile Arg Phe Gly Tyr Arg Cys Gln
225                 230                 235                 240

Asn Pro Lys Asn Leu Trp Asp Leu Tyr Glu Arg Ser Arg Gly Glu Gly
                245                 250                 255

Phe Gly Glu Ile Val Lys Gln Arg Ile Leu Ala Gly Thr Phe Met Leu
            260                 265                 270

Ser Ser Glu Phe Tyr Asn Ser Tyr Tyr Ile Lys Ala Gln Lys Ile Arg
        275                 280                 285

```
Arg Leu Ile Phe Gln Asp Phe Gln Lys Ala Phe Glu Lys Val Asp Val
    290                 295                 300

Ile Met Gly Pro Thr Ser Pro Ile Leu Pro Tyr Lys Ile Gly Lys Asn
305                 310                 315                 320

Lys Asn Asp Leu Ser Leu Leu Tyr Leu Ser Asp Met Tyr Thr Leu Ala
                325                 330                 335

Leu Asn Met Ala Gly Leu Pro Gly Ile Thr Ile Pro Ala Gly Phe Val
            340                 345                 350

Lys Lys Leu Pro Ile Gly Leu Gln Ile Ile Ser Pro Ala Phe Thr Glu
        355                 360                 365

Glu Lys Leu Leu Asn Ile Ala His Gln Phe Gln Leu Asn Thr Asp Trp
    370                 375                 380

His Met Gln Lys Pro Gln Asn Ile Leu
385                 390


<210> SEQ ID NO 15
<211> LENGTH: 102
<212> TYPE: PRT
<213> ORGANISM: Ecteinascidia turbinata hologenome

<400> SEQUENCE: 15

Met Tyr Lys Met Tyr Leu Thr Thr Glu Glu Ile Lys Lys Leu Ser Lys
1               5                   10                  15

Lys Ser Cys Leu Lys Ile Asp Asn Lys Glu Ile Leu Gln Thr Lys Lys
            20                  25                  30

Gln Leu Asp Ile Cys Leu Asn Val Met Asn Lys Ile Ser Leu Ile Asn
        35                  40                  45

Thr Asn Asn Ile Lys Pro Leu Tyr Asn Ile Ser Asn Lys Thr Gln Ile
    50                  55                  60

Leu Gln Glu Asp Ser Pro Ile Lys Lys Asp Phe Asp Asn Lys Tyr Ile
65                  70                  75                  80

Leu Lys Asn Ala Pro Ser Ile Asp His Glu Asn Lys Leu Phe Leu Val
                85                  90                  95

Pro Thr Phe Leu Ser Lys
            100


<210> SEQ ID NO 16
<211> LENGTH: 497
<212> TYPE: PRT
<213> ORGANISM: Ecteinascidia turbinata hologenome

<400> SEQUENCE: 16

Met Tyr Asn Lys Phe Glu Val Ile Ile Ile Gly Ala Gly Pro Ser Gly
1               5                   10                  15

Leu Met Leu Ser Ile Glu Leu Ala Leu Arg Asn Ile Ser Cys Ala Ile
            20                  25                  30

Ile Glu Lys Arg Lys Ser Arg Leu Ile Glu Thr Arg Ala Phe Gly Leu
        35                  40                  45

Met Pro Leu Thr Leu Asn Leu Leu Asp Met Arg Gly Leu Ala Asn Ser
    50                  55                  60

Met Ile Ser Glu Gly Ile Ile Cys Asn Tyr Ala Pro Leu Gly Asp Gly
65                  70                  75                  80

Lys Gly Lys Leu Tyr Phe His Ser Leu Lys Thr Lys Phe Pro Phe Leu
                85                  90                  95

Leu Ser Ile Pro Gln Glu Lys Thr Glu Glu Ile Leu Glu Lys Arg Thr
            100                 105                 110
```

```
Ile Gln Leu Gly Val Lys Ile Phe Asn Asn His Glu Leu Leu Arg Phe
        115                 120                 125

Glu Glu Lys Asn Gly Asp Phe Leu Leu Phe Cys Lys Asn Lys Lys Glu
    130                 135                 140

Glu Asn Ile Phe Ile Ser Arg Tyr Leu Ile Gly Cys Asp Gly Ser Tyr
145                 150                 155                 160

Ser Ser Val Arg Asn Leu Ala Lys Ile Pro Phe Thr Phe Leu Lys Gln
                165                 170                 175

Asn Lys Thr Leu Met His Gly Asp Val Tyr Leu Lys Tyr Pro Pro Lys
            180                 185                 190

Asp Lys Ile Phe Ala Lys Thr Ser Lys Arg Gly Met Ile Ala Ile Phe
        195                 200                 205

Pro His Lys Asn Gly Ser Tyr Arg Ala Ile Ala Leu Asp Gln Lys Lys
    210                 215                 220

Met Leu Ile Pro Val Asn Thr Lys Leu Thr Leu Glu Asp Phe Thr Glu
225                 230                 235                 240

Ser Leu Thr Ser Leu Ser Gly Gly Cys Asn Phe Gly Ile Asn Asn Phe
                245                 250                 255

Ile Trp Leu Lys Arg Phe Arg Val Gln Gln Lys Gln Ser Gln Ser Tyr
            260                 265                 270

Gln Lys Gly Lys Ile Phe Leu Leu Gly Asp Ala Ala His Thr His Met
        275                 280                 285

Pro Ala Gly Gly Gln Gly Leu Gln Val Ala Ile His Asp Ala Phe Asn
    290                 295                 300

Leu Gly Trp Lys Leu Ala Phe Tyr Ile Lys Lys Lys Ser Ser Tyr Asn
305                 310                 315                 320

Leu Leu Ser Ser Tyr Thr Glu Glu Arg Arg Lys Ile Asn Glu Ile Ala
                325                 330                 335

Met Lys Arg Ser Ser Met Leu Phe Lys Tyr Glu Ile Ala Asn Asp Ile
            340                 345                 350

Phe Ser Met Ser Leu Lys Trp Thr Ile Asn Lys Leu Phe Ser Phe Lys
        355                 360                 365

Phe Met Gln Lys Tyr Phe Ala Lys Asp Met Ser Gly Leu Ser Thr Asn
    370                 375                 380

Tyr His Lys Ile Phe Ser Lys Lys Lys Asn Tyr Lys Lys Phe Lys Cys
385                 390                 395                 400

Leu Gly Tyr Phe Ile Arg Asp Ile Lys Ile Tyr Thr His Asp Asn Thr
                405                 410                 415

Leu Arg Phe Leu Tyr Ser Phe Leu Lys Gln Gly Lys Phe Val Phe Ile
            420                 425                 430

Ser Ile Met His Gln Ile Ser Phe Ile Ser Trp Lys Asn Thr Asp Ile
        435                 440                 445

Ile Phe Leu Ala Ser Asp Asp Ile Lys Lys Ile Tyr Gly Ile Asn Cys
    450                 455                 460

Cys Leu Val Arg Pro Asp Gly Ile Ile Cys Trp Ala Gly Leu Asp Thr
465                 470                 475                 480

Lys Lys Phe Thr Lys Asn Ile Phe Tyr Glu Ile Ile Phe Leu Lys Gln
                485                 490                 495

Glu
```

<210> SEQ ID NO 17
<211> LENGTH: 668
<212> TYPE: PRT

<213> ORGANISM: Ecteinascidia turbinata hologenome

<400> SEQUENCE: 17

```
Met Asn Ser Ile Ser Ser Ile Tyr Leu Lys Asn Asn Lys Ile Leu Thr
1               5                   10                  15

Glu Lys Ile Ile Lys Lys Cys Met Leu Ile Arg Leu Val Glu Glu Arg
            20                  25                  30

Leu Leu Gln Ala Phe Ser Glu Gly Glu Leu Tyr Gly Thr Ile His Thr
        35                  40                  45

Cys Ile Gly Gln Glu Leu Ile Gly Val Met Ala Cys Gln Phe Ile Asn
    50                  55                  60

Gln Thr Asp Thr Ile Phe Ser Asn His Arg Cys His Gly His Phe Leu
65                  70                  75                  80

Ser Phe Thr Asn Asp Val Glu Gly Leu Ile Ser Glu Ile Tyr Gly Lys
                85                  90                  95

Lys Thr Gly Val Cys Ser Gly Ile Gly Gly Ser Gln His Leu Tyr Lys
            100                 105                 110

Asn Asn Phe Tyr Ser Asn Gly Ile Gln Gly Gly Phe Met Pro Val Ala
        115                 120                 125

Ala Gly Leu Ala Tyr Ser Phe Lys Glu Asn Asn Lys Ile Ala Ile Ile
    130                 135                 140

Phe Ile Gly Asp Gly Thr Leu Gly Glu Gly Ile Leu Tyr Glu Thr Tyr
145                 150                 155                 160

Asn Ile Ile Ala Leu Leu Lys Leu Pro Leu Leu Ile Ile Leu Glu Asn
                165                 170                 175

Asn Leu Tyr Ala Gln Ser Thr His Gln Lys Glu Thr Leu Ser Gly Asp
            180                 185                 190

Ile Leu Lys Arg Ala Gln Ala Phe Asn Ile Tyr Ala Asp Lys Ser Asp
        195                 200                 205

Ile Trp Asn Trp Asn Ser Leu Tyr Lys Lys Met Glu Phe Met Ile Asn
    210                 215                 220

Tyr Val Arg His Tyr Arg Ser Pro Ala Phe Leu Glu Val Ser Cys Tyr
225                 230                 235                 240

Arg Leu Lys Ala His Ser Lys Gly Asp Asp Asp Arg Asp Glu Asn Glu
                245                 250                 255

Ile Asn Phe Tyr Lys Lys Lys Asp Pro Val Lys Ile Ile Met Asp Gln
            260                 265                 270

Ile Phe His Lys Leu Gln Lys Lys Ser Ile Ile Ser Leu Ile Lys Glu
        275                 280                 285

Arg Ile Glu Asn Ala Ile Tyr Lys Ala Lys Lys Asp Val Tyr Ala Asn
    290                 295                 300

Tyr Lys Ile Tyr Gln Tyr Lys Asn Tyr Asn Ile Phe Asn Asn Tyr Gln
305                 310                 315                 320

Asn Leu Tyr Val His Cys Lys Lys Asn Lys Arg Ile Ser Thr Leu Leu
                325                 330                 335

Asn Asn Thr Leu His Asn Leu Met Lys Glu Asn Ser Asn Ile Ile Leu
            340                 345                 350

Leu Gly Glu Asp Ile Lys Asp Pro Tyr Gly Gly Ala Phe Lys Ile Thr
        355                 360                 365

Lys Gly Leu Ser Ser Lys Phe Pro Asp Arg Val Ile Asn Thr Pro Ile
    370                 375                 380

Ser Glu Ala Ala Ile Val Gly Phe Ser Cys Gly Met Ser Leu Ser Gly
385                 390                 395                 400
```

```
Leu Leu Pro Ile Val Glu Ile Met Phe Gly Asp Phe Ile Thr Leu Ala
                405                 410                 415

Phe Asp Gln Ile Leu Asn His Ala Ser Lys Leu Lys Tyr Met Tyr Asn
            420                 425                 430

Tyr Asn Val Ser Thr Pro Ile Ile Ile Arg Thr Pro Met Gly Gly Gly
        435                 440                 445

Arg Gly Tyr Gly Pro Thr His Ser Gln Thr Leu Glu Lys His Phe Leu
    450                 455                 460

Gly Ile Pro Gly Ile Arg Ile Phe Ala Ile Asn Asn Leu Phe Asn Pro
465                 470                 475                 480

Glu Ile Leu Tyr Lys Ser Ile Leu Lys Asn Asn Gln Glu Leu Ser Ile
                485                 490                 495

Ile Ile Glu Asn Lys Ile Leu Tyr Thr Lys Asn Leu Leu Ser Phe Pro
            500                 505                 510

Leu Lys Gly Tyr Phe Tyr Lys Phe Lys Asp Tyr Pro Gln Pro Thr Ile
        515                 520                 525

Met Met Leu Pro Lys Ser Asn Leu Ile Asp Ile Thr Leu Ile Thr Tyr
    530                 535                 540

Gly Gly Leu Val Asp Ile Ile Val Glu Ile Ile Glu Glu Leu Phe Glu
545                 550                 555                 560

Glu His Asp Leu Ile Ala Gln Leu Ile Cys Pro Ile Gln Ile Tyr Pro
                565                 570                 575

Cys Gln Leu Ser Glu Phe Ser Asn Leu Ile Lys Lys Ser Ser Leu Ile
            580                 585                 590

Val Leu Ile Glu Glu Gly Gln Gly Phe Ala Asn Phe Ser Ser Glu Met
        595                 600                 605

Leu Ser Gln Leu Ile Glu Asn Asp Lys Phe Lys Asn Cys Asn Phe Leu
    610                 615                 620

Arg Cys Ser Ser Glu Pro Ser Pro Ile Pro Ala Ser Ile Tyr Leu Glu
625                 630                 635                 640

Asp Lys Met Leu Pro Asn Lys Thr Asn Ile Leu Arg Asn Ile Leu Glu
                645                 650                 655

Ile Tyr Asn Glu Lys Lys Asn Val Asn Ser Lys Ile
            660                 665
```

```
<210> SEQ ID NO 18
<211> LENGTH: 365
<212> TYPE: PRT
<213> ORGANISM: Ecteinascidia turbinata hologenome

<400> SEQUENCE: 18

Met Lys Lys Lys Met Leu Ile Pro Arg Phe Glu Ala Asn Asp Asn Ser
1               5                   10                  15

Val Lys Ile Ile Glu Trp Leu Val Asn Asp Arg Val Phe Ile Lys Lys
            20                  25                  30

Asn Thr Pro Leu Leu Asn Ile Glu Thr Ser Lys Thr Phe Gln Glu Ile
        35                  40                  45

Lys Ser Lys Tyr Asp Gly Phe Ile Lys Lys Met Cys Gln Glu Gly Asp
    50                  55                  60

Thr Leu His Thr Gly Asp Ile Phe Ile Glu Phe Tyr Thr Lys Leu Glu
65                  70                  75                  80

Asp Leu Leu Lys Lys Asn Thr Tyr Phe Lys Lys Lys Lys Asp Thr Val
                85                  90                  95

Leu Ser Cys Lys Ser Thr Tyr Gln Arg Phe Ser Lys Lys Ala Lys Lys
            100                 105                 110
```

```
Ile Leu Leu Glu Lys Asn Ile Asp Ile Ser Ser Cys Thr Glu Glu Leu
        115                 120                 125

Ile Thr Thr Lys Val Leu Asn Asn Ile Thr Asn Glu Ile Arg Lys Asp
    130                 135                 140

Lys Lys Asn Lys Asp Leu Ile Lys Tyr Phe Pro Asn Leu Glu Val Lys
145                 150                 155                 160

Lys Asn Ser Asp Ile Lys Asn Arg Glu Ile Ser Val Leu Glu Lys Ser
                165                 170                 175

Asp Gly Asn Ile Phe Ser Ser Ser Ile Met Ile Gln Leu Ser Ser Glu
            180                 185                 190

Lys Ile Arg Glu Asn Ile Lys Lys Ile Pro Lys Leu Asn Gly Gln Ile
        195                 200                 205

Phe Pro Tyr Leu Met Tyr Phe Tyr Ile Gln Glu Leu Ser Ile Ser Pro
    210                 215                 220

Lys Phe Thr Ala Phe Tyr Arg Glu Lys Asn Ile Ile Tyr Tyr Asn Arg
225                 230                 235                 240

Ile Asn Leu Gly Ile Leu Ile Asp Asn Asn Asn Ile Leu Gln Ile Ile
                245                 250                 255

Val Leu Lys Asp Ala Asn Lys Phe Ser Leu Leu Glu Leu Gln Asn Glu
            260                 265                 270

Leu Ile Asp Lys Ile Cys Arg Cys Tyr Glu Asn Asn Leu Glu Ile Asp
        275                 280                 285

Asp Val Val His Ser Thr Thr Ser Val Ser Asp Leu Ser Gly Asn Asn
    290                 295                 300

Ile Ile Ser Phe Gln Pro Ile Ile Asn Gln Lys Gln Ser Val Ile Leu
305                 310                 315                 320

Gly Ile Gly Gly Asp Thr Asn Leu Leu Gly Lys Pro Ile Thr Phe Asn
                325                 330                 335

Ile Val Phe Asp His Arg Ile Leu Asn Gly Lys Glu Val Ala Ile Phe
            340                 345                 350

Leu Glu Asn Phe Lys Arg Lys Ile Leu Gln Gly Ile Tyr
        355                 360                 365


<210> SEQ ID NO 19
<211> LENGTH: 268
<212> TYPE: PRT
<213> ORGANISM: Ecteinascidia turbinata hologenome

<400> SEQUENCE: 19

Met Gln Arg Tyr Arg Phe Tyr Arg Glu His Lys Phe Ile Ile Pro Leu
1               5                   10                  15

Ile Asn Asp Ile Thr Arg Lys Ile Ala Ser Thr Asn Phe Gln Asn Asn
            20                  25                  30

Lys Glu Ile Ser Leu Leu Ile Lys Lys Leu Ser Asn Leu Gln Leu Val
        35                  40                  45

Leu Thr Lys Tyr Ser Glu His Glu Asp Lys Ala Tyr His Ser Leu Leu
    50                  55                  60

Val Asn Lys Gly Ser Asn Ile His Tyr Asp Leu Glu Asn Asp His Asn
65                  70                  75                  80

Asp Tyr Glu Lys Lys Phe Cys Asp Leu Lys Asn Leu Leu Lys Ile Ile
                85                  90                  95

Lys Asp Leu Lys Asn Lys Lys Glu Lys Ile Ala Tyr Gly Tyr Lys Phe
            100                 105                 110

Tyr Leu Asn Phe Arg Glu Phe Glu Val Lys Asn Ala Ile His Met Asn
```

```
        115                 120                 125

Asn Glu Glu Leu Tyr Ile Met Pro Lys Leu Gln Gln Leu Tyr Ser Asp
    130                 135                 140

Asn Glu Leu Gln Ala Ile Glu Leu Lys Thr Tyr Lys Leu Met Lys Val
145                 150                 155                 160

Ser Glu Ile Ile His Met Met Lys Thr Ile Phe Ile Tyr Met Asp Ala
                165                 170                 175

Asn Asp Arg Leu His Tyr Phe Asn Asp Ile Asn Lys Ser Ser Pro Glu
            180                 185                 190

Lys Thr Lys Pro Ile Leu Cys Ser Ile Leu Lys Ile Lys Lys Asn Asn
        195                 200                 205

Ser Tyr Leu Ile Ser Lys Lys Glu Lys Asp Phe Leu Leu Asn Tyr Phe
    210                 215                 220

Ser Ile Ser Lys Glu Glu Tyr Lys Asn Ile Asn Val Glu Asp Lys Asn
225                 230                 235                 240

Lys Tyr Leu Trp Glu Leu Ser Glu Gly Glu Phe Ile Glu Glu Asn Met
                245                 250                 255

Ser Met Lys Ser Gln His Asp Pro Thr Arg Lys Tyr
            260                 265


<210> SEQ ID NO 20
<211> LENGTH: 113
<212> TYPE: PRT
<213> ORGANISM: Ecteinascidia turbinata hologenome

<400> SEQUENCE: 20

Val Asn Ile Phe Met Leu Lys Asn Asn Phe Leu Leu Leu Pro Pro Glu
1               5                   10                  15

Lys Leu Pro His Ser Gln Lys Glu Leu Ile Ile Leu Gln Asn Ser Lys
            20                  25                  30

Asn Thr Ile Leu Leu Lys Asn Ser Phe Ser Glu Ile Ile His Lys Asn
        35                  40                  45

Asp Leu Phe Ile Ile Ile Gln Lys Ile Leu Lys Ser Tyr Glu Lys Lys
    50                  55                  60

Ile Lys Asn Phe Ser Ile Ile Ser Asn Asp Cys Tyr Glu Ser Lys Lys
65                  70                  75                  80

Asn His Asp Asn Asp Leu Ala Phe Arg Ile Ile Arg Val Asp Gly Pro
                85                  90                  95

Ile Leu Glu Val Leu Asn Tyr Ser Val Ile Lys Thr Tyr His Leu Leu
            100                 105                 110

Phe


<210> SEQ ID NO 21
<211> LENGTH: 134
<212> TYPE: PRT
<213> ORGANISM: Ecteinascidia turbinata hologenome

<400> SEQUENCE: 21

Met Leu Thr Lys Thr Glu Leu Leu Asn Met Ser Lys Asp Ser Tyr Met
1               5                   10                  15

Asn Gln Lys Gln Tyr Glu Phe Phe Glu Lys Ile Leu Cys Gln Gln Lys
            20                  25                  30

Lys Asp Leu Ile Leu Ser Ile Ser Glu Thr Arg Lys Arg Leu Ser Glu
        35                  40                  45

Asn Glu Asn Ser Ser Asp Ile Ser Asp Leu Ala Thr Lys Gln Glu Met
    50                  55                  60
```

```
Gln Gln Ile Phe Leu Lys Thr Val Glu Arg Gln Ser Lys Leu Leu Gln
65                  70                  75                  80

Lys Val Gln Lys Ser Ile Glu Asn Ile Lys Asn Gly Thr Tyr Gly Tyr
                85                  90                  95

Cys Gln Glu Thr Gly Glu Pro Ile Gly Ile Lys Arg Leu Leu Ala Arg
            100                 105                 110

Pro Thr Ala Thr Leu Ser Ile Gln Ala Lys Glu Ala Lys Glu Arg His
        115                 120                 125

Glu Arg Thr Lys Gly Asn
    130


<210> SEQ ID NO 22
<211> LENGTH: 305
<212> TYPE: PRT
<213> ORGANISM: Ecteinascidia turbinata hologenome

<400> SEQUENCE: 22

Met His Asp Leu Lys Asn Ile Phe Asn Ile Ile His Lys Met Ile Phe
1               5                   10                  15

Leu Phe Phe Lys Asn Ile Ile Ala Tyr Ile Ala Leu Val Cys Val Ile
            20                  25                  30

Ile Met Trp Ser Leu Ser Tyr Val Gly Ile Lys Asp Thr Leu Asn Tyr
        35                  40                  45

Phe His Pro Glu Ser Ile Gly Phe Leu Arg Phe Phe Phe Ala Ser Leu
    50                  55                  60

Phe Ile Phe Pro Trp Tyr Phe Phe Leu Ile Pro Lys Lys Tyr Val Leu
65                  70                  75                  80

Gln Gln Tyr Asp Ile Phe Leu Leu Leu Ile Thr Gly Ser Ile Gly Ile
                85                  90                  95

Gly Met Tyr Thr Ile Leu Ile Asn Leu Gly Glu Lys Thr Val Asp Pro
            100                 105                 110

Thr Ile Thr Ser Phe Ile Ile Ser Leu Ile Pro Ile Phe Val Ser Ile
        115                 120                 125

Ile Thr Phe Phe Phe Leu Asn Glu Lys Ile Asn Thr Met Gly Trp Ile
    130                 135                 140

Gly Ile Phe Ile Ser Leu Val Gly Ile Thr Met Ile Phe Ile Gln Ser
145                 150                 155                 160

Lys Ser Ile Asn Tyr Gly Val Ile Tyr Leu Cys Phe Ser Ala Leu Cys
                165                 170                 175

Gly Ala Phe Tyr Thr Ile Met Gln Lys Pro Leu Leu Lys Lys Leu Ser
            180                 185                 190

Pro Leu Glu Ile Thr Ser Trp Cys Ile Trp Phe Ala Thr Ile Ala Met
        195                 200                 205

Ser Phe Ser Ala Pro Ile Ala Ile Lys Glu Ile Tyr Tyr Ala Pro Lys
    210                 215                 220

Thr Glu Leu Ile Ser Ile Ile Leu Leu Gly Ile Gly Pro Gly Ala Leu
225                 230                 235                 240

Ala Tyr Thr Leu Trp Ser Phe Cys Leu Asn His Leu Gln Arg Arg Val
                245                 250                 255

Val Ala Asn Ser Leu Tyr Phe Val Pro Phe Leu Ser Ile Ile Phe Glu
            260                 265                 270

Trp Ile Phe Leu Lys Lys Ile Pro Ser Trp Lys Asn Leu Leu Gly Gly
        275                 280                 285

Ile Ile Ile Leu Phe Gly Val Ile Val Ile Phe Tyr Lys Asn Lys Asn
```

```
    290                 295                 300

Lys
305


<210> SEQ ID NO 23
<211> LENGTH: 481
<212> TYPE: PRT
<213> ORGANISM: Ecteinascidia turbinata hologenome

<400> SEQUENCE: 23

Met Asp Ile Leu Gln Asn Ala Lys Glu Val Leu Leu Phe Ser Asn Asn
1               5                   10                  15

Leu Thr Glu Asn Asp Ile Gln Lys Glu Ile Asn Ile Ala Met Ser Tyr
            20                  25                  30

Asn Ile Asp Phe Ile Asp Leu Tyr Leu Glu Lys Ser Glu Thr Glu Asn
        35                  40                  45

Trp Ile Leu Asp Asp Arg Ile Ile Lys Thr Gly Tyr Tyr Asn Ile Ser
    50                  55                  60

Gln Gly Leu Gly Val Arg Thr Phe Leu Gly Glu Thr Arg Gly Tyr Ser
65                  70                  75                  80

Tyr Ala Asp Ile Ile Asn Ile Asn Ser Leu Lys Glu Ser Ile Lys Lys
                85                  90                  95

Ala Lys Asn Ile Ser Ser Phe Arg Lys Asn Ile Lys Leu Asn Tyr Phe
            100                 105                 110

Asn Asn Ile Lys Lys Asn His Cys Val Tyr Ile Ser Lys Asn Pro Ile
        115                 120                 125

Glu Glu Tyr Lys Gln Phe Gln Lys Ile Ser Phe Leu Lys Glu Ile Asp
    130                 135                 140

Lys Tyr Ile Arg Glu Lys Asn Ala Asn Ile Ile Gln Val Ile Val Gln
145                 150                 155                 160

Leu Tyr Ser Ser Leu Lys Thr Ile Leu Val Ala Ala Ser Asp Gly Thr
                165                 170                 175

Phe Ala Ala Asp Met Arg Pro Met Val Gln Leu Arg Ile Ser Val Ile
            180                 185                 190

Leu Gln Ile Asn Asn Lys Ile Glu Gln Gly Asn Ala Gly Ile Gly Gly
        195                 200                 205

Arg Tyr Ser Tyr Arg Val Leu Phe Asn Pro Lys Asn Trp Lys Lys Ile
    210                 215                 220

Ala Asp Glu Ala Ile Arg Ile Ala Leu Ile Asn Leu Lys Ser Ile Pro
225                 230                 235                 240

Leu Ser Ala Gly Leu Met Pro Val Val Leu Gly Ser Gly Trp Pro Gly
                245                 250                 255

Val Leu Leu His Glu Ala Val Gly His Gly Leu Glu Gly Asp Phe Asn
            260                 265                 270

Arg Lys Gly Val Ser Asn Phe Ser Gln Lys Met Gly Lys Leu Ile Ala
        275                 280                 285

Ser Pro Leu Cys Thr Val Ile Asp Asn Gly Thr Ile Lys Asp Lys Arg
    290                 295                 300

Gly Ser Leu Asn Ile Asp Asp Glu Gly Thr Glu Thr Lys Lys Asn Ile
305                 310                 315                 320

Leu Ile Glu Asn Gly Lys Leu Val Gly Tyr Met Leu Asp Lys His Asn
                325                 330                 335

Ala Phe Leu Met Lys Lys Lys Ser Thr Gly Asn Gly Arg Arg Glu Ser
            340                 345                 350
```

```
Tyr Ala His Ile Pro Met Pro Arg Met Thr Asn Thr Tyr Met Leu Pro
        355                 360                 365

Gly Asn Tyr Glu Leu Gln Glu Met Ile Ser Ser Ile Gln Lys Gly Ile
    370                 375                 380

Phe Ala Val Asn Phe Asn Gly Gly Glu Val Asp Ile Thr Ser Gly Lys
385                 390                 395                 400

Phe Val Phe Val Met Ser Glu Ala Tyr Leu Ile Glu Lys Gly Lys Val
                405                 410                 415

Thr Lys Pro Leu Lys Gly Ala Thr Leu Ile Gly Asp Gly Pro Ser Ile
            420                 425                 430

Met Lys Lys Ile Ser Met Val Gly Asn Asp Leu Ser Phe Asp Leu Gly
        435                 440                 445

Ile Gly Ile Cys Gly Lys Asn Gly Gln Asn Ile Pro Val Gly Val Gly
    450                 455                 460

Gln Pro Ser Leu Lys Ile Asp Glu Ile Asn Ile Gly Gly Thr Lys Ile
465                 470                 475                 480

Lys
```

<210> SEQ ID NO 24
<211> LENGTH: 176
<212> TYPE: PRT
<213> ORGANISM: Ecteinascidia turbinata hologenome

<400> SEQUENCE: 24

```
Met Val Lys Ile Met Ile Arg Ser Arg Asn Ile Phe Leu Ile Gly Met
1               5                   10                  15

Ser Gly Val Gly Lys Ser Thr Ile Gly Lys Gln Leu Ala Asn Glu Leu
            20                  25                  30

Lys Met Val Phe Tyr Asp Ser Asp Glu Ile Ile Glu Lys Arg Cys Gly
        35                  40                  45

Ala Glu Ile Ser Trp Ile Leu Asp Ile Glu Gly Glu Glu Gly Phe Arg
    50                  55                  60

Lys Arg Glu Ser Asp Ile Ile Tyr Glu Phe Thr Glu Lys Lys Gly Ile
65                  70                  75                  80

Val Leu Ala Thr Gly Ser Gly Val Val Leu Lys Lys Ser Asn Cys Asn
                85                  90                  95

Arg Leu Ser Ala Arg Gly Thr Val Ile Tyr Leu Arg Ala Ser Leu Lys
            100                 105                 110

Leu His Val Glu Arg Ser Leu Arg Asp Lys Lys Lys Tyr Leu Ile Gln
        115                 120                 125

Lys Gln Asn Gln Glu Ile Glu Leu Arg Lys Ile Gln Glu Lys Arg Asp
    130                 135                 140

Pro Leu Tyr Asn Arg Ile Ser Asp Ile Ile Ile Asp Ala Asn Ser Ser
145                 150                 155                 160

Ser Ile Arg Ser Ile Val Asn Asn Ile Leu Asp Lys Leu Asn Glu Lys
                165                 170                 175
```

<210> SEQ ID NO 25
<211> LENGTH: 134
<212> TYPE: PRT
<213> ORGANISM: Ecteinascidia turbinata hologenome

<400> SEQUENCE: 25

```
Met Leu Thr Lys Thr Glu Leu Leu Asn Met Ser Lys Asp Ser Tyr Met
1               5                   10                  15

Asn Gln Lys Gln Tyr Glu Phe Phe Glu Lys Ile Leu Cys Gln Gln Lys
```

```
            20                  25                  30

Lys Asp Leu Ile Leu Ser Ile Ser Glu Thr Arg Lys Arg Leu Ser Glu
        35                  40                  45

Asn Glu Asn Ser Ser Asp Ile Ser Asp Leu Ala Thr Lys Gln Glu Met
    50                  55                  60

Gln Gln Ile Phe Leu Lys Thr Val Glu Arg Gln Ser Lys Leu Leu Gln
65                  70                  75                  80

Lys Val Gln Lys Ser Ile Glu Asn Ile Lys Asn Gly Thr Tyr Gly Tyr
                85                  90                  95

Cys Gln Glu Thr Gly Glu Pro Ile Gly Ile Lys Arg Leu Leu Ala Arg
            100                 105                 110

Pro Thr Ala Thr Leu Ser Ile Gln Ala Lys Glu Ala Lys Glu Arg His
        115                 120                 125

Glu Arg Thr Lys Gly Asn
    130


<210> SEQ ID NO 26
<211> LENGTH: 10020
<212> TYPE: DNA
<213> ORGANISM: Ecteinascidia turbinata hologenome

<400> SEQUENCE: 26

agaaataatt tttccaatca tggaatcata atatggtgga atagtatatc cactgtaaat      60

atgcgaatca acacgtatgc ccggccctcc aggtggatga taaatgttta atgttcctgg     120

acttggaaga aatgtttttg gatcttctgc gttaattcta cattgaatag aatgtccttt     180

aatattaata tcattttgat gatatgttat agtttgattg gatgcaattt gtaattgttc     240

tttaactata tctatacctg taacaaattc tgtaactgga tgctctactt gaatacgagt     300

attcatttca ataaaaaaaa attctccttt ttcatataaa aattcaaaag ttccagctcc     360

tcgatacata attttttac aaacttccac acatttttta gcaagatttt cgcaatcttt     420

tctatttaaa gttgaaggag cttcttctaa aactttttga ttacgacgtt gtatagaaca     480

atcacgttct cccaaatgaa ttgcattacc ttttccatct cctaaaactt ggatctcaat     540

atgtcttgga ttttctaaaa atttttccat atatatattt tcatcaccaa aactagcttt     600

tgcttcagtt ttagtcatat caatagaatt agaaagtttt tcagggtcat agactactct     660

aattccaaga ccaccaccac cttttgcagc ttttagaata atcggatatc caattttttt     720

agctaaaatt tgattttttt tagtatcagt atctaatttt cctaatgatc cttctataca     780

agatattccg tgttctttca taatgttaat tgcagaaatt ttatctccca tgtttttcat     840

atttttttata gtaggaccta caaaaataaa accactattt tctactgcag atacaaaatc     900

agaactttct gataaaaatc catatccagg atgaatagaa tcgctatctg ttaattctgc     960

agcactaata atagcaggaa tatttaaata actttttaaa ctattagatg gacctataca    1020

aaccgattca tcggatagtt taacatgttt aagatttctg tcagtagttg aatgaacagc    1080

gacagttttt atttgtaatt ctctgcaagc tcgtaaaatt cttaatgcta tttcaccacg    1140

atttgcaata agtagttttt taatcatatt ttttctctat attataatct attttaaaca    1200

cgctattttt tattttattc aagaataatt aaaggctgat caaattctac aggtgaagaa    1260

tcttcaataa gtattgattt tattattcca gatttatcag attcaatatg attcattgtt    1320

ttcatagctt caattatacc aattacctgt ccaattttaa taacagatcc cacttcaata    1380

aaaggttttg cagtaggtga gggagatcga taaaaagtgc ctaccatagg tgattttatt    1440
```

```
atatttattg aagaataaat atcagaaact ttttttttcct tttttagaaa ttctatagaa   1500

ttagattttt ttaatttttt ttttgtttct ctttcagaag ataaaatatt agatacatct   1560

gattttttag ataattgaat agattcttct ccttgaacta ttttcatatc agataaagaa   1620

aaattatcca ttaattcaag taacttttgt atgtctttat gattaatttt cattattttc   1680

cttttatatt aaaatttaaa atcataagat ataaatatca aaaaaaatat ttaaacattt   1740

tttaacttta ataatatatt aagaccttgc tctcatatat ttttaaatat tttcattaat   1800

ttttaataaa aatataattt ttttaacata atttaaaata tttttttata aaatgatgtt   1860

aaaaataaaa aatatagtta aatcattaaa tgattgccac aaaattatag aatctaatta   1920

acaaaatact ataaaaatgg tgggtactga gggattcgaa cccccggccc tcgccttgta   1980

aggacgatgc tctaccactg agctaagcac cctaacttta ttttattaat tttaatagga   2040

gcaaaaatga tgtcaataat tatatattaa gaattaaaaa atttgaatat taaataattg   2100

gctaaaattg tctgttgttg catgacatat atctgaatat gatagatttt taatttttga   2160

aatacatttg gcaacataat taacataact aggtttatta gattttcctc gaaaaggatg   2220

aggtgttaaa tacggagagt ctgtttcaat taaaatacga tttaaaggaa tttttcgaac   2280

aagatccctt aaatttgcag aatttttaaa cgtcaaaatt ccagaaaaag aaatatacaa   2340

tcccatatct aaaataattt tagccatttc ccatgattca gtaaaacaat gaacaacacc   2400

taaattaacg ttatattttt ctaagatcga tatagtatct tgcgaagcag atcttgtatg   2460

tataattaaa ggtgcattta atttcttaga tgcttgaata tgattaataa atcttttttt   2520

ttgtacaaga atatgttttt cagatttagt tcgataataa tctaatccag attctccaac   2580

agcaataatt ttagagtgtg cattaaaaat atttattaaa tctaaagtag atggttcttt   2640

accttttatt tcgttgggat gttttccaat tgatgcataa atattattaa acttttctgt   2700

aattggtatt attgttttta aattttctat atttaagcat atagaaagaa gatatttgac   2760

atttttatga tatgcttcat caataatatc agctaaattc atttttaatt cttttaaatt   2820

taaaatatct aaatgacaat gtgaatctac taaaattggc attttaaatc ctccatattt   2880

ttaaataaat atatagcata tatatttctt taaaagaaga ttaaaatctt tttttaaaga   2940

taaatttaga gaatcattca ttatataaat accattcaat aaataatcct tcaagaaata   3000

attctgtatt aaataaataa tctattttta taattttttt tctttctact aaataaaagt   3060

caataagata aaaccattga gataaagatt ttttttttgc taatttccaa aaaatagaat   3120

tttttttttt taaaattaat atatatatta aattataaac taattgtatt aaactattta   3180

ttattaatac aagatcaata tcttgaagtt tttttgtttg aaatattggt gttttttttat   3240

ctaaaaaatt ttgaaaaaca gaatttattt tttttaaata tccttttttt ttccaaattt   3300

ctaaataaat aggaccaaat ccagggatat taaaaatatt taataaattt ttagaattat   3360

taatttcata ttcccaaaaa aaatttttta aattttgatt tttttcttct aaaaagaaat   3420

tcatatacca aatttgacat cgactgcgta ttgtaagtgg tatagattct aaataatctg   3480

cagtcaatat taatatagtt ttttctcttt tttcttctaa aattttaaga aatgcattat   3540

acgcaaataa attcatatta tgagatttat ctataataac aacacgatat cctcctatcc   3600

aagatgtcct ttgaagaaaa aaaataatat ttcttatttg atctatttga atttgattta   3660

attttccttg gggttttata tataataaat caggatgttc agataattca ctgctattac   3720

atgaaagaat tttttgagca cacaatttta caaaatgtaa ttttcctgtt cctggaaatc   3780

ctgttaataa tagcccataa ggtattttat tattttgtaa atgccaatta aatttttttcc   3840
```

```
aaagagtttt ttgccaaaaa aatatcataa taattatatt ttcgaaaaat ataaagaaat   3900
tataatcttt atttagaata aaaatataga ttttttattt aaaaaatata ttttaaaatt   3960
ataatatatt ttaaatataa aattaaaaaa tttttttaaa atttaagcac gtaactcaat   4020
tggttagagt atcattatga cataatgaag gttagcagtt caaatctgct cgtgcttacc   4080
ataaattatt atttaatcct caataaaatt gtgaatataa ttctttaaat tagatttaaa   4140
ttgaacaata ttaatgaata aatatatttt tcatttaaaa atgatgaaaa aaaattatag   4200
tattattata ctaataatta tatttgaata aaaatattta ttttgttgta atatatagca   4260
atgaaaatat ttaaaattta tcatgcaaag atatagattt tatagagaac ataaatttat   4320
aattccattg attaatgata taactagaaa aattgcttct actaatttcc aaaacaataa   4380
agaaatctct ttacttataa aaaaactctc taatttgcaa ttagttttaa caaaatattc   4440
agaacatgaa gataaagcat atcattcgtt attagtaaat aaaggatcta atatacatta   4500
tgatctagaa aatgatcata atgattatga aaaaaaattt tgtgatttaa aaaatttatt   4560
aaaaataata aaagatttaa aaaataaaaa agaaaaaatt gcatatggtt ataaatttta   4620
tttaaatttt agagaatttg aagttaaaaa tgctattcat atgaataatg aagaacttta   4680
tattatgcca aaattacaac aattatattc tgataatgaa ttacaagcta ttgaactaaa   4740
aacatataaa cttatgaaag ttagtgaaat cattcatatg atgaaaacta tttttatata   4800
tatggatgca aatgatagat tgcattattt taatgatatt aataaatctt ctccagaaaa   4860
aacaaaacct attttatgta gtattttaaa aataaaaaaa aataactctt atcttatttc   4920
taaaaaagaa aaagattttt tattaaatta tttttctatt tcaaaagaag aatataaaaa   4980
tattaatgta gaagataaaa ataaatattt atgggaatta tcagaagggg aatttataga   5040
agaaaatatg agtatgaaat cacaacatga tcctaccaga aaatattaaa ttcaattttt   5100
ctaaaaaata tataaaaaat aaatggattt ttacttaaaa ttaggagtaa taaatggata   5160
aaaaaatatt aaaaccttgt tatagaagtg attctatatt agatcataac caattgaata   5220
aattgcatga attaactcca attatttttg gagcaagtgc ttttcaatac ttaaatgctg   5280
gatctgaaat aggacttttt gaattattat attattctgg tccaaaaaaa aaatctgaat   5340
taatgataga actcagttta aaagaaagag ctatagatat tttattatta ggaaatacat   5400
ctctaaattt aattaataaa gaaaaatctt tttataaaaa ttctctaata atacaaacaa   5460
tttttgaaaa taatatttgg gatattttca aagatttgat tgcttttgag caatatattg   5520
tttatctggg gcaatttgat tttacagatt ctttaagaaa aaatactaat attggattgc   5580
aaagaatttc taatacatca aacagtcttt ataaaagctt taataaaaat aaaaaattag   5640
aaaaaatatt ctataattat atgaattcat ggacccgtct ttctaattat tatttaatta   5700
aatatattaa ctttaataat gttcatcgtt tacttgatgt tggaggagga acagcaatta   5760
atgctattgc tttagcaaaa aaatatccta aattaaaaat tactgttttt gaaatcgatg   5820
catctgcaaa aatagctcaa aaaaatattc aatcttctgg attatcaaat caaataaatg   5880
tcattcatgg tgatatattt aaagatcaat ttcctactgg atatgattgt gtactttttt   5940
cacatcaatt agttatatgg actcccgaag aaaatataga attattacat aaagcatata   6000
aaattttatc ttcccatgga ttagtaatta tttttaattc tatatctaat gatgatggaa   6060
aaggtccatt attagcagca ctagatagtg tatattttgc tagtattcct tcggaaggag   6120
gcatgattta ttcttggaat caatatgaag aatggttgaa aaaatcaaaa tttcaaaaaa   6180
```

```
tttctcgaat taattgccat cattggacac cacatggaat tataaaagca tataaataaa   6240
ttaagagata ttcaatgaat gaaaaagata cattaaaagg aagctatata ttttctgctt   6300
ctccaggaca agaaaggctc tggtttctta aagaattgaa tagtcaattc ggacctgcat   6360
ataatattcc tgctttattc aaaataaatg gatttcttaa tataatttct ttacaaaaat   6420
ctattaataa aatagtagaa cgtcatgaaa tattaagaac agcattaatt tatgatggaa   6480
caaaattatt gcaagttata aaacctaatt ttttaaaaac tattcgatat gtagattgca   6540
caattaaaga aaaaagaaaa aaatttttag aatcaagttt gatacaagaa tcatctgttc   6600
attttaattt tacacaacca ggaattttcg atttaatttt atataaattt caagaaaaag   6660
tatattatat attaatcaat atacatcata ttattagtga tggtatttca ttagaaattt   6720
ttgtatatga attatttgaa tattattatt ttatagaaaa taaaattaaa attaaaaaaa   6780
aagatttaga aatacaattt gctgattttg taaaatggaa tgaaaaatgg gtttccagct   6840
caaaatattt agaatacgaa ttattttgga aaaaaaaaca aaaagatttt gtattaaatt   6900
taacattacc taaaagaaat agaaatatag atacaattat cggtaataat gtaaattttg   6960
aactttctac ttctattata gatttattaa taaaagaatc aaagaaatta catgtttctt   7020
tatatgcatt ttatctttca atttttgcaa ttcttattta ttttttttca aatcaaaaaa   7080
aatttttaat tggaattcct cttgcaaata gaaaaaatca acaaacacaa aatattatgg   7140
gatttttagc taatacatta gttcttaata ttgctataga tttaaatcaa aatttatcag   7200
attttattaa aaataatcat aaaaatattt taaaacttat caagttagaa cgatttcctt   7260
atagttcttt acataaaatt tcaactaata atatacataa tagcgaacca atttttaaag   7320
ttatgtttgg ttatcaagaa ttagaaaata aaaaatttaa tataaaagaa ttaaatattg   7380
aaagaatcaa ttttaataca attttttcaa aatttgatat ctctcttttt atgtttcaaa   7440
aaggaaaaca acatagagga ttattagaat gtagatccca tatttttagt aaaaaagaaa   7500
gtgaaaattt ttatcgatat ttttctaata tatgcagaat tgcaaaaaat accaatattt   7560
taataaaaaa tattcagttt tatgaaaata atgatattaa atttgcaaaa aacttgttaa   7620
agaatcctga taatttatat cttaataaga aacttttaga aaaagtagta aattttaata   7680
taaaaaataa aaaattttct atattggatg caacgtataa acaagttcct attaatattc   7740
ctggaatatt atttatcaac catcacaata cttatcttaa agtaagactc acttatgata   7800
aaagattaaa tcttattgaa gataatgaaa aagatcaatc taatataata gagaataaat   7860
atcacgattt tataaaagca aattctaaaa ctgaaaaaat tttagaaaat atatggaaga   7920
gtttgctaag attaaattct tcactatcca ttcatcaaag tttttttttct ataggcggcc   7980
attctatttt agttgcgaaa atggtaaata atattaataa aaaattcaat attgtaattt   8040
ccataagaga tatattttttg catcctacaa tatctcatat cgctagtaaa attgaatctc   8100
ttaaagaaaa agaaatccat aatacaaata taaatcctca aaatttaaaa aaagaagata   8160
ttgtagaaat atataaagat attaatggaa aaaaaattta atttaaaata agaggtataa   8220
ttttgaaagg tttagatata aaaatattaa aaaaaaaaat taaatctgga aaaacaaatc   8280
taacacataa tcaacaaaga tgttgttttt ttttaaatat ggattctaat tttccatctt   8340
cagatgcata tttttttgaa gcaaatatat tttttgataa agcaatatta caacaaagta   8400
ttgcttttag cataacaaat tttcctattt ttagatctat ttttattaat atttttggat   8460
ctccaataag aaaaacacaa ttaagttcta ttatttccat aaaattagat aatctttatc   8520
aagataataa taaaattgat aaagtaaaat ggatctctaa taataaaaaa aataatacaa   8580
```

```
ttaatatatc ccaaggacca ttatttaata tattttgctt aaaacattct gataaaaaat   8640
tcaatattct ttttttagtt tcccgattag tttcgaataa aaaattaatt atatctttta   8700
tgaaaaatat atttttttaga tatcaaaatt ttttatatca taatgaaaat gaaaaaatta   8760
tttcatatga aagaaatatt tcagaaaaat tcttttattt agaaaatcaa tggattgaaa   8820
cagaaaattt taaaaatcat attaaatttt ggaaaaaaga agttaaagat ttatctgact   8880
tagatttgca aacagatttt aaaagaccag aaataaaaac aaataaacaa aaatctgttt   8940
ttttaaagtt agaaaaatat aaaattttaa atatttttaa taaaatcaaa aaagaaaaat   9000
ataattatga agaatttttt ttatctatat ttgtaacgat tttatataaa tattctaata   9060
ataataactt tgctatagga cttaaagcta ataaattaga aaaatatttt gataaaaaca   9120
atatttctcc tattgaaaat gaattaccat ttaaaattaa tttaaattct agtttttctt   9180
ttaaaaaaat tctttcaata ataagcaaaa aatataattt atttttaagg tatagcactt   9240
tgcctataaa gattttattg gataaaatag gagtaaatag agatttaaaa aaaacacctt   9300
tttttcaagt atcttttcaa tatgaaaatt tttcttttcc tatttggaat aacaaaaaaa   9360
ataattttct aaaacaaatt cctattttag aaggaattaa tattatggat tttacatttt   9420
gtgcaataga aactaaatcg tcttttatat tacgtatcga ttttaatcca gatctttttt   9480
tagattcatc tatgattttt ttactttctg caatagaaga attattaatg tttatatcaa   9540
ataacagttg ggatatctct attagagatc tatctattat aagcaatatg atgttaaaaa   9600
aaatagaaaa aagatggaat gctcctaaaa aaatattgtt tgaaaatttt gaggttcaca   9660
aaaatttgga aaatcaatgt aaaaaaacac cttcaaatat agctataata tgtcaaggag   9720
aaacaattac ttatagagag ttaaatgaac gagcaaatca aatatcacat tatttaatac   9780
acaaaaaatt attatttaat gaaaaagtag gaattcttat ggatagatca atagaattta   9840
ttatttccat attagcaatc ctaaaaataa attgtattta tgttcctata gatgaaaaat   9900
atcctattga acgtatcaat tatattatta atgatagtca aattaaatta ttaattacaa   9960
aaagttatat tcaaaaaaat aaaaaatataa tatataaaaa tttaatttat ttagataaag  10020
```

<210> SEQ ID NO 27
<211> LENGTH: 4335
<212> TYPE: DNA
<213> ORGANISM: Ecteinascidia turbinata hologenome

<400> SEQUENCE: 27

```
atggattcta attttccatc ttcagatgca tatttttttg aagcaaatat attttttgat     60
aaagcaatat tacaacaaag tattgctttt agcataacaa attttcctat ttttagatct    120
atttttatta atatttttgg atctccaata agaaaaacac aattaagttc tattatttcc    180
ataaaattag ataatcttta tcaagataat aataaaattg ataaagtaaa atggatctct    240
aataataaaa aaaataatac aattaatata tcccaaggac cattatttaa tatattttgc    300
ttaaaacatt ctgataaaaa attcaatatt cttttttttag tttcccgatt agtttcgaat    360
aaaaaattaa ttatatcttt tatgaaaaat atattttttta gatatcaaaa ttttttatat    420
cataatgaaa atgaaaaaat tatttcatat gaaagaaata tttcagaaaa attcttttat    480
ttagaaaatc aatggattga aacagaaaat tttaaaaatc atattaaatt ttggaaaaaa    540
gaagttaaag atttatctga cttagatttg caaacagatt ttaaaagacc agaaataaaa    600
acaaataaac aaaaatctgt ttttttaaag ttagaaaaat ataaaatttt aaatattttt    660
```

-continued

```
aataaaatca aaaaagaaaa atataattat gaagaatttt ttttatctat atttgtaacg    720
attttatata aatattctaa taataataac tttgctatag gacttaaagc taataaatta    780
gaaaaatatt ttgataaaaa caatatttct cctattgaaa atgaattacc atttaaaatt    840
aatttaaatt ctagtttttc ttttaaaaaa attctttcaa taataagcaa aaaatataat    900
ttatttttaa ggtatagcac tttgcctata aagattttat tggataaaat aggagtaaat    960
agagatttaa aaaaaacacc ttttttcaa gtatcttttc aatatgaaaa tttttctttt   1020
cctatttgga ataacaaaaa aaataatttt ctaaaacaaa ttcctatttt agaaggaatt   1080
aatattatgg attttacatt ttgtgcaata gaaactaaat cgtcttttat attacgtatc   1140
gattttaatc cagatctttt tttagattca tctatgattt ttttactttc tgcaatagaa   1200
gaattattaa tgtttatatc aaataacagt tgggatatct ctattagaga tctatctatt   1260
ataagcaata tgatgttaaa aaaaatagaa aaaagatgga atgctcctaa aaaaatattg   1320
tttgaaaatt ttgaggttca caaaaatttt gaaaatcaat gtaaaaaaac accttcaaat   1380
atagctataa tatgtcaagg agaaacaatt acttatagag agttaaatga acgagcaaat   1440
caaatatcac attatttaat acacaaaaaa ttattattta atgaaaaagt aggaattctt   1500
atggatagat caatagaatt tattatttcc atattagcaa tcctaaaaat aaattgtatt   1560
tatgttccta tagatgaaaa atatcctatt gaacgtatca attatattat taatgatagt   1620
caaattaaat tattaattac aaaaagttat attcaaaaaa ataaaaatat aatatataaa   1680
aatttaattt atttagataa agattggcca ttaattgaaa taaaaagtag agaaaattta   1740
aattttagta ctaatatcca aaaaaatggc atgtatatga tttatacctc tggatctaca   1800
ggtcaaccta aaggtgttat tttaaatcat tttggagtat taaataatat tagttggaga   1860
cagaataaat ggaatttaaa tgaaaaagat cgaatattat taaatacatc ttttagtttt   1920
gatccttcca tttggtctat tttttggcca ttacttttg gaggagcatt tattatagtt   1980
cctttatcta tacaaaatga tatttatgaa ttaataaaat taataaaaaa atataatata   2040
tctattattg gaactattcc acatattatt gatttattag tatcaaacat tgctattaga   2100
aattgcaatt ctcttagact tattttaagt ggtggtgaac cattatctca aaaaattgtt   2160
caaaaagttt ttaatcgtac aaatgctaaa ctttttagtt tatatggtcc tactgaaaca   2220
actattgatg caggaattta cgaatgtaaa cccgatgata ttgtgcaaac agcaccaata   2280
ggaaaagcaa ttgataatac aagaatatat attttagatg aaaatttaag acatgtacca   2340
gatggagtaa aaggagaaat ttatatttca ggaccaggtg tagctatagg ctatcataac   2400
agaaaagatt taaatgcaaa atcttttctt aaagataata ttttttattc tgaattaaaa   2460
tatatgtata aaacaggaga tcttggtgta ttttgttatg atgataacat caaattttta   2520
ggaagaattg ataatcaagt taaaatacat ggaaatagga tagaatgttc agaaatagaa   2580
tcggttttaa taaatataaa aaaagttaaa gaaagtgctg taatagtaga caatccttat   2640
actgaaaaaa ctaaattaat tgcttttta gcagtatcag aattagatgt aaaaaaagaa   2700
gatattcaaa aaaaattaaa aaataaactg ccaaaatata tgctgccaga taaaattatt   2760
ttacttatat ctttgccaaa attagaaaat gggaaaattg ataaaaatgc tttatttcga   2820
atctataata catcaaaaaa taataaaagc gcacttttag aaaataaatt acctaataat   2880
cctatagaaa aaatagtatt taaatatttt tgtgatgttt tatctctttc caatattagt   2940
attcatgatg attttttaa attaggtgga acatctatat tattagcaag attatcaaat   3000
ttattattca atcattttga tatttcttta cctcttcatc aattttttaa aattccaacg   3060
```

gttctaggtg tttcaaatat aattgttacc ttgcaaaaag aaggaattga taaagctctg 3120
cttgataagc atatctcaaa acttgaagaa gatgcagagt taataaaaga tatttctcca 3180
aaaaatcttc ctaaaggaaa tttttataat cctaaaaata ttttaattac tggaagtaca 3240
ggatatatag gttcttttat tttacaagaa ttattaatta atactaacgc tactatatat 3300
tgtttgatta ggtctaaaaa tcctgagaaa gctttgataa aattaaagaa taaaatgaaa 3360
gaattttata tttggaaaga agtgtacaca aaaagaatag tttgtttagt tggtgatcta 3420
ggcgaaaaaa atattggatt aaataaaaaa atatgggaaa atctatctaa aaaaatagag 3480
gttatttttc atgctggcgc tttagtaaac tttgcttatc cttattctgc tttaaaagct 3540
gcaaatgtag aaggaacaaa agaaattttt cgattttcat gtaaaaattt attaaaatca 3600
gttcattata tttcaaccat tgatgtgtta ttagctactc atattcctag accttttta 3660 gaaaatgatg ctcctttaaa agtaagtatt gatattcctg gaggatatac tggtagtaaa 3720
tgggttgcag aaaagatagc gcattctgca atgatacgag gcattccaac ttctatatat 3780
cgtcctggac tagttatgag ccattcagaa acaggagcaa ctcaaacaaa tgattatctt 3840
ttggttgcat ttaaaggttt tataccaaaa aaagttattc ctgaatatgc aagaatattt 3900
gatattgttc cagtagactt tgtagctaaa tctatagttt atgcatcaat gcaaaaaaat 3960
gtacacggaa aattctatca tatttttaat ccaaagccta ctactttata tcaattttgc 4020
aattggatta aaaattatgg atattcgttt gatattattc catttgaaat tggtagaaaa 4080
attgcgttag attctaaaga atctgatccc ctttacccgc tagttccatt aattagagat 4140
gcagatccaa atcctcacag acctttagat cctaaatata ttaatgaagt gcaaccagaa 4200
attgaatgta aaaatatgaa cactatttta caaaaaagtg gaattatatg tcctaatatg 4260
aatgaaaaat taacacattt atgtttaaaa tatttaataa atattggata ctttcctcat 4320
ccgaaaaaaa tataa 4335

<210> SEQ ID NO 28
<211> LENGTH: 5373
<212> TYPE: DNA
<213> ORGANISM: Ecteinascidia turbinata hologenome

<400> SEQUENCE: 28
atgaaaaaaa tgattaatta taaagaacat gaaattacaa gttttgtaga tataatttta 60
ttgagaagtc ataccgttcc agataaaaag atgttgacat atttaacatc ttttgatgaa 120
aaaaaagaac tgacttataa aaaaataaat aagatttcac aacaaatagc tgtaaaaatt 180
ttgcattatc tttctcctgg agatagagct ttaatttttc ataaaccaag tattgattat 240
attacagctt tatttggatg tttatatgca ggaataattg ctattcctgt ttatggacca 300
gaacatggaa ttaataaaaa taaattatat agacttaaaa atattataaa agattctggt 360
gcaaaaggaa ttctattatc ttataaagaa ttaaaaaatt gtcaacattt tttttctaat 420
ttttatatac ataaagaaaa aatacattat atcactacag atgatactag taatattgat 480
tttcaagatt ggaaaaaacc gtattttaat aaaaatcata cttctattat tcaatacact 540
tcaggatcaa catctgatcc taaaggagtt atgcttaatc acactaattt aatatccaat 600
atattatcaa ttcaaaatat atttgaaatg aaaaaaaaca aaggaaaagc tgtaatttgg 660
ttgcctccat atcatgatat gggattaata ggaggaattt taacaccaat atttgtagat 720
tttccattaa ttcttatttc accattatta tttattcaaa atcctatatt ttggttaaaa 780

```
ttaattagta tggaaaaagc aacaattact ggaggtccaa attttgcttt tgatttatgc    840
tctaataaag caataataag aaaattaaac aatatagatt tatcatctat aaaacatatt    900
ttttctggtg cagaacctat taatccagaa gtgattaata aatttttcga aatatatgaa    960
aagtttggat tatctaaaaa atcttttagt acttgttatg gccttgctga aagcacttta   1020
atggtaacaa gttctaaaat agaaaataac aaagaaatta aagaaaaaga attctttttt   1080
aagaaaaata ttgtagaagt ttttaaaaaa aaccaaaaat cattttcatt atctaaaaaa   1140
ttattttctt gtggaaaaat tattcccaat cataaattag caatagttga tcctaaaaaa   1200
tctaagaaac taaatgaaaa agtcattgga gaaatatatg tgaaaggtcc atcagtttct   1260
aaaggttatt ggaaaaatcc taaaaaaaca aagaatatat ttcaaaattt ctttataaaa   1320
gaaaataaaa aaaaatctta tggatggtta aaaacaggag atttaggatt cttatacaat   1380
tctcaactat atgttactgg tagaataaaa gatttaatta ttattcgagg agaaaatttt   1440
tatcctcaag atattgaaaa ttatgttaaa gaattaaatt ctaaaattca attatgcaat   1500
tctgcggcat ttgaaattga caaaaatcat ataaaagaag tagttttatt gcaagaaata   1560
agaaaaaaaa atttatctga aaattttgag aatcttgctc ttgatataag aaaatctatt   1620
ttagataaat taaatttatt aattcataat ataattttta tagaaaaagg agcattacca   1680
aaaaccacta gcggtaaaat acaaagattt ttagcaaaaa aatattattt aagtaatagt   1740
tttaatataa tattttcttt taattctcaa ttgaaagaaa aatataaaaa aattaattat   1800
gtccaaaaat actatattca atccttaaag aaagaagaaa aaaaaattta ttattcaata   1860
ataaaattta ttcaaagata tcaaaacctc aataaagata ttattaattt cacaatttta   1920
gaaattggat tagattcatt gcatatgatg gaattaaaaa attttttaga agaaaaatat   1980
aaaattattt taaatatgca ttctttttta gaagatacaa aaatttttac tttagtaaaa   2040
gaagttttta acaaacataa ggaaaatata cagaaaatat atataaaaaa ggaaaagaaa   2100
aaaaatgttt taaaaaatca agtaagtaaa tatttttctg ttgatcctgg aaaatcatca   2160
atttattata attatcttgt acaaaaagaa aattctatat atgaaatttt cagaattatt   2220
aaaatatcta aatctataaa tataaaatta ttagaaaaat ctattcatat attgttaaat   2280
atgtatccaa cattaaaaag tagatttata gtaaaaaata ctggaatagt gtatcaggaa   2340
tatcctgttg aattatcctt ttcttctatt tttagaaaaa taaattgtaa agatatagat   2400
ttaaaagaaa catgtaatat ctttttaaaa gaacgtttta atatggaaaa gggaccactt   2460
tttaatatta tacatataaa taatataaaa cttgattata atattctaat atttaagatt   2520
catcatatta ttgcagattt ttggtcaata attataattt atcaaaatat tgaaaatatt   2580
tataataatt tattaaaaaa taattctatt aagaatataa aaatatatga aacattccaa   2640
gatgtacaaa ataaaaaata taaaaaatac attcaatcta atcaatttat tgaagacaat   2700
ctttttttgga aaagatattt atctaaatat aatttattag aaaatacaaa taatattaag   2760
agaaaaaata ttcaatcatt tcaatttaat ttaaatttta atttttataa caatttatta   2820
attttttcta aaaaaaaaaa aataacacct tataccattt tattaattat ataccaaatt   2880
acatattatc gaatatataa aagagattat tttattactg gaactccagt agcattgcgt   2940
gatgattatc ttttacgaaa ttatatagga tattgtgtaa atattttacc aattgtttca   3000
gatttttcaa aacaaaatga tatatattct tttactgaaa aagttaaaaa tgatattaaa   3060
aatatattac aacataaata tttttatttt tcaaaaatta tagaattatt gaaattgcct   3120
agaaatacgg attatattcc attatttaat agccttttta tttaccaaac agatcatata   3180
```

```
ggatcttttc atttttttaaa tacaattgca gcaaatataa aagatagcga atttcaattt   3240
ttaggatatc cagcatctat atggtataca aataatttta atttaatgca tcattttatt   3300
tttaatattt ctgtaaataa agaatcctat tcaattaata ttgaatacga tgaaaatata   3360
cataataaaa tattaataaa aaaattttct gaacaattta aattaacatt tcaagcaatt   3420
atttttaata aaccaaaagc aattatagaa gaaaaacaat atttgtttta tcaaaatata   3480
aattctacta ataaaaaatt ttttaaatct caatattttt tagatcaatt gtttaggaaa   3540
caagtaatta aaaatccaaa tgcatcagca ataatttttg atgacataaa tattacttat   3600
aaaaaattga ataaatatgt taatagagtt tctcattatt taataaatca tattttaaaa   3660
aatgaaattc ttattgctat tcttatggaa aaaggaatag aacaaatagt tgcatgttta   3720
gctatcctat ccataggaaa agcttattta cctattaata ttaatttttc taaaaataaa   3780
attcatgaaa taatggtatt aggaaaagta aaaagatttt taattcaaaa aaaatattta   3840
aaaaaattta attttaaaga ttttcaatca attgatgtaa catctataat tgaaaattct   3900
tcttttaaaa aatctcaaga atattttcca aagtatcaat taagaaaatt aaatgatctt   3960
gcttatgtaa tttttacatc tggttcaact ggcactccaa aaggtgtaat gattgaacat   4020
aaacaagttg taaatactat tttagatata aatgaaaaat ttcaagttaa taatttagat   4080
agaatattag caatatctaa tttagatttt gatttatcgg tatatgatat tttggaata   4140
ttatctgctg gcggaacatt agttattgtt ccatcaaaat ttacaaaaga accaaaatat   4200
tggttatatg caatacaaaa ataccaaatt actatttgga atagcgttcc tatgtttaaa   4260
caaatgttta ttgaatattt acaaggtata gataaagaga gtttttataa aaaaattaaa   4320
ttaaaattaa ttttattaag tggagattgg attcctctag atttgccaga aaaaatattt   4380
aaaatatata aaaagaattt tgattcttta aaagttgtat ctcttggagg agctacggaa   4440
tgttcaatat ggtctaatta ttttattatt aataaaaata ttaaatataa aactagcatt   4500
ccttatggca aaccattatc taatcaacat ctatatattt tagacgcttt aatgttgcca   4560
acaaatatat tagttccagg ttatttatat ataggtggat ttggagttgc gagaggttat   4620
tgggatgata ttaaaaaaac aaatgaaagt ttttattttc ataaagaaat agggaaaaga   4680
atttatttta caggagatat gggacaatac catccggatg gaaatattga atttttagga   4740
agaaaagata gacaaattaa aattaatgga tacagaattg aactagaaga aattcaaaat   4800
aaattaaaat ctcatgtata tgtcaaagat tcgtttatta cagtaaatca gaataatatt   4860
tctgcaaaaa ttcttgcttt tattatatta cataataatt catcaatgat gtctcataca   4920
aatataaaaa aggaactgaa atcatttctt tataagaatt tatctgaata tatgattcca   4980
aatcattttc aatttcttaa aaaatttcca ttaagtaaaa atgggaaaat agatgaaaat   5040
aagttatata agatgcatga tattccaata ttaaatatac aaaaatctgc aaatacaaaa   5100
ttgcaaaaat ctttgaaaga aatttggaaa gatttattaa aaatcaaaaa agatatatat   5160
ataaatgata atttttttca attaggtgga tcttctcttt tagctgttcg catgacaaat   5220
ttgatatcaa aaaaattaaa tttaaatatt gatgtttctg ctgtttttaa atatcaaaca   5280
attgaaagtt tagaaaaatt tttacaaaaa gacaaaataa aaatagaaaa aaataatatt   5340
actaaacaag agcgtatcct atattatgaa tag                                5373
```

<210> SEQ ID NO 29
<211> LENGTH: 789
<212> TYPE: DNA

<213> ORGANISM: Ecteinascidia turbinata hologenome

<400> SEQUENCE: 29

```
ttaaaaaatt tgaatattaa ataattggct aaaattgtct gttgttgcat gacatatatc     60

tgaatatgat agatttttaa tttttgaaat acatttggca acataattaa cataactagg    120

tttattagat tttcctcgaa aaggatgagg tgttaaatac ggagagtctg tttcaattaa    180

aatacgattt aaaggaattt ttcgaacaag atcccttaaa tttgcagaat ttttaaacgt    240

caaaattcca gaaaaagaaa tatacaatcc catatctaaa ataattttag ccatttccca    300

tgattcagta aaacaatgaa caacacctaa attaacgtta tatttttcta agatcgatat    360

agtatcttgc gaagcagatc ttgtatgtat aattaaaggt gcatttaatt tcttagatgc    420

ttgaatatga ttaataaatc tttttttttg tacaagaata tgtttttcag atttagttcg    480

ataataatct aatccagatt ctccaacagc aataatttta gagtgtgcat taaaaatatt    540

tattaaatct aaagtagatg gttctttacc ttttatttcg ttgggatgtt ttccaattga    600

tgcataaata ttattaaact tttctgtaat tggtattatt gtttttaaat tttctatatt    660

taagcatata gaaagaagat atttgacatt tttatgatat gcttcatcaa taatatcagc    720

taaattcatt tttaattctt ttaaatttaa aatatctaaa tgacaatgtg aatctactaa    780

aattggcat                                                            789
```

<210> SEQ ID NO 30
<211> LENGTH: 915
<212> TYPE: DNA
<213> ORGANISM: Ecteinascidia turbinata hologenome

<400> SEQUENCE: 30

```
tcattcatta tataaatacc attcaataaa taatccttca agaaataatt ctgtattaaa     60

taaataatct atttttataa tttttttttct ttctactaaa taaaagtcaa taagataaaa    120

ccattgagat aaagattttt tttttgctaa tttccaaaaa atagaatttt tttttttttaa    180

aattaatata tatattaaat tataaactaa ttgtattaaa ctatttatta ttaatacaag    240

atcaatatct tgaagttttt ttgtttgaaa tattggtgtt tttttatcta aaaaattttg    300

aaaaacagaa tttatttttt ttaaatatcc ttttttttttc caaatttcta aataaatagg    360

accaaatcca gggatattaa aaatatttaa taaattttta gaattattaa tttcatattc    420

ccaaaaaaaa ttttttaaat tttgattttt ttcttctaaa aagaaattca tataccaaat    480

ttgacatcga ctgcgtattg taagtggtat agattctaaa taatctgcag tcaatattaa    540

tatagttttt tctctttttt cttctaaaat tttaagaaat gcattatacg caaataaatt    600

catattatga gatttatcta taataacaac acgatatcct cctatccaag atgtcctttg    660

aagaaaaaaa ataatatttc ttatttgatc tatttgaatt tgatttaatt ttccttgggg    720

ttttatatat aataaatcag gatgttcaga taattcactg ctattacatg aaagaatttt    780

ttgagcacac aattttacaa aatgtaattt tcctgttcct ggaaatcctg ttaataatag    840

cccataaggt attttattat tttgtaaatg ccaattaaat tttttccaaa gagttttttg    900

ccaaaaaaat atcat                                                     915
```

<210> SEQ ID NO 31
<211> LENGTH: 624
<212> TYPE: DNA
<213> ORGANISM: Ecteinascidia turbinata hologenome

<400> SEQUENCE: 31

```
atgagaaaat tatattattt ttttaaatct aaacatataa tatttgcatg tgatagcacc     60

caatattatt ggcgaagtaa atatttttct gaatataaaa aaaatagaaa aatgacaact    120

ttaagaaaaa atgtaagaaa ctcaataaaa ttttttaaag aaaaaaattt taaattatgt    180

attgaagttc ctggttgtga agcagatgat attatttatt gtttgataaa ttataaaatt    240

cataataata taattattgt tagttctgat agagatttta tacaattgca atctacaaga    300

gtacgattat ttaatccaca tacatataaa tttcgtaaaa ttcctgaaaa attagaatat    360

gaattattta taaaatgtat acgaggagat gtttctgata atatcccatc tgcttatccg    420

tatgtaagag aatctctaat aaaggaagca tattataatc catctaaatt ttttattttt    480

atgaaaaaaa aattatctga taatattgca gtatacaaaa aatatcaaag aaatcgatta    540

ttaatcgata tgaaattttt accaaaaaaa tatatatcat taattaaaat attgatagat    600

aaattatctt taatagaaga ttaa                                           624
```

<210> SEQ ID NO 32
<211> LENGTH: 1167
<212> TYPE: DNA
<213> ORGANISM: Ecteinascidia turbinata hologenome

<400> SEQUENCE: 32

```
agaaataatt tttccaatca tggaatcata atatggtgga atagtatatc cactgtaaat     60

atgcgaatca acacgtatgc ccggccctcc aggtggatga taaatgttta atgttcctgg    120

acttggaaga aatgtttttg gatcttctgc gttaattcta cattgaatag aatgtccttt    180

aatattaata tcattttgat gatatgttat agtttgattg gatgcaattt gtaattgttc    240

tttaactata tctatacctg taacaaattc tgtaactgga tgctctactt gaatacgagt    300

attcatttca ataaaaaaaa attctccttt ttcatataaa aattcaaaag ttccagctcc    360

tcgatacata attttttttac aaacttccac acatttttta gcaagatttt cgcaatcttt    420

tctatttaaa gttgaaggag cttcttctaa aactttttga ttacgacgtt gtatagaaca    480

atcacgttct cccaaatgaa ttgcattacc ttttccatct cctaaaactt ggatctcaat    540

atgtcttgga ttttctaaaa atttttccat atatatattt tcatcaccaa aactagcttt    600

tgcttcagtt ttagtcatat caatagaatt agaaagtttt tcagggtcat agactactct    660

aattccaaga ccaccaccac cttttgcagc ttttagaata atcggatatc caattttttt    720

agctaaaatt tgattttttt tagtatcagt atctaatttt cctaatgatc cttctataca    780

agatattccg tgttctttca taatgttaat tgcagaaatt ttatctccca tgtttttcat    840

atttttata gtaggaccta caaaaataaa accactattt tctactgcag atacaaaatc    900

agaactttct gataaaaatc catatccagg atgaatagaa tcgctatctg ttaattctgc    960

agcactaata atagcaggaa tatttaaata actttttaaa ctattagatg gacctataca   1020

aaccgattca tcggatagtt taacatgttt aagatttctg tcagtagttg aatgaacagc   1080

gacagttttt atttgtaatt ctctgcaagc tcgtaaaatt cttaatgcta tttcaccacg   1140

atttgcaata agtagttttt taatcat                                       1167
```

<210> SEQ ID NO 33
<211> LENGTH: 459
<212> TYPE: DNA
<213> ORGANISM: Ecteinascidia turbinata hologenome

<400> SEQUENCE: 33

```
ttattcaaga ataattaaag gctgatcaaa ttctacaggt gaagaatctt caataagtat     60

tgattttatt attccagatt tatcagattc aatatgattc attgttttca tagcttcaat    120

tataccaatt acctgtccaa ttttaataac agatcccact tcaataaaag gttttgcagt    180

aggtgaggga gatcgataaa aagtgcctac cataggtgat tttattatat ttattgaaga    240

ataaatatca gaaacttttt tttccttttt tagaaattct atagaattag atttttttaa    300

ttttttttt gtttctcttt cagaagataa aatattagat acatctgatt ttttagataa    360

ttgaatagat tcttctcctt gaactatttt catatcagat aaagaaaaat tatccattaa    420

ttcaagtaac ttttgtatgt ctttatgatt aattttcat                           459
```

<210> SEQ ID NO 34
<211> LENGTH: 2247
<212> TYPE: DNA
<213> ORGANISM: Ecteinascidia turbinata hologenome

<400> SEQUENCE: 34

```
ttataattta atatattttc ctaatttcca aaattttaac atattattat agtttttgga     60

aaaagggttt cctgattgtc ctaaaggaca tataaaacaa cttttatttt ttttatttaa    120

atcaattatt tgtctatata caggtccagc tttttgaata aaattttcat catatggaga    180

tgcattaata gtataggcat taccttctgt agatattttt ctattccata aatatttaat    240

tccccatatt ttaccaaaaa taggattaat aaattttgct tggtggattc tcccccattt    300

ccatttttct atattatttc ctaatatatt tttaatatta attattgctt ttttaaataa    360

aatatacaga acatcagtaa tattttttttt tttatttaaa caaataaatt ttccgttttt    420

ttttaattga tcaataataa aaagaggatt tggaaaattt tgataattta taggtaattt    480

aggttgtatt tttattattt cttgaaacca aaatgaaaat actgtagcag aaatactatt    540

acttgacata tttccattcc attttttaag gtatactaat atttttttttt caaatttgtt    600

ttgaggaatt atttttaata agaaatcttt taattcatac cataataagt tatttgtatt    660

tatttgaata tctttcatat tttttattgt cattttattc atattattaa tcatattttc    720

aatttttttca gcacggtatg gaggaccttt ccaaatataa gtgagattat aaggatattc    780

attcggaata attttgttat ttgcattaac aatatatcct ttagatggat taaatacatg    840

tggcaattta ttaaatggaa taaattcatt ccaagcattt tttgaattaa atggtataac    900

atattttaaa ttttcttttt ttcgaatagg tatccttcca ggaaggtaat atccaatatt    960

ccctaaaata tctgcatata aaaaattcat tggagctgct gtaaaatctt ttaaagcatt   1020

tttaaattct ttccaattag aggcgtaatt tatttctatt aaactttgaa tagttttatc   1080

gtcagaatct aatcctgtcc atcttatagc tattttttgg tttattattt ttttatttat   1140

ttggttattt tcttgaatta aattattaat aataggacca atatcagata attcaatttc   1200

gtgttgtata gttttttttt ttcttacttt gattttctca aaaatttttt ttgtaggtct   1260

tgtcttatca attaaaaata aatcagaaca atctagtcct gcatcagtta ttccccaagc   1320

aatattttta ttttctcctg aaataatgca aggtatacct ggaattgaag aacctctaat   1380

gtttaaagat ggaccttgta tgttagctaa ataacaaata ttaggggaag ataattctaa   1440

atgaatatca tttgctaata ttggtttgcc tgattttgtt aattttcctg aaacaaccca   1500

tccgtttgat cctttgcctg gtaaattttg aatattaaga ttattttgta tctcttgaga   1560

gatattaata aaagattgca tattattatt atataatact tgattttttt tatttgtatt   1620

taaattatct gaagattttt gtgtataatc taataaattg ctgttgttta attcttctat   1680
```

```
gtttaatgtt gttggtgcgt tttctggata ttgaattcta atatcttcaa tatttatatc   1740

agaggatttt tccataataa gggaattatt taatttatct tgccaagtat gatattgtaa   1800

ttgccaagca attatttttg accaaataaa tgaatctata tttttccaat attttggttt   1860

atagaataat attcttaatt ctataggtct tttcccagat ttaatatatg catttactcc   1920

tgctgtatat ccattaataa tttttttttgt tttaatatta aaatgtttcc agttctcttt   1980

tgcacatcga taaaatcccc atgtttttaa atatttgtct tcctttatag ttcttttccc   2040

aaaaatttca cttaatgttc ctgaagcaat atgacgctgt aattccattt gccaaaatct   2100

atcttttgca tgcatatatc ctaatccgta aaaagcatca atgtcatttt tagaagcaaa   2160

aatatgagga attccataac tatctaaatt aatttgtatt tttccataca gaccttgaat   2220

taataaactt ttttttgaat ttagcat                                        2247
```

<210> SEQ ID NO 35
<211> LENGTH: 480
<212> TYPE: DNA
<213> ORGANISM: Ecteinascidia turbinata hologenome

<400> SEQUENCE: 35

```
ttatccttta agaattttta atcttaattt tttaaatttt tctatttctt gaacagccga     60

atattcatta gatcgtaaac ttcctgatgc aggacctaca aattttccgc atacatattt    120

atgtgcatga tatgcttttt ttaaagaaat tataaaaatg ttatattttt tttgaattat    180

aggataggaa gtgaaattta attttcctat agatctcata caatttttta ccataaattg    240

atgatctctc caatttaatc cactcatttc tggttgtgaa attggaggca taagagtagg    300

tcttacattt tcattatatg atttagaaga aaattctcct gtatagtata aagcaacttc    360

tgttgctttc ataagtttta tagcattatt taaatataat aaagattgta aaaacttttt    420

tttagaatat tcaaaaataa aacattgtaa agatataata agaccttgta ttattatcat    480
```

<210> SEQ ID NO 36
<211> LENGTH: 1086
<212> TYPE: DNA
<213> ORGANISM: Ecteinascidia turbinata hologenome

<400> SEQUENCE: 36

```
atggataaaa aaatattaaa accttgttat agaagtgatt ctatattaga tcataaccaa     60

ttgaataaat tgcatgaatt aactccaatt atttttggag caagtgcttt tcaatactta    120

aatgctggat ctgaaatagg actttttgaa ttattatatt attctggtcc aaaaaaaaaa    180

tctgaattaa tgatagaact cagtttaaaa gaaagagcta tagatatttt attattagga    240

aatacatctc taaatttaat taataaagaa aaatcttttt ataaaaattc tctaataata    300

caaacaattt ttgaaaataa tatttgggat attttcaaag atttgattgc ttttgagcaa    360

tatattgttt atctggggca atttgatttt acagattctt taagaaaaaa tactaatatt    420

ggattgcaaa gaatttctaa tacatcaaac agtctttata aaagctttaa taaaaataaa    480

aaattagaaa aaatattcta taattatatg aattcatgga cccgtctttc taattattat    540

ttaattaaat atattaactt taataatgtt catcgtttac ttgatgttgg aggaggaaca    600

gcaattaatg ctattgcttt agcaaaaaaa tatcctaaat taaaaattac tgtttttgaa    660

atcgatgcat ctgcaaaaat agctcaaaaa aatattcaat cttctggatt atcaaatcaa    720

ataaatgtca ttcatggtga tatatttaaa gatcaatttc ctactggata tgattgtgta    780
```

```
cttttttcac atcaattagt tatatggact cccgaagaaa atatagaatt attacataaa    840

gcatataaaa ttttatcttc ccatggatta gtaattattt ttaattctat atctaatgat    900

gatggaaaag gtccattatt agcagcacta gatagtgtat attttgctag tattccttcg    960

gaaggaggca tgatttattc ttggaatcaa tatgaagaat ggttgaaaaa atcaaaattt   1020

caaaaaattt ctcgaattaa ttgccatcat tggacaccac atggaattat aaaagcatat   1080

aaataa                                                              1086
```

<210> SEQ ID NO 37
<211> LENGTH: 663
<212> TYPE: DNA
<213> ORGANISM: Ecteinascidia turbinata hologenome

<400> SEQUENCE: 37

```
ttattttttt aaagcaagag tgattccatc agcaaatgga agcaaactga tttctactct     60

attatcagat aatagaaaat tattaagatc attaattatt ttagtatcag cattatattt    120

aatgttttga gatacagtaa cttttcctga ccataatgta ttatcaaata atattaatcc    180

accagctttt aataatttta aagaatattc ataataatta atatagtttt ctttatctgc    240

atctataaat ataaaatcaa aatactcttt tttatgcaat aataattttt ttaatgttag    300

taatgcatca ttaatatgta gagaaatttt atgattaatt ttttctattt tccaaaattt    360

tttagcaata tcagtccatt ttatattatt atcacatgct attaatttc catttttcagg    420

aagagattta gcaatacata tagaactata tcctgtaaaa actcctattt ctaatgccat    480

ttttgctttc attaatttta ttaaaagaga tataaactgt gcttgttccg gaaaaatttg    540

catatttctt tctggcaatt tatttgttat atatctcaat tttttaagag tatgactttc    600

tcttaaagaa gtatttctaa tatattgaag aatattttca tttatctgaa tgtgatttat    660

cat                                                                  663
```

<210> SEQ ID NO 38
<211> LENGTH: 1461
<212> TYPE: DNA
<213> ORGANISM: Ecteinascidia turbinata hologenome

<400> SEQUENCE: 38

```
ttaattagca ttttttttta aaaataattt ctgtattaaa atttctttaa tttttttggg     60

attagctttt ttattttttt gtattatttt accaaataaa aaatctaaaa tttttgtttt    120

cccattatga tatttaataa tctcttttgg aaaactatca attacttcat taacagtttt    180

ttctattata tttatatcat taatttgcaa taattttttt ttatggataa tatcatcaat    240

atgagatttt ccatttgtaa tccataaatt atcaaaaact atttttgctg ttttattaga    300

taataatttt tttttaattt taaaaataat atttgataaa tgatgtattt ttataggaga    360

atctataata gatagtttat atttttttag tttagataat aacattgatg taatccaatt    420

agatgctaat tgagagtttt ctaaacctac agaaaaaact aatttttcat aaaaatttaa    480

taattgagga ttttcaagaa acatttcgat ttctttctta tcaagataat gttctaattt    540

taaacgattt cgtattgaat tgggcaattc aggtaataat aaatgaattt tctttatata    600

agaatatgtt attttaacag gtaataaatc aggttcaggg aaatatctat aatcatgttc    660

atgttccttt atacgcattt ttttagtaat attttttttt gaatcaaaaa gacgagtttc    720

ttgaattata aattttccag attctaataa tgcgatttgt ctttttgatt caaaaataat    780

agatttttca ataaatttaa aactatttaa gtttttacac tcagtttttg tacctaatat    840
```

```
tgaagatcct aaaggactaa cagatatatt tacatcacat cgaaattcac ccttttccat    900

atttgcatgt gatattttta aatatcgtac taataaatgc aattctttta aaaaagaaat    960

tgcttctttt gcagatgtaa tatttggttt tgttacaact tctaacaaag gatttccaga   1020

tcgattaaaa tcaatttgtg catttttttt tgtatgtact aattttcctg catcttcttc   1080

taaatgagca tgatgaataa atattttttt tatatatttt ttagaatcat taatagcaat   1140

aggaatatat cctcccatca aaataggtat tttgttttga ctaatttgat atcctttaga   1200

caaatctgga taaaaatagt tttttcgaac aaataaaaaa tatgtaggta tttttgcatt   1260

aattgctaaa cctaatctta tagcaaattc tatagcacgt ttatttaata tcggcagggt   1320

tcctggtaat cctaaatcaa tacccgatac ttgagtattt ggagcgtttc catattgatt   1380

tttcgcctta gagaatatct tgctttcagt tgataattgg atatgaactt caagaccaat   1440

tgcaatattc cattttatca t                                             1461
```

<210> SEQ ID NO 39
<211> LENGTH: 1182
<212> TYPE: DNA
<213> ORGANISM: Ecteinascidia turbinata hologenome

<400> SEQUENCE: 39

```
ctataaaata ttttgaggtt tttgcatatg ccaatcagta tttaattgaa attgatgcgc     60

tatatttaat aatttttctt cagtgaatgc aggacttata atttgtaatc caattggtaa    120

tttttttaca aatcctgctg gtatagtaat tccaggaagc cctgccatat ttaaagccaa    180

agtatacata tccgaaagat ataataatga aagatcgttt ttattttttc caattttgta    240

tggtaaaatt gggctagtag gacccataat tacatctacc ttttcaaaag ctttttgaaa    300

atcttgaaaa attaatcttc gaatttttttg tgccttaata taatatgaat tataaaattc    360

agaagaaagc ataaatgttc cagctaaaat tcgttgtttt acaatttctc caaatccttc    420

tcctctcgat ctttcataaa gatcccatag attttttgga ttttgacatc gatatccaaa    480

acggattcca tcatatttag caagattaga tgaagcttct gcttgtgcta taatataata    540

tgcagaaata catatatcat tatgtttcat tcgaatcgat tttaattttg ctcccataga    600

ttcgtatttt tttaaagcat gttgaatagt tagttcaatt ttaggatcca atccttttga    660

aaaataatct tctggaattc ctatttttat tccttttata gaattattaa gtattttagt    720

aaaatctttt ttatgtgcaa aagaagatgt agaatctttt ttatcgtatc cagaaataat    780

attaagtaat aatgcacaat cttctgctga atttcccata ggacctgctt gatcaagact    840

ggaagcataa gcaattattc cgtatcttga tactaaaccg tatgttggtt ttaaacctgt    900

aatgttacac atagaagcag gttggcgaat agatcctcct gtatctgttc cagttgctat    960

gggagttaaa ttagcagata tagccgcagc agaaccacct gaagatcctc caggtattct   1020

agataaatcc caaggattct tacaaggtcc aaaataacta gattcattag aagaacccat   1080

agcaaattca tcgagatttg tttttcctaa taatactaaa ccagactttt tacaaagttt   1140

tactatgtgt gcatcataag gagaaataaa attttttaac at                      1182
```

<210> SEQ ID NO 40
<211> LENGTH: 310
<212> TYPE: DNA
<213> ORGANISM: Ecteinascidia turbinata hologenome

<400> SEQUENCE: 40

-continued

```
cttattttga taaaaatgta ggaaccaaaa ataatttatt ttcatgatct atagaaggag      60

catttttaa tatatattta ttatcaaaat cttttttaat aggactgtct tcttgtaaaa    120

tttgagtttt atttgaaata ttatacaatg gtttaatatt attagtatta attaatgaaa    180

ttttattcat tacattaaga caaatatcta attgtttttt tgtttgcaaa atttctttat    240

tatctatttt tagacaagat tttttggata attttttaat ttcttctgta gttaaataca    300

ttttatacat                                                          310
```

<210> SEQ ID NO 41
<211> LENGTH: 1493
<212> TYPE: DNA
<213> ORGANISM: Ecteinascidia turbinata hologenome

<400> SEQUENCE: 41

```
tgtataataa atttgaagta attattatag gagccggtcc atcaggtttg atgttatcaa      60

tagaactagc tttaagaaat atttcatgtg ctataattga aaaaagaaaa tctagattaa    120

ttgaaacacg tgcatttgga ttaatgccat taactttaaa tttattagat atgcgtggat    180

tagctaattc tatgatatca gaaggtataa tatgtaacta tgctcccctta ggagatggaa    240

aaggaaaatt atattttcat tcattaaaaa caaaatttcc ttttttatta agcattccac    300

aagagaaaac agaagaaatt cttgaaaaaa gaacaattca attaggtgta aaaatttttta    360

ataatcacga attattaaga tttgaagaaa aaaatggaga ttttttatta ttttgtaaaa    420

ataaaaaaga agaaaatatt tttatatctc gttatttaat agggtgtgat ggatcttata    480

gcagcgtaag aaatttagca aaaataccat ttactttttt aaaacaaaat aaaacactta    540

tgcatggtga tgtttattta aaatatcctc caaaagataa aatatttgct aaaacttcta    600

aaagaggaat gattgccatt tttcctcata aaaatggatc ttatagagct attgcactgg    660

atcaaaaaaa aatgctaata ccagtaaata caaaattaac attagaagat tttacagaaa    720

gtttaacatc cttatcagga ggttgtaact ttggtataaa taattttata tggcttaaaa    780

ggtttagagt tcaacaaaag caatctcaaa gttatcaaaa aggaaaaatt tttcttcttg    840

gagatgctgc tcatactcat atgccagcag gagggcaagg attacaagtt gctatacatg    900

atgcgtttaa tctaggttgg aaacttgcat tttatatcaa aaaaaaatct tcatataatt    960

tattatcttc atatacagaa gaaagaagaa aaattaatga aattgctatg aaaagaagtt   1020

ctatgttatt taaatatgaa atagctaatg atatatttag catgagttta aagtggacta   1080

ttaataaatt attttctttt aaatttatgc aaaaatattt tgcaaaagac atgagtggat   1140

tgtctactaa ttatcataaa attttttcta aaaaaaaaaa ttataaaaaa tttaaatgtt   1200

tgggatattt tattagagat ataaaaaattt atacacatga taatacacta cgttttttat   1260

attcttttct aaaacaagga aaatttgtat ttattagtat aatgcatcaa atttctttta   1320

tttcatggaa gaatacggat attattttcc ttgcttctga tgatataaaa aaaatatatg   1380

gaattaattg ttgtctagta aggccagatg gtataatttg ttgggctgga ttagatacga   1440

aaaagtttac caaaaatatt ttttatgaaa ttattttttt aaagcaagag tga          1493
```

<210> SEQ ID NO 42
<211> LENGTH: 2007
<212> TYPE: DNA
<213> ORGANISM: Ecteinascidia turbinata hologenome

<400> SEQUENCE: 42

```
atgaatagta ttagttctat atatttaaaa aataataaaa ttcttacaga aaaaaataata      60
```

```
aaaaaatgta tgttaattag attagttgaa gaacgattat tgcaagcttt ttcagaagga    120

gaactttatg gaacaataca tacttgcata ggacaagaat taataggtgt tatggcttgt    180

caatttataa atcaaactga tacaattttt tctaatcatc gatgccatgg acattttttta   240

tcatttacta atgatgtaga aggattaatt tctgaaatat atggtaaaaa aacaggagtt    300

tgttctggaa taggtggaag ccaacattta tataaaaata atttttattc aaatggcatt    360

caaggaggtt ttatgcctgt tgcagcaggc ttggcatatt cttttaaaga aaataataaa    420

attgcaatta tttttattgg agacggaact ttaggagaag gaattcttta cgaaacatat    480

aatattattg ctttattaaa gttgccatta cttattattt tagaaaataa tttatatgct    540

caatctaccc atcaaaaaga aacattatca ggagatatat taaaaagagc tcaagctttt    600

aatatttatg cagataaatc tgatatttgg aattggaatt cattatataa aaaaatggaa    660

ttcatgatta attatgtaag gcattataga tctccagcat ttttagaagt ttcttgttat    720

agattaaaag cccactctaa aggagatgat gacagagatg aaaacgaaat aaatttttat    780

aaaaaaaaag atcctgtaaa gattataatg gatcaaattt ttcataaatt gcaaaaaaaa    840

tctattattt ctttaataaa agaacgtata gaaaatgcta tttataaagc aaaaaaagat    900

gtatatgcta attataaaat ctatcaatat aagaattata atatctttaa taactatcaa    960

aatttatatg ttcattgtaa aaaaaataaa cgtatttcta cattattaaa taatacatta   1020

cataatctaa tgaaagaaaa tagtaatatt atcttattag gagaagatat caaagatcca   1080

tatggaggtg cctttaaaat aactaaaggt ttatcttcta aatttcctga tagagttatt   1140

aatactccta tttcagaagc tgctattgtt ggattttctt gtggcatgtc tttatcaggt   1200

ttgttgccta ttgttgaaat tatgtttgga gattttatta cattagcttt tgatcaaatt   1260

ttaaatcatg caagtaaatt aaaatatatg tataattata atgtttcaac tccgataatt   1320

atcagaaccc ctatgggtgg tggtagagga tatggaccaa cacatagtca aactttagaa   1380

aagcattttt taggaattcc aggcattcga atttttgcaa taaataattt atttaatcca   1440

gaaatattat ataaatctat attaaagaat aatcaagaat tatcaattat aattgaaaat   1500

aaaattttat atacaaaaaa tcttttatcc tttcctttaa aaggatattt ctataaattc   1560

aaagattatc cacaacctac tataatgatg ttgcctaaat ccaatttaat tgatattact   1620

cttattacat atggaggatt agtagatatt atagttgaaa taatagaaga attatttgaa   1680

gaacatgatt taattgctca gcttatatgt cctatacaaa tttatccatg tcaattatct   1740

gaattttcta atttaataaa aaaatcgtct ttgatagtct taatagaaga aggacagggc   1800

tttgcaaatt tcagcagtga gatgctttct cagcttattg aaaatgataa atttaaaaat   1860

tgtaatttct taagatgttc ttcagaacca tctccaatac cagcatcaat atatttggaa   1920

gataagatgc ttccaaataa aacaaatata cttcgtaata ttttagagat ttataatgaa   1980

aaaaaaaatg ttaattccaa gatttga                                       2007
```

<210> SEQ ID NO 43
<211> LENGTH: 1098
<212> TYPE: DNA
<213> ORGANISM: Ecteinascidia turbinata hologenome

<400> SEQUENCE: 43

```
atgaaaaaaa aaatgttaat tccaagattt gaggcaaatg ataattccgt aaaaaattatt    60

gaatggttag ttaacgatcg tgtttttatt aaaaaaaata ctcctttatt aaatattgaa    120
```

acatcaaaaa cttttcaaga aattaaaagt aaatatgatg gttttataaa aaagatgtgt 180
caagaaggtg acacacttca tactggagat atatttatag aattttatac aaaattagaa 240
gatcttttaa aaaaaaatac ttattttaaa aaaaaaaaag atactgtttt aagctgtaaa 300
tctacatacc aaaggttttc taaaaaagca aaaaaaattt tattagaaaa aaatattgat 360
atatcttctt gcacagaaga attaataact acaaaagtat taaataatat tacaaatgaa 420
atacgaaaag ataaaaaaaa taaagattta ataaaatatt ttccaaattt agaagttaaa 480
aaaaattcag atattaaaaa tcgagaaatt tctgttttag aaaaatcaga tggaaatatt 540
ttttcaagct ctattatgat tcaattatct tctgaaaaaa ttagagaaaa tataaaaaaa 600
atacctaaat taaatggaca gattttccct tatcttatgt atttttatat acaagaatta 660
tctatttcac caaaatttac cgcattttat agagaaaaaa atattattta ttataataga 720
attaatttag gaattttaat agataataat aatatattgc aaattattgt tttaaaagat 780
gcaaataaat tttcactatt agaattgcaa aacgaattaa ttgataaaat atgtagatgt 840
tatgaaaata atttagaaat tgatgatgtt gtacattcta caacaagtgt gtcggattta 900
tctggaaata atattatatc ttttcagcct ataattaatc aaaaacaatc tgttatcctt 960
ggcataggag gagatactaa tcttttagga aaacctataa cttttaatat agtatttgat 1020
catagaattt taaatggaaa ggaagttgca atatttttag aaaattttaa gagaaaaata 1080
ctacaaggaa tatactga 1098

<210> SEQ ID NO 44
<211> LENGTH: 807
<212> TYPE: DNA
<213> ORGANISM: Ecteinascidia turbinata hologenome

<400> SEQUENCE: 44
atgcaaagat atagatttta tagagaacat aaatttataa ttccattgat taatgatata 60
actagaaaaa ttgcttctac taatttccaa aacaataaag aaatctcttt acttataaaa 120
aaactctcta atttgcaatt agttttaaca aaatattcag aacatgaaga taaagcatat 180
cattcgttat tagtaaataa aggatctaat atacattatg atctagaaaa tgatcataat 240
gattatgaaa aaaaattttg tgatttaaaa aatttattaa aaataataaa agatttaaaa 300
aataaaaaag aaaaaattgc atatggttat aaattttatt taaattttag agaatttgaa 360
gttaaaaatg ctattcatat gaataatgaa gaactttata ttatgccaaa attacaacaa 420
ttatattctg ataatgaatt acaagctatt gaactaaaaa catataaact tatgaaagtt 480
agtgaaatca ttcatatgat gaaaactatt tttatatata tggatgcaaa tgatagattg 540
cattatttta atgatattaa taaatcttct ccagaaaaaa caaaacctat tttatgtagt 600
attttaaaaa taaaaaaaaa taactcttat cttatttcta aaaaagaaaa agatttttta 660
ttaaattatt tttctatttc aaaagaagaa tataaaaata ttaatgtaga agataaaaat 720
aaatatttat gggaattatc agaaggggaa tttatagaag aaaatatgag tatgaaatca 780
caacatgatc ctaccagaaa atattaa 807

<210> SEQ ID NO 45
<211> LENGTH: 342
<212> TYPE: DNA
<213> ORGANISM: Ecteinascidia turbinata hologenome

<400> SEQUENCE: 45
ctaaaaaagt aaatgatatg ttttgataac tgagtaattt aatacttcta atattggccc 60

```
atctactcga attatacgaa aagcaagatc attatcatga tttttttttg attcataaca    120

atcattagaa ataatagaaa aatttttat ttttttttca tatgatttta atattttctg    180

tattattata aataaatcat ttttatgtat aatttcagaa aaactatttt ttaataaaat    240

agtattttta gaattttgta aaataattaa ttctttttga gaatgcggca acttttctgg    300

gggtaaaagt aaaaaattat ttttcaacat aaatatattc ac                        342


<210> SEQ ID NO 46
<211> LENGTH: 405
<212> TYPE: DNA
<213> ORGANISM: Ecteinascidia turbinata hologenome

<400> SEQUENCE: 46

tcaatttcct ttagtacgtt catgacgttc ttttgcttct ttagcttgaa ttgataaagt     60

agcagttggc cttgctaata atcttttaat accaattggt tctccagtct cttgacaata    120

tccgtatgta ccatttttaa tattttctat ggatttttgc actttttgta ataatttaga    180

ttgtctttcc acagtcttta aaaaaatctg ttgcatttct tgttttgttg caagatcaga    240

aatatccgag ctattttcat tttcagaaag tctttttctt gtttcagaaa tggataaaat    300

aagatctttt ttttgttggc ataaaatttt ttcaaaaaat tcatattgtt tttgattcat    360

atatgaatct ttagacatat ttaacagttc agtttttgtc agcat                     405


<210> SEQ ID NO 47
<211> LENGTH: 918
<212> TYPE: DNA
<213> ORGANISM: Ecteinascidia turbinata hologenome

<400> SEQUENCE: 47

ttatttattt ttatttttat aaaaaataac tataacacca aataaaataa ttatccctcc     60

taataaattt ttccatgatg gtattttttt taaaaaaatc cattcaaaaa ttatagataa    120

aaaaggcaca aaatacaaag aatttgctac tactcttctt tgaagatgat ttaaacaaaa    180

actccataaa gtgtaagcta atgcaccagg accaattcca agtaaaatga tagatattag    240

ttctgttttg ggagcatagt atatctcttt tattgcaata ggagcagaaa aagacatcgc    300

aatagttgca aaccaaatac accatgaagt tatctctaaa ggagataatt tttttaaaag    360

tggtttttgc attatagtat aaaaagcacc acacaatgca gaaaaacata agtatattac    420

gccataatta atagatttag attgaataaa gatcatagta attcctacca aagaaataaa    480

tatacctatc caccccatag tattaatttt ttcatttaaa aagaaaaagg ttattataga    540

aacaaatatc ggtataagac taataataaa actagttatg gttggatcta ctgttttttc    600

tcctaaatta attaatatag tatacattcc aataccaata cttccggtta ttaatagcaa    660

aaatatatcg tattgttgaa gaacatattt tttaggaatt aagaaaaaat accatgggaa    720

aataaataaa gatgcaaaaa agaatcgaag aaatcctata gattctggat gaaaatagtt    780

taatgtgtct ttaattccta cataagagag agaccacatt attataacgc aaactaaagc    840

aatataagct attatatttt taaaaaaaag gaatatcatt ttatgaatta tattaaaaat    900

attttttaaa tcatgcat                                                   918


<210> SEQ ID NO 48
<211> LENGTH: 1446
<212> TYPE: DNA
<213> ORGANISM: Ecteinascidia turbinata hologenome
```

<400> SEQUENCE: 48

```
atggatattt tacaaaatgc taaagaagtt ttattgtttt ccaacaattt aacggaaaat     60

gatattcaaa aagaaattaa tattgctatg tcatacaata tagattttat agatttatat    120

ttagaaaaat ctgaaacaga aaattggatt ttagatgata ggattattaa aacaggatat    180

tataatattt cacaaggttt aggagttaga acttttttag gtgaaacaag aggatattct    240

tatgcagata taataaatat taattcttta aaagaaagta taaaaaaagc aaaaaatata    300

tcttcatttc gaaaaaatat taaattaaat tattttaata atattaaaaa aaatcattgt    360

gtatatattt ctaaaaatcc tattgaagaa tataaacaat ttcaaaaaat ttcttttttta   420

aaagaaatag ataaatatat tcgcgaaaaa aatgcaaaca ttattcaagt tatagttcaa    480

ttatatagtt ctttaaaaac aattttagtt gctgcttctg acggtacttt tgcagcagat    540

atgcgtccta tggttcaatt gagaatttct gttattttac agataaataa taaaatagaa    600

caaggaaatg caggaatagg aggaagatat tcttatagag ttttatttaa tcctaaaaat    660

tggaaaaaaa ttgcagatga agcaattcga atagcattaa taaatttaaa atctatacct    720

ttatcagctg gattgatgcc agtagtatta ggatctggtt ggccaggtgt tttgttacac    780

gaagctgttg gacatggttt agaaggtgat tttaatagaa aaggtgtgtc aaattttagt    840

caaaaaatgg gaaaattaat tgcatctcca ttatgtactg ttatagataa tggaactatc    900

aaagataaaa gagggtcttt aaatattgat gatgaaggta cggaaacaaa gaaaaatatt    960

ttaattgaaa atggaaaatt agttggatac atgttggata aacataatgc attcttaatg   1020

aaaaaaaaat caacaggaaa tggaagaagg gaatcttatg cacatattcc tatgcctcgt   1080

atgacgaaca cttatatgtt acctggcaat tatgaattac aagaaatgat ttcttctatt   1140

caaaagggaa tttttgctgt aaattttaat ggtggggaag ttgatattac atctggaaaa   1200

tttgtatttg ttatgtctga agcttatctt attgaaaaag gcaaagtaac aaaaccatta   1260

aaaggagcta ctttaattgg agatggtcct tctataatga aaaaaatatc tatggtaggc   1320

aatgatttat cttttgattt aggaataggt atttgtggaa aaaatggaca aaatatacca   1380

gtaggagtag gacaaccaag tttaaaaata gatgaaatta atataggagg aacaaaaata   1440

aaataa                                                              1446
```

<210> SEQ ID NO 49
<211> LENGTH: 531
<212> TYPE: DNA
<213> ORGANISM: Ecteinascidia turbinata hologenome

<400> SEQUENCE: 49

```
atggtgaaaa ttatgataag atcaaggaat atctttttaa tcggtatgtc aggtgtaggg     60

aagagtacaa ttggcaaaca acttgctaat gaactaaaaa tggtatttta tgactcagat    120

gaaattattg aaaaacgatg tggtgcggaa attagttgga ttcttgatat agaaggtgaa    180

gaaggattta gaaaacgtga aagcgatatt atttatgagt ttactgaaaa aaagggcatt    240

gtgttagcaa caggtagtgg agtagttttg aaaaaatcta attgtaatcg actttctgct    300

cgtggaacag tgatatattt aagagcgtca ttaaaattgc atgttgaaag atcattgcgt    360

gataaaaaaa aatatctaat acaaaaacaa aatcaagaaa tagaattgag aaaaattcaa    420

gaaaaaaggg atcccctata taatagaata tctgacataa ttattgatgc taattctagc    480

agtattcgtt ctattgttaa taacatttta gataaattaa atgaaaaata a             531
```

<210> SEQ ID NO 50
<211> LENGTH: 351
<212> TYPE: DNA
<213> ORGANISM: Ecteinascidia turbinata hologenome

<400> SEQUENCE: 50
atgttcatta caggaaaaat atctaaaata gaaaataaaa ttgatgaatt tggtaaaata 60
gattactttc tttttttgga tgaaaaaaaa atttttctta acaattttct cggaaaatat 120
atttcattag aacacataaa aaatttaatt ttttgtatag gatgtcaaaa aaaaatgaaa 180
gcatggtata gaaataatta ttgtttttta tgcaataaaa aactagctat atgtgatatt 240
tgtataataa aaccagaaaa atgccatttt catttaaata cctgtcgtga accagaatgg 300
ggatggaaat attgtatgaa tatacattat gtttatcttt ctataacttc a 351

<210> SEQ ID NO 51
<211> LENGTH: 19
<212> TYPE: DNA
<213> ORGANISM: Artificial Sequence
<220> FEATURE:
<223> OTHER INFORMATION: Synthetic primer

<400> SEQUENCE: 51
tgctgcctcc cgtaggagt 19

<210> SEQ ID NO 52
<211> LENGTH: 20
<212> TYPE: DNA
<213> ORGANISM: Artificial Sequence
<220> FEATURE:
<223> OTHER INFORMATION: Synthetic primer

<400> SEQUENCE: 52
agagtttgat cctggctcag 20

<210> SEQ ID NO 53
<211> LENGTH: 32
<212> TYPE: DNA
<213> ORGANISM: Artificial Sequence
<220> FEATURE:
<223> OTHER INFORMATION: Synthetic primer

<400> SEQUENCE: 53
gcagaattcc atatggtgac ccggcacgag cc 32

<210> SEQ ID NO 54
<211> LENGTH: 38
<212> TYPE: DNA
<213> ORGANISM: Artificial Sequence
<220> FEATURE:
<223> OTHER INFORMATION: Synthetic primer

<400> SEQUENCE: 54
tttggatcca agctttcatc gctcctcctc cagcgtgc 38

<210> SEQ ID NO 55
<211> LENGTH: 37
<212> TYPE: DNA
<213> ORGANISM: Artificial Sequence
<220> FEATURE:
<223> OTHER INFORMATION: Synthetic primer

<400> SEQUENCE: 55
gcagaattcc atatgacctt gcaaaaagaa ggaattg 37

<210> SEQ ID NO 56
<211> LENGTH: 39
<212> TYPE: DNA
<213> ORGANISM: Artificial Sequence
<220> FEATURE:
<223> OTHER INFORMATION: Synthetic primer

<400> SEQUENCE: 56
cgcggatcct cgagttatat ttttttcgga tgaggaaag 39

<210> SEQ ID NO 57
<211> LENGTH: 35392
<212> TYPE: DNA
<213> ORGANISM: Unknown
<220> FEATURE:
<223> OTHER INFORMATION: EtuA-J

<400> SEQUENCE: 57
agaaataatt tttccaatca tggaatcata atatggtgga atagtatatc cactgtaaat 60
atgcgaatca acacgtatgc ccggccctcc aggtggatga taaatgttta atgttcctgg 120
acttggaaga aatgtttttg gatcttctgc gttaattcta cattgaatag aatgtccttt 180
aatattaata tcattttgat gatatgttat agtttgattg gatgcaattt gtaattgttc 240
tttaactata tctatacctg taacaaattc tgtaactgga tgctctactt gaatacgagt 300
attcatttca ataaaaaaaa attctccttt ttcatataaa aattcaaaag ttccagctcc 360
tcgatacata attttttttac aaacttccac acatttttta gcaagatttt cgcaatcttt 420
tctatttaaa gttgaaggag cttcttctaa aactttttga ttacgacgtt gtatagaaca 480
atcacgttct cccaaatgaa ttgcattacc ttttccatct cctaaaactt ggatctcaat 540
atgtcttgga ttttctaaaa atttttccat atatatattt tcatcaccaa aactagcttt 600
tgcttcagtt ttagtcatat caatagaatt agaaagtttt tcagggtcat agactactct 660
aattccaaga ccaccaccac cttttgcagc ttttagaata atcggatatc caattttttt 720
agctaaaatt tgattttttt tagtatcagt atctaatttt cctaatgatc cttctataca 780
agatattccg tgttctttca taatgttaat tgcagaaatt ttatctccca tgtttttcat 840 atttttttata gtaggaccta caaaaataaa accactattt tctactgcag atacaaaatc 900
agaactttct gataaaaatc catatccagg atgaatagaa tcgctatctg ttaattctgc 960
agcactaata atagcaggaa tatttaaata actttttaaa ctattagatg gacctataca 1020
aaccgattca tcggatagtt taacatgttt aagatttctg tcagtagttg aatgaacagc 1080
gacagttttt atttgtaatt ctctgcaagc tcgtaaaatt cttaatgcta tttcaccacg 1140
atttgcaata agtagttttt taatcatatt ttttctctat attataatct attttaaaca 1200
cgctattttt tattttattc aagaataatt aaaggctgat caaattctac aggtgaagaa 1260
tcttcaataa gtattgattt tattattcca gatttatcag attcaatatg attcattgtt 1320
ttcatagctt caattatacc aattacctgt ccaattttaa taacagatcc cacttcaata 1380
aaaggttttg cagtaggtga gggagatcga taaaaagtgc ctaccatagg tgattttatt 1440
atatttattg aagaataaat atcagaaact ttttttttcct tttttagaaa ttctatagaa 1500
ttagattttt ttaatttttt ttttgtttct ctttcagaag ataaaatatt agatacatct 1560
gattttttag ataattgaat agattcttct ccttgaacta ttttcatatc agataaagaa 1620
aaattatcca ttaattcaag taacttttgt atgtctttat gattaatttt cattattttc 1680
cttttatatt aaaatttaaa atcataagat ataaatatca aaaaaaatat ttaaacattt 1740

-continued

```
tttaacttta ataatatatt aagaccttgc tctcatatat ttttaaatat tttcattaat   1800

ttttaataaa aatataattt ttttaacata atttaaaata ttttttttata aaatgatgtt   1860

aaaaataaaa aatatagtta aatcattaaa tgattgccac aaaattatag aatctaatta   1920

acaaaatact ataaaaatgg tgggtactga gggattcgaa cccccggccc tcgccttgta   1980

aggacgatgc tctaccactg agctaagcac cctaacttta ttttattaat tttaatagga   2040

gcaaaaatga tgtcaataat tatatattaa gaattaaaaa atttgaatat taaataattg   2100

gctaaaattg tctgttgttg catgacatat atctgaatat gatagatttt taatttttga   2160

aatacatttg gcaacataat taacataact aggtttatta gattttcctc gaaaaggatg   2220

aggtgttaaa tacggagagt ctgtttcaat taaaatacga tttaaaggaa tttttcgaac   2280

aagatccctt aaatttgcag aatttttaaa cgtcaaaatt ccagaaaaag aaatatacaa   2340

tcccatatct aaaataattt tagccatttc ccatgattca gtaaaacaat gaacaacacc   2400

taaattaacg ttatattttt ctaagatcga tatagtatct tgcgaagcag atcttgtatg   2460

tataattaaa ggtgcattta atttcttaga tgcttgaata tgattaataa atcttttttt   2520

ttgtacaaga atatgttttt cagatttagt tcgataataa tctaatccag attctccaac   2580

agcaataatt ttagagtgtg cattaaaaat atttattaaa tctaaagtag atggttcttt   2640

accttttatt tcgttgggat gttttccaat tgatgcataa atattattaa acttttctgt   2700

aattggtatt attgttttta aattttctat atttaagcat atagaaagaa gatatttgac   2760

atttttatga tatgcttcat caataatatc agctaaattc atttttaatt cttttaaatt   2820

taaaatatct aaatgacaat gtgaatctac taaaattggc attttaaatc ctccatattt   2880

ttaaataaat atatagcata tatatttctt taaaagaaga ttaaaatctt tttttaaaga   2940

taaatttaga gaatcattca ttatataaat accattcaat aaataatcct tcaagaaata   3000

attctgtatt aaataaataa tctattttta taattttttt tctttctact aaataaaagt   3060

caataagata aaaccattga gataaagatt ttttttttgc taatttccaa aaaatagaat   3120

ttttttttt taaaattaat atatatatta aattataaac taattgtatt aaactattta   3180

ttattaatac aagatcaata tcttgaagtt tttttgtttg aaatattggt gtttttttat   3240

ctaaaaaatt ttgaaaaaca gaatttattt tttttaaata tccttttttt ttccaaattt   3300

ctaaataaat aggaccaaat ccagggatat taaaaatatt taataaattt ttagaattat   3360

taatttcata ttcccaaaaa aaattttttta aattttgatt tttttcttct aaaaagaaat   3420

tcatatacca aatttgacat cgactgcgta ttgtaagtgg tatagattct aaataatctg   3480

cagtcaatat taatatagtt ttttctcttt tttcttctaa aattttaaga aatgcattat   3540

acgcaaataa attcatatta tgagatttat ctataataac aacacgatat cctcctatcc   3600

aagatgtcct ttgaagaaaa aaaataatat ttcttatttg atctatttga atttgattta   3660

attttccttg gggttttata tataataaat caggatgttc agataattca ctgctattac   3720

atgaaagaat tttttgagca cacaatttta caaaatgtaa ttttcctgtt cctggaaatc   3780

ctgttaataa tagcccataa ggtattttat tattttgtaa atgccaatta aattttttcc   3840

aaagagtttt ttgccaaaaa aatatcataa taattatatt ttcgaaaaat ataaagaaat   3900

tataatcttt atttagaata aaaatataga ttttttattt aaaaaatata ttttaaaatt   3960

ataatatatt ttaaatataa aattaaaaaa tttttttaaa atttaagcac gtaactcaat   4020

tggttagagt atcattatga cataatgaag gttagcagtt caaatctgct cgtgcttacc   4080
```

```
ataaattatt atttaatcct caataaaatt gtgaatataa ttctttaaat tagatttaaa   4140
ttgaacaata ttaatgaata aatatatttt tcatttaaaa atgatgaaaa aaaattatag   4200
tattattata ctaataatta tatttgaata aaaatattta ttttgttgta atatatagca   4260
atgaaaatat ttaaaattta tcatgcaaag atatagattt tatagagaac ataaatttat   4320
aattccattg attaatgata taactagaaa aattgcttct actaatttcc aaaacaataa   4380
agaaatctct ttacttataa aaaaactctc taatttgcaa ttagttttaa caaaatattc   4440
agaacatgaa gataaagcat atcattcgtt attagtaaat aaaggatcta atatacatta   4500
tgatctagaa aatgatcata atgattatga aaaaaaattt tgtgatttaa aaaatttatt   4560
aaaaataata aaagatttaa aaaataaaaa agaaaaaatt gcatatggtt ataaatttta   4620
tttaaatttt agagaatttg aagttaaaaa tgctattcat atgaataatg aagaacttta   4680
tattatgcca aaattacaac aattatattc tgataatgaa ttacaagcta ttgaactaaa   4740
aacatataaa cttatgaaag ttagtgaaat cattcatatg atgaaaacta tttttatata   4800
tatggatgca aatgatagat tgcattattt taatgatatt aataaatctt ctccagaaaa   4860
aacaaaacct attttatgta gtattttaaa aataaaaaaa aataactctt atcttatttc   4920
taaaaaagaa aaagattttt tattaaatta tttttctatt tcaaaagaag aatataaaaa   4980
tattaatgta gaagataaaa ataaatattt atgggaatta tcagaagggg aatttataga   5040
agaaaatatg agtatgaaat cacaacatga tcctaccaga aaatattaaa ttcaattttt   5100
ctaaaaaata tataaaaaat aaatggattt ttacttaaaa ttaggagtaa taaatggata   5160
aaaaaatatt aaaaccttgt tatagaagtg attctatatt agatcataac caattgaata   5220
aattgcatga attaactcca attatttttg gagcaagtgc ttttcaatac ttaaatgctg   5280
gatctgaaat aggacttttt gaattattat attattctgg tccaaaaaaa aaatctgaat   5340
taatgataga actcagttta aaagaaagag ctatagatat tttattatta ggaaatacat   5400
ctctaaattt aattaataaa gaaaaatctt tttataaaaa ttctctaata atacaaacaa   5460
tttttgaaaa taatatttgg gatattttca aagatttgat tgcttttgag caatatattg   5520
tttatctggg gcaatttgat tttacagatt ctttaagaaa aaatactaat attggattgc   5580
aaagaatttc taatacatca aacagtcttt ataaaagctt taataaaaat aaaaaattag   5640
aaaaaatatt ctataattat atgaattcat ggacccgtct ttctaattat tatttaatta   5700
aatatattaa ctttaataat gttcatcgtt tacttgatgt tggaggagga acagcaatta   5760
atgctattgc tttagcaaaa aaatatccta aattaaaaat tactgttttt gaaatcgatg   5820
catctgcaaa aatagctcaa aaaaatattc aatcttctgg attatcaaat caaataaatg   5880
tcattcatgg tgatatattt aaagatcaat ttcctactgg atatgattgt gtactttttt   5940
cacatcaatt agttatatgg actcccgaag aaaatataga attattacat aaagcatata   6000
aaattttatc ttcccatgga ttagtaatta tttttaattc tatatctaat gatgatggaa   6060
aaggtccatt attagcagca ctagatagtg tatattttgc tagtattcct tcggaaggag   6120
gcatgattta ttcttggaat caatatgaag aatggttgaa aaaatcaaaa tttcaaaaaa   6180
tttctcgaat taattgccat cattggacac cacatggaat tataaaagca tataaataaa   6240
ttaagagata ttcaatgaat gaaaaagata cattaaaagg aagctatata ttttctgctt   6300
ctccaggaca agaaaggctc tggtttctta aagaattgaa tagtcaattc ggacctgcat   6360
ataatattcc tgctttattc aaaataaatg gatttcttaa tataatttct ttacaaaaat   6420
ctattaataa aatagtagaa cgtcatgaaa tattaagaac agcattaatt tatgatggaa   6480
```

```
caaaattatt gcaagttata aaacctaatt ttttaaaaac tattcgatat gtagattgca   6540
caattaaaga aaaaagaaaa aaatttttag aatcaagttt gatacaagaa tcatctgttc   6600
attttaattt tacacaacca ggaattttcg atttaatttt atataaattt caagaaaaag   6660
tatattatat attaatcaat atacatcata ttattagtga tggtatttca ttagaaattt   6720
ttgtatatga attatttgaa tattattatt ttatagaaaa taaaattaaa attaaaaaaa   6780
aagatttaga aatacaattt gctgattttg taaaatggaa tgaaaaatgg gtttccagct   6840
caaaatattt agaatacgaa ttattttgga aaaaaaaaca aaaagatttt gtattaaatt   6900
taacattacc taaaagaaat agaaatatag atacaattat cggtaataat gtaaattttg   6960
aactttctac ttctattata gatttattaa taaaagaatc aaagaaatta catgtttctt   7020
tatatgcatt ttatctttca atttttgcaa ttcttattta tttttttttca aatcaaaaaa   7080
aatttttaat tggaattcct cttgcaaata gaaaaaatca acaaacacaa aatattatgg   7140
gatttttagc taatacatta gttcttaata ttgctataga tttaaatcaa aatttatcag   7200
attttattaa aaataatcat aaaaatattt taaaacttat caagttagaa cgatttcctt   7260
atagttcttt acataaaatt tcaactaata atatacataa tagcgaacca atttttaaag   7320
ttatgtttgg ttatcaagaa ttagaaaata aaaaatttaa tataaaagaa ttaaatattg   7380
aaagaatcaa ttttaataca attttttcaa aatttgatat ctctcttttt atgtttcaaa   7440
aaggaaaaca acatagagga ttattagaat gtagatccca tatttttagt aaaaaagaaa   7500
gtgaaaattt ttatcgatat ttttctaata tatgcagaat tgcaaaaaat accaatattt   7560
taataaaaaa tattcagttt tatgaaaata atgatattaa atttgcaaaa aacttgttaa   7620
agaatcctga taatttatat cttaataaga aacttttaga aaaagtagta aattttaata   7680
taaaaaataa aaaattttct atattggatg caacgtataa acaagttcct attaatattc   7740
ctggaatatt atttatcaac catcacaata cttatcttaa agtaagactc acttatgata   7800
aaagattaaa tcttattgaa gataatgaaa aagatcaatc taatataata gagaataaat   7860
atcacgattt tataaaagca aattctaaaa ctgaaaaaat tttagaaaat atatggaaga   7920
gtttgctaag attaaattct tcactatcca ttcatcaaag tttttttttct ataggcggcc   7980
attctatttt agttgcgaaa atggtaaata atattaataa aaaattcaat attgtaattt   8040
ccataagaga tatattttttg catcctacaa tatctcatat cgctagtaaa attgaatctc   8100
ttaaagaaaa agaaatccat aatacaaata taaatcctca aaatttaaaa aaagaagata   8160
ttgtagaaat atataaagat attaatggaa aaaaaattta atttaaaata agaggtataa   8220
ttttgaaagg tttagatata aaaatattaa aaaaaaaaat taaatctgga aaaacaaatc   8280
taacacataa tcaacaaaga tgttgttttt ttttaaatat ggattctaat tttccatctt   8340
cagatgcata tttttttgaa gcaaatatat tttttgataa agcaatatta caacaaagta   8400
ttgcttttag cataacaaat tttcctattt ttagatctat ttttattaat atttttggat   8460
ctccaataag aaaaacacaa ttaagttcta ttatttccat aaaattagat aatctttatc   8520
aagataataa taaaattgat aaagtaaaat ggatctctaa taataaaaaa aataatacaa   8580
ttaatatatc ccaaggacca ttatttaata tattttgctt aaaacattct gataaaaaat   8640
tcaatattct ttttttagtt tcccgattag tttcgaataa aaaattaatt atatctttta   8700
tgaaaaatat atttttttaga tatcaaaatt ttttatatca taatgaaaat gaaaaaaatta   8760
tttcatatga aagaaatatt tcagaaaaat tcttttattt agaaaatcaa tggattgaaa   8820
```

```
cagaaaattt taaaaatcat attaaatttt ggaaaaaaga agttaaagat ttatctgact   8880
tagatttgca aacagatttt aaaagaccag aaataaaaac aaataaacaa aaatctgttt   8940
ttttaaagtt agaaaaatat aaaattttaa atatttttaa taaaatcaaa aaagaaaaat   9000
ataattatga agaatttttt ttatctatat ttgtaacgat tttatataaa tattctaata   9060
ataataactt tgctatagga cttaaagcta ataaattaga aaaatatttt gataaaaaca   9120
atatttctcc tattgaaaat gaattaccat ttaaaattaa tttaaattct agtttttctt   9180
ttaaaaaaat tctttcaata ataagcaaaa aatataattt atttttaagg tatagcactt   9240
tgcctataaa gattttattg gataaaatag gagtaaatag agatttaaaa aaaacacctt   9300
tttttcaagt atcttttcaa tatgaaaatt tttcttttcc tatttggaat aacaaaaaaa   9360
ataattttct aaaacaaatt cctattttag aaggaattaa tattatggat tttacatttt   9420
gtgcaataga aactaaatcg tcttttatat tacgtatcga ttttaatcca gatctttttt   9480
tagattcatc tatgattttt ttactttctg caatagaaga attattaatg tttatatcaa   9540
ataacagttg ggatatctct attagagatc tatctattat aagcaatatg atgttaaaaa   9600
aaatagaaaa aagatggaat gctcctaaaa aaatattgtt tgaaaatttt gaggttcaca   9660
aaaatttga aaatcaatgt aaaaaaacac cttcaaatat agctataata tgtcaaggag   9720
aaacaattac ttatagagag ttaaatgaac gagcaaatca aatatcacat tatttaatac   9780
acaaaaaatt attatttaat gaaaaagtag gaattcttat ggatagatca atagaattta   9840
ttatttccat attagcaatc ctaaaaataa attgtattta tgttcctata gatgaaaaat   9900
atcctattga acgtatcaat tatattatta atgatagtca aattaaatta ttaattacaa   9960
aaagttatat tcaaaaaaat aaaaatataa tatataaaaa tttaatttat ttagataaag  10020
attggccatt aattgaaata aaaagtagag aaaatttaaa ttttagtact aatatccaaa  10080
aaaatggcat gtatatgatt tatacctctg gatctacagg tcaacctaaa ggtgttattt  10140
taaatcattt tggagtatta aataatatta gttggagaca gaataaatgg aatttaaatg  10200
aaaaagatcg aatattatta aatacatctt ttagttttga tccttccatt tggtctattt  10260
tttggccatt actttttgga ggagcattta ttatagttcc tttatctata caaaatgata  10320
tttatgaatt aataaaatta ataaaaaaat ataatatatc tattattgga actattccac  10380
atattattga tttattagta tcaaacattg ctattagaaa ttgcaattct cttagactta  10440
ttttaagtgg tggtgaacca ttatctcaaa aaattgttca aaaagttttt aatcgtacaa  10500
atgctaaact ttttagttta tatggtccta ctgaaacaac tattgatgca ggaatttacg  10560
aatgtaaacc cgatgatatt gtgcaaacag caccaatagg aaaagcaatt gataatacaa  10620
gaatatatat tttagatgaa aatttaagac atgtaccaga tggagtaaaa ggagaaattt  10680
atatttcagg accaggtgta gctataggct atcataacag aaaagattta aatgcaaaat  10740
cttttcttaa agataatatt ttttattctg aattaaaata tatgtataaa acaggagatc  10800
ttggtgtatt ttgttatgat gataacatca aatttttagg aagaattgat aatcaagtta  10860
aaatacatgg aaataggata gaatgttcag aaatagaatc ggttttaata aatataaaaa  10920
aagttaaaga aagtgctgta atagtagaca atccttatac tgaaaaaact aaattaattg  10980
ctttttttagc agtatcagaa ttagatgtaa aaaaagaaga tattcaaaaa aaattaaaaa  11040
ataaactgcc aaaatatatg ctgccagata aaattatttt acttatatct ttgccaaaat  11100
tagaaaatgg gaaaattgat aaaaatgctt tatttcgaat ctataataca tcaaaaaata  11160
ataaaagcgc acttttagaa aataaattac ctaataatcc tatagaaaaa atagtattta  11220
```

```
aatatttttg tgatgtttta tctctttcca atattagtat tcatgatgat ttttttaaat  11280
taggtggaac atctatatta ttagcaagat tatcaaattt attattcaat cattttgata  11340
tttctttacc tcttcatcaa ttttttaaaa ttccaacggt tctaggtgtt tcaaatataa  11400
ttgttacctt gcaaaaagaa ggaattgata aagctctgct tgataagcat atctcaaaac  11460
ttgaagaaga tgcagagtta ataaaagata tttctccaaa aaatcttcct aaaggaaatt  11520
tttataatcc taaaaatatt ttaattactg gaagtacagg atatataggt tcttttattt  11580
tacaagaatt attaattaat actaacgcta ctatatattg tttgattagg tctaaaaatc  11640
ctgagaaagc tttgataaaa ttaaagaata aaatgaaaga attttatatt tggaaagaag  11700
tgtacacaaa aagaatagtt tgtttagttg gtgatctagg cgaaaaaaat attggattaa  11760
ataaaaaaat atgggaaaat ctatctaaaa aaatagaggt tatttttcat gctggcgctt  11820
tagtaaactt tgcttatcct tattctgctt taaaagctgc aaatgtagaa ggaacaaaag  11880
aaatttttcg attttcatgt aaaaaattat taaaatcagt tcattatatt tcaaccattg  11940
atgtgttatt agctactcat attcctagac ctttttttaga aaatgatgct cctttaaaag  12000
taagtattga tattcctgga ggatatactg gtagtaaatg ggttgcagaa aagatagcgc  12060
attctgcaat gatacgaggc attccaactt ctatatatcg tcctggacta gttatgagcc  12120
attcagaaac aggagcaact caaacaaatg attatctttt ggttgcattt aaaggtttta  12180
taccaaaaaa agttattcct gaatatgcaa gaatatttga tattgttcca gtagactttg  12240
tagctaaatc tatagtttat gcatcaatgc aaaaaaatgt acacggaaaa ttctatcata  12300
tttttaatcc aaagcctact actttatatc aattttgcaa ttggattaaa aattatggat  12360
attcgtttga tattattcca tttgaaattg gtagaaaaat tgcgttagat tctaaagaat  12420
ctgatcccct ttacccgcta gttccattaa ttagagatgc agatccaaat cctcacagac  12480
ctttagatcc taaatatatt aatgaagtgc aaccagaaat tgaatgtaaa aatatgaaca  12540
ctattttaca aaaaagtgga attatatgtc ctaatatgaa tgaaaaatta acacatttat  12600
gtttaaaata tttaataaat attggatact ttcctcatcc gaaaaaaata taaattttta  12660
aataaaataa attattaatg acatgtatat ttttttaaat ttataaatct tagcaaaatt  12720
caacaattca attatgaaaa aaatgattaa ttataaagaa catgaaatta caagttttgt  12780
agatataatt ttattgagaa gtcataccgt tccagataaa aagatgttga catatttaac  12840
atcttttgat gaaaaaaaag aactgactta taaaaaaata aataagattt cacaacaaat  12900
agctgtaaaa attttgcatt atctttctcc tggagataga gctttaattt ttcataaacc  12960
aagtattgat tatattacag ctttatttgg atgtttatat gcaggaataa ttgctattcc  13020
tgtttatgga ccagaacatg gaattaataa aaataaatta tatagactta aaaatattat  13080
aaaagattct ggtgcaaaag gaattctatt atcttataaa gaattaaaaa attgtcaaca  13140
tttttttct aatttttata tacataaaga aaaaatacat tatatcacta cagatgatac  13200
tagtaatatt gattttcaag attggaaaaa accgtatttt aataaaaatc atacttctat  13260
tattcaatac acttcaggat caacatctga tcctaaagga gttatgctta atcacactaa  13320
tttaatatcc aatatattat caattcaaaa tatatttgaa atgaaaaaaa acaaaggaaa  13380
agctgtaatt tggttgcctc catatcatga tatgggatta ataggaggaa ttttaacacc  13440
aatatttgta gattttccat taattcttat ttcaccatta ttatttattc aaaatcctat  13500
attttggtta aaattaatta gtatggaaaa agcaacaatt actggaggtc caaattttgc  13560
```

```
ttttgattta tgctctaata aagcaataat aagaaaatta aacaatatag atttatcatc 13620

tataaaacat attttttctg gtgcagaacc tattaatcca gaagtgatta ataaattttt 13680

cgaaatatat gaaaagtttg gattatctaa aaaatctttt agtacttgtt atggccttgc 13740

tgaaagcact ttaatggtaa caagttctaa aatagaaaat aacaaagaaa ttaaagaaaa 13800

agaattcttt tttaagaaaa atattgtaga agtttttaaa aaaaaccaaa aatcattttc 13860

attatctaaa aaattatttt cttgtggaaa aattattccc aatcataaat tagcaatagt 13920

tgatcctaaa aaatctaaga aactaaatga aaaagtcatt ggagaaatat atgtgaaagg 13980

tccatcagtt tctaaaggtt attggaaaaa tcctaaaaaa acaaagaata tatttcaaaa 14040

tttctttata aaagaaaata aaaaaaaatc ttatggatgg ttaaaaacag gagatttagg 14100

attcttatac aattctcaac tatatgttac tggtagaata aaagatttaa ttattattcg 14160

aggagaaaat ttttatcctc aagatattga aaattatgtt aaagaattaa attctaaaat 14220

tcaattatgc aattctgcgg catttgaaat tgacaaaaat catataaaag aagtagtttt 14280

attgcaagaa ataagaaaaa aaaatttatc tgaaaatttt gagaatcttg ctcttgatat 14340

aagaaaatct attttagata aattaaattt attaattcat aatataattt ttatagaaaa 14400

aggagcatta ccaaaaacca ctagcggtaa aatacaaaga tttttagcaa aaaaatatta 14460

tttaagtaat agttttaata taatattttc ttttaattct caattgaaag aaaaatataa 14520

aaaaattaat tatgtccaaa aatactatat tcaatcctta aagaaagaag aaaaaaaaat 14580

ttattattca ataataaaat ttattcaaag atatcaaaac ctcaataaag atattattaa 14640

tttcacaatt ttagaaattg gattagattc attgcatatg atggaattaa aaaatttttt 14700

agaagaaaaa tataaaatta ttttaaatat gcattctttt ttagaagata caaaaatttt 14760

tactttagta aaagaagttt ttaacaaaca taaggaaaat atacagaaaa tatatataaa 14820

aaaggaaaag aaaaaaaatg ttttaaaaaa tcaagtaagt aaatattttt ctgttgatcc 14880

tggaaaatca tcaatttatt ataattatct tgtacaaaaa gaaaattcta tatatgaaat 14940

tttcagaatt attaaaatat ctaaatctat aaatataaaa ttattagaaa aatctattca 15000

tatattgtta aatatgtatc caacattaaa aagtagattt atagtaaaaa atactggaat 15060

agtgtatcag gaatatcctg ttgaattatc cttttcttct atttttagaa aaataaattg 15120

taaagatata gatttaaaag aaacatgtaa tatcttttta aaagaacgtt ttaatatgga 15180

aaagggacca ctttttaata ttatacatat aaataatata aaacttgatt ataatattct 15240

aatatttaag attcatcata ttattgcaga tttttggtca ataattataa tttatcaaaa 15300

tattgaaaat atttataata atttattaaa aaataattct attaagaata taaaaatata 15360

tgaaacattc caagatgtac aaaataaaaa atataaaaaa tacattcaat ctaatcaatt 15420

tattgaagac aatctttttt ggaaaagata tttatctaaa tataatttat tagaaaatac 15480

aaataatatt aagagaaaaa atattcaatc atttcaattt aatttaaatt ttaattttta 15540

taacaattta ttaatttttt ctaaaaaaaa aaaaataaca ccttatacca ttttattaat 15600

tatataccaa attacatatt atcgaatata taaaagagat tattttatta ctggaactcc 15660

agtagcattg cgtgatgatt atcttttacg aaattatata ggatattgtg taaatatttt 15720

accaattgtt tcagattttt caaaacaaaa tgatatatat tcttttactg aaaaagttaa 15780

aaatgatatt aaaaatatat tacaacataa atatttttat ttttcaaaaa ttatagaatt 15840

attgaaattg cctagaaata cggattatat tccattattt aatagccttt ttatttacca 15900

aacagatcat ataggatctt ttcatttttt aaatacaatt gcagcaaata taaaagatag 15960
```

```
cgaatttcaa tttttaggat atccagcatc tatatggtat acaaataatt ttaatttaat  16020
gcatcatttt atttttaata tttctgtaaa taaagaatcc tattcaatta atattgaata  16080
cgatgaaaat atacataata aaatattaat aaaaaaattt tctgaacaat ttaaattaac  16140
atttcaagca attattttta ataaaccaaa agcaattata gaagaaaaac aatatttgtt  16200
ttatcaaaat ataaattcta ctaataaaaa attttttaaa tctcaatatt ttttagatca  16260
attgtttagg aaacaagtaa ttaaaaatcc aaatgcatca gcaataattt ttgatgacat  16320
aaatattact tataaaaaat tgaataaata tgttaataga gtttctcatt atttaataaa  16380
tcatatttta aaaaatgaaa ttcttattgc tattcttatg gaaaaaggaa tagaacaaat  16440
agttgcatgt ttagctatcc tatccatagg aaaagcttat ttacctatta atattaattt  16500
ttctaaaaat aaaattcatg aaataatggt attaggaaaa gtaaaaagat ttttaattca  16560
aaaaaaatat ttaaaaaaat ttaattttaa agattttcaa tcaattgatg taacatctat  16620
aattgaaaat tcttctttta aaaaatctca agaatatttt ccaaagtatc aattaagaaa  16680
attaaatgat cttgcttatg taatttttac atctggttca actggcactc caaaaggtgt  16740
aatgattgaa cataaacaag ttgtaaatac tattttagat ataaatgaaa aatttcaagt  16800
taataattta gatagaatat tagcaatatc taatttagat tttgatttat cggtatatga  16860
tatttttgga atattatctg ctggcggaac attagttatt gttccatcaa aatttacaaa  16920
agaaccaaaa tattggttat atgcaataca aaaataccaa attactattt ggaatagcgt  16980
tcctatgttt aaacaaatgt ttattgaata tttacaaggt atagataaag agagttttta  17040
taaaaaaatt aaattaaaat taattttatt aagtggagat tggattcctc tagatttgcc  17100
agaaaaaata tttaaaatat ataaaaagaa ttttgattct ttaaaagttg tatctcttgg  17160
aggagctacg gaatgttcaa tatggtctaa ttattttatt attaataaaa atattaaata  17220
taaaactagc attccttatg gcaaaccatt atctaatcaa catctatata ttttagacgc  17280
tttaatgttg ccaacaaata tattagttcc aggttattta tatataggtg gatttggagt  17340
tgcgagaggt tattgggatg atattaaaaa aacaaatgaa agtttttatt ttcataaaga  17400
aatagggaaa agaatttatt ttacaggaga tatgggacaa taccatccgg atggaaatat  17460
tgaattttta ggaagaaaag atagacaaat taaaattaat ggatacagaa ttgaactaga  17520
agaaattcaa aataaattaa aatctcatgt atatgtcaaa gattcgttta ttacagtaaa  17580
tcagaataat atttctgcaa aaattcttgc ttttattata ttacataata attcatcaat  17640
gatgtctcat acaaatataa aaaaggaact gaaatcattt ctttataaga atttatctga  17700
atatatgatt ccaaatcatt ttcaatttct taaaaaattt ccattaagta aaaatgggaa  17760
aatagatgaa aataagttat ataagatgca tgatattcca atattaaata tacaaaaatc  17820
tgcaaataca aaattgcaaa aatctttgaa agaaatttgg aaagatttat taaaaatcaa  17880
aaaagatata tatataaatg ataatttttt tcaattaggt ggatcttctc ttttagctgt  17940
tcgcatgaca aatttgatat caaaaaaatt aaatttaaat attgatgttt ctgctgtttt  18000
taaatatcaa acaattgaaa gtttagaaaa atttttacaa aaagacaaaa taaaaataga  18060
aaaaaataat attactaaac aagagcgtat cctatattat gaatagtatt agttctatat  18120
atttaaaaaa taataaaatt cttacagaaa aaataataaa aaaatgtatg ttaattagat  18180
tagttgaaga acgattattg caagcttttt cagaaggaga actttatgga acaatacata  18240
cttgcatagg acaagaatta ataggtgtta tggcttgtca atttataaat caaactgata  18300
```

```
caatttttc taatcatcga tgccatggac attttttatc atttactaat gatgtagaag 18360

gattaatttc tgaaatatat ggtaaaaaaa caggagtttg ttctggaata ggtggaagcc 18420

aacatttata taaaaataat ttttattcaa atggcattca aggaggtttt atgcctgttg 18480

cagcaggctt ggcatattct tttaaagaaa ataataaaat tgcaattatt tttattggag 18540

acggaacttt aggagaagga attctttacg aaacatataa tattattgct ttattaaagt 18600

tgccattact tattatttta gaaaataatt tatatgctca atctacccat caaaaagaaa 18660

cattatcagg agatatatta aaaagagctc aagcttttaa tatttatgca gataaatctg 18720

atatttggaa ttggaattca ttatataaaa aaatggaatt catgattaat tatgtaaggc 18780

attatagatc tccagcattt ttagaagttt cttgttatag attaaaagcc cactctaaag 18840

gagatgatga cagagatgaa aacgaaataa atttttataa aaaaaaagat cctgtaaaga 18900

ttataatgga tcaaattttt cataaattgc aaaaaaaatc tattatttct ttaataaaag 18960

aacgtataga aaatgctatt tataaagcaa aaaaagatgt atatgctaat tataaaatct 19020

atcaatataa gaattataat atctttaata actatcaaaa tttatatgtt cattgtaaaa 19080

aaaataaacg tatttctaca ttattaaata atacattaca taatctaatg aaagaaaata 19140

gtaatattat cttattagga gaagatatca aagatccata tggaggtgcc tttaaaataa 19200

ctaaaggttt atcttctaaa tttcctgata gagttattaa tactcctatt tcagaagctg 19260

ctattgttgg attttcttgt ggcatgtctt tatcaggttt gttgcctatt gttgaaatta 19320

tgtttggaga ttttattaca ttagcttttg atcaaatttt aaatcatgca agtaaattaa 19380

aatatatgta taattataat gtttcaactc cgataattat cagaacccct atgggtggtg 19440

gtagaggata tggaccaaca catagtcaaa ctttagaaaa gcattttta ggaattccag 19500

gcattcgaat ttttgcaata aataatttat ttaatccaga aatattatat aaatctatat 19560

taaagaataa tcaagaatta tcaattataa ttgaaaataa aattttatat acaaaaaatc 19620

ttttatcctt tcctttaaaa ggatatttct ataaattcaa agattatcca caacctacta 19680

taatgatgtt gcctaaatcc aatttaattg atattactct tattacatat ggaggattag 19740

tagatattat agttgaaata atagaagaat tatttgaaga acatgattta attgctcagc 19800

ttatatgtcc tatacaaatt tatccatgtc aattatctga attttctaat ttaataaaaa 19860

aatcgtcttt gatagtctta atagaagaag gacagggctt tgcaaatttc agcagtgaga 19920

tgctttctca gcttattgaa aatgataaat ttaaaaattg taatttctta agatgttctt 19980

cagaaccatc tccaatacca gcatcaatat atttggaaga taagatgctt ccaaataaaa 20040

caaatatact tcgtaatatt ttagagattt ataatgaaaa aaaaaatgtt aattccaaga 20100

tttgaggcaa atgataattc cgtaaaaatt attgaatggt tagttaacga tcgtgttttt 20160

attaaaaaaa atactccttt attaaatatt gaaacatcaa aaacttttca agaaattaaa 20220

agtaaatatg atggttttat aaaaaagatg tgtcaagaag gtgacacact tcatactgga 20280

gatatattta tagaatttta tacaaaatta gaagatcttt taaaaaaaaa tacttatttt 20340

aaaaaaaaaa aagatactgt tttaagctgt aaatctacat accaaaggtt ttctaaaaaa 20400

gcaaaaaaaa ttttattaga aaaaaatatt gatatatctt cttgcacaga agaattaata 20460

actacaaaag tattaaataa tattacaaat gaaatacgaa aagataaaaa aaataaagat 20520

ttaataaaat attttccaaa tttagaagtt aaaaaaaatt cagatattaa aaatcgagaa 20580

atttctgttt tagaaaaatc agatggaaat attttttcaa gctctattat gattcaatta 20640

tcttctgaaa aaattagaga aaatataaaa aaaataccta aattaaatgg acagattttc 20700
```

```
ccttatctta tgtattttta tatacaagaa ttatctattt caccaaaatt taccgcattt  20760
tatagagaaa aaaatattat ttattataat agaattaatt taggaatttt aatagataat  20820
aataatatat tgcaaattat tgttttaaaa gatgcaaata aattttcact attagaattg  20880
caaaacgaat taattgataa aatatgtaga tgttatgaaa ataatttaga aattgatgat  20940
gttgtacatt ctacaacaag tgtgtcggat ttatctggaa ataatattat atcttttcag  21000
cctataatta atcaaaaaca atctgttatc cttggcatag gaggagatac taatctttta  21060
ggaaaaccta taacttttaa tatagtattt gatcatagaa ttttaaatgg aaaggaagtt  21120
gcaatatttt tagaaaattt taagagaaaa atactacaag gaatatactg atagtaatat  21180
agatgtatat tataaacagt atataattgt tattatatat ctaatttttt acaatatata  21240
ctgtatatat gtataataaa tttgaagtaa ttattatagg agccggtcca tcaggtttga  21300
tgttatcaat agaactagct ttaagaaata tttcatgtgc tataattgaa aaaagaaaat  21360
ctagattaat tgaaacacgt gcatttggat taatgccatt aactttaaat ttattagata  21420
tgcgtggatt agctaattct atgatatcag aaggtataat atgtaactat gctcccttag  21480
gagatggaaa aggaaaatta tattttcatt cattaaaaac aaaatttcct tttttattaa  21540
gcattccaca agagaaaaca gaagaaattc ttgaaaaaag aacaattcaa ttaggtgtaa  21600
aaatttttaa taatcacgaa ttattaagat ttgaagaaaa aaatggagat tttttattat  21660
tttgtaaaaa taaaaaagaa gaaaatattt ttatatctcg ttatttaata gggtgtgatg  21720
gatcttatag cagcgtaaga aatttagcaa aaataccatt tacttttttta aaacaaaata  21780
aaacacttat gcatggtgat gtttatttaa aatatcctcc aaaagataaa atatttgcta  21840
aaacttctaa aagaggaatg attgccattt ttcctcataa aaatggatct tatagagcta  21900
ttgcactgga tcaaaaaaaa atgctaatac cagtaaatac aaaattaaca ttagaagatt  21960
ttacagaaag tttaacatcc ttatcaggag gttgtaactt tggtataaat aattttatat  22020
ggcttaaaag gtttagagtt caacaaaagc aatctcaaag ttatcaaaaa ggaaaaattt  22080
ttcttcttgg agatgctgct catactcata tgccagcagg agggcaagga ttacaagttg  22140
ctatacatga tgcgtttaat ctaggttgga aacttgcatt ttatatcaaa aaaaaatctt  22200
catataattt attatcttca tatacagaag aaagaagaaa aattaatgaa attgctatga  22260
aaagaagttc tatgttattt aaatatgaaa tagctaatga tatatttagc atgagtttaa  22320
agtggactat taataaatta ttttctttta aatttatgca aaaatatttt gcaaaagaca  22380
tgagtggatt gtctactaat tatcataaaa ttttttctaa aaaaaaaaat tataaaaaat  22440
ttaaatgttt gggatatttt attagagata taaaaattta tacacatgat aatacactac  22500
gtttttata ttcttttcta aaacaaggaa aatttgtatt tattagtata atgcatcaaa  22560
tttcttttat ttcatggaag aatacggata ttattttcct tgcttctgat gatataaaaa  22620
aaatatatgg aattaattgt tgtctagtaa ggccagatgg tataatttgt tgggctggat  22680
tagatacgaa aaagtttacc aaaaatattt tttatgaaat tattttttta aagcaagagt  22740
gattccatca gcaaatggaa gcaaactgat ttctactcta ttatcagata atagaaaatt  22800
attaagatca ttaattattt tagtatcagc attatattta atgttttgag atacagtaac  22860
ttttcctgac cataatgtat tatcaaataa tattaatcca ccagctttta ataattttaa  22920
agaatattca taataattaa tatagttttc tttatctgca tctataaata taaaatcaaa  22980
atactctttt ttatgcaata ataatttttt taatgttagt aatgcatcat taatatgtag  23040
```

```
agaaatttta tgattaattt tttctatttt ccaaaatttt ttagcaatat cagtccattt  23100
tatattatta tcacatgcta ttaattttcc attttcagga agagatttag caatacatat  23160
agaactatat cctgtaaaaa ctcctatttc taatgccatt tttgctttca ttaattttat  23220
taaaagagat ataaactgtg cttgttccgg aaaaatttgc atatttcttt ctggcaattt  23280
atttgttata tatctcaatt ttttaagagt atgactttct cttaaagaag tatttctaat  23340
atattgaaga atattttcat ttatctgaat gtgatttatc ataaaatatt atcctttaag  23400
aatttttaat cttaattttt taaatttttc tatttcttga acagccgaat attcattaga  23460
tcgtaaactt cctgatgcag gacctacaaa ttttccgcat acatatttat gtgcatgata  23520
tgcttttttt aaagaaatta taaaaatgtt atattttttt tgaattatag gataggaagt  23580
gaaatttaat tttcctatag atctcataca attttttacc ataaattgat gatctctcca  23640
atttaatcca ctcatttctg gttgtgaaat tggaggcata agagtaggtc ttacattttc  23700
attatatgat ttagaagaaa attctcctgt atagtataaa gcaacttctg ttgctttcat  23760
aagttttata gcattattta aatataataa agattgtaaa aacttttttt tagaatattc  23820
aaaaataaaa cattgtaaag atataataag accttgtatt attatcataa aaagataatg  23880
accatggatc catcttttgt atgcattata tttatctgta taatttttaa tttttaattt  23940
tgaataaaat ttattagaaa ttgaacaatg ggtattagga ttgtataaaa ataataatgt  24000
aaacaatgtt tttattaaaa tattaaaatt ttttcttgaa agggatgttc cacttttttt  24060
taaatctaaa aaagtaaatg atatgttttg ataactgagt aatttaatac ttctaatatt  24120
ggcccatcta ctcgaattat acgaaaagca agatcattat catgattttt ttttgattca  24180
taacaatcat tagaaataat agaaaaattt tttatttttt tttcatatga ttttaatatt  24240
ttctgtatta ttataaataa atcattttta tgtataattt cagaaaaact atttttttaat  24300
aaaatagtat ttttagaatt ttgtaaaata attaattctt tttgagaatg cggcaacttt  24360
tctgggggta aaagtaaaaa attatttttc aacataaata tattcactcg tattatataa  24420
ataataaaat atattataat ttaatatatt ttcctaattt ccaaaatttt aacatattat  24480
tatagttttt ggaaaaaggg tttcctgatt gtcctaaagg acatataaaa caacttttat  24540
tttttttatt taaatcaatt atttgtctat atacaggtcc agctttttga ataaaatttt  24600
catcatatgg agatgcatta atagtatagg cattaccttc tgtagatatt tttctattcc  24660
ataaatattt aattccccat attttaccaa aaataggatt aataaatttt gcttggtgga  24720
ttctccccca tttccatttt tctatattat ttcctaatat atttttaata ttaattattg  24780
cttttttaaa taaaatatac agaacatcag taatattttt ttttttattt aaacaaataa  24840
attttccgtt ttttttaat tgatcaataa taaaaagagg atttggaaaa ttttgataat  24900
ttataggtaa tttaggttgt atttttatta tttcttgaaa ccaaaatgaa aatactgtag  24960
cagaaatact attacttgac atatttccat tccatttttt aaggtatact aatatttttt  25020
tttcaaattt gttttgagga attattttta ataagaaatc ttttaattca taccataata  25080
agttatttgt atttatttga atatctttca tatttttat tgtcatttta ttcatattat  25140
taatcatatt ttcaattttt tcagcacggt atggaggacc tttccaaata taagtgagat  25200
tataaggata ttcattcgga ataattttgt tatttgcatt aacaatatat cctttagatg  25260
gattaaatac atgtggcaat ttattaaatg gaataaattc attccaagca ttttttgaat  25320
taaatggtat aacatatttt aaattttctt tttttcgaat aggtatcctt ccaggaaggt  25380
aatatccaat attccctaaa atatctgcat ataaaaaatt cattggagct gctgtaaaat  25440
```

cttttaaagc atttttaaat tctttccaat tagaggcgta atttatttct attaaacttt 25500
gaatagtttt atcgtcagaa tctaatcctg tccatcttat agctattttt tggtttatta 25560
tttttttatt tatttggtta ttttcttgaa ttaaattatt aataatagga ccaatatcag 25620
ataattcaat ttcgtgttgt atagtttttt tttttcttac tttgattttc tcaaaaattt 25680
tttttgtagg tcttgtctta tcaattaaaa ataaatcaga acaatctagt cctgcatcag 25740
ttattcccca agcaatattt ttattttctc ctgaaataat gcaaggtata cctggaattg 25800
aagaacctct aatgtttaaa gatggacctt gtatgttagc taaataacaa atattagggg 25860
aagataattc taaatgaata tcatttgcta atattggttt gcctgatttt gttaattttc 25920
ctgaaacaac ccatccgttt gatcctttgc ctggtaaatt ttgaatatta agattatttt 25980
gtatctcttg agagatatta ataaaagatt gcatattatt attatataat acttgatttt 26040
ttttatttgt atttaaatta tctgaagatt tttgtgtata atctaataaa ttgctgttgt 26100
ttaattcttc tatgtttaat gttgttggtg cgttttctgg atattgaatt ctaatatctt 26160
caatatttat atcagaggat ttttccataa taagggaatt atttaattta tcttgccaag 26220
tatgatattg taattgccaa gcaattattt ttgaccaaat aaatgaatct atatttttcc 26280
aatattttgg tttatagaat aatattctta attctatagg tcttttccca gatttaatat 26340
atgcatttac tcctgctgta tatccattaa taatttttttt tgttttaata ttaaaatgtt 26400
tccagttctc ttttgcacat cgataaaatc cccatgtttt taaatatttg tcttccttta 26460
tagttctttt cccaaaaatt tcacttaatg ttcctgaagc aatatgacgc tgtaattcca 26520
tttgccaaaa tctatctttt gcatgcatat atcctaatcc gtaaaaagca tcaatgtcat 26580
ttttagaagc aaaaatatga ggaattccat aactatctaa attaatttgt atttttccat 26640
acagaccttg aattaataaa cttttttttg aatttagcat atattttttta taaaaatatt 26700
atattatttt tataataaat ttaaatagta tttaatacta gttttattaa tacatttcgg 26760
aaaactatag tagttgttta gaaaataact aaaaaaatatg gtaccgagag cgggatttga 26820
acccgcacaa tctttacgat tattagattt tgaatctaac gcgtctgcct aatttcgcca 26880
tctcggcatg atttttttaa ttagcatttt tttttaaaaa taatttctgt attaaaattt 26940
ctttaatttt tttgggatta gctttttttat ttttttgtat tattttacca aataaaaaaat 27000
ctaaaatttt tgttttccca ttatgatatt taataatctc ttttggaaaa ctatcaatta 27060
cttcattaac agtttttttct attatattta tatcattaat ttgcaataat ttttttttat 27120
ggataatatc atcaatatga gattttccat ttgtaatcca taaattatca aaaactattt 27180
ttgctgtttt attagataat aattttttttt taattttaaa aataatattt gataaatgat 27240
gtatttttat aggagaatct ataaatagata gtttatattt ttttagttta gataataaca 27300
ttgatgtaat ccaattagat gctaattgag agttttctaa acctacagaa aaaactaatt 27360
tttcataaaa atttaataat tgaggatttt caagaaacat ttcgatttct ttcttatcaa 27420
gataatgttc taattttaaa cgatttcgta ttgaattggg caattcaggt aataataaat 27480
gaattttctt tatataagaa tatgttattt taacaggtaa taaatcaggt tcagggaaat 27540
atctataatc atgttcatgt tcctttatac gcattttttt agtaatattt tttttttgaat 27600
caaaaagacg agtttcttga attataaatt ttccagattc taataatgcg atttgtcttt 27660
ttgattcaaa aataatagat ttttcaataa atttaaaact atttaagttt ttacactcag 27720
tttttgtacc taatattgaa gatcctaaag gactaacaga tatatttaca tcacatcgaa 27780

```
attcaccctt ttccatattt gcatgtgata tttttaaata tcgtactaat aaatgcaatt  27840
cttttaaaaa agaaattgct tcttttgcag atgtaatatt tggttttgtt acaacttcta  27900
acaaaggatt tccagatcga ttaaaatcaa tttgtgcatt ttttttgta tgtactaatt  27960
ttcctgcatc ttcttctaaa tgagcatgat gaataaatat ttttttata tattttttag  28020
aatcattaat agcaatagga atatatcctc ccatcaaaat aggtattttg ttttgactaa  28080
tttgatatcc tttagacaaa tctggataaa aatagttttt tcgaacaaat aaaaaatatg  28140
taggtatttt tgcattaatt gctaaaccta atcttatagc aaattctata gcacgtttat  28200
ttaatatcgg cagggttcct ggtaatccta aatcaatacc cgatacttga gtatttggag  28260
cgtttccata ttgatttttc gccttagaga atatcttgct ttcagttgat aattggatat  28320
gaacttcaag accaattgca atattccatt ttatcataaa actttaccta taaaatattt  28380
tgaggttttt gcatatgcca atcagtattt aattgaaatt gatgcgctat atttaataat  28440
ttttcttcag tgaatgcagg acttataatt tgtaatccaa ttggtaattt ttttacaaat  28500
cctgctggta tagtaattcc aggaagccct gccatattta aagccaaagt atacatatcc  28560
gaaagatata ataatgaaag atcgttttta ttttttccaa ttttgtatgg taaaattggg  28620
ctagtaggac ccataattac atctaccttt tcaaaagctt tttgaaaatc ttgaaaaatt  28680
aatcttcgaa ttttttgtgc cttaatataa tatgaattat aaaattcaga agaaagcata  28740
aatgttccag ctaaaattcg ttgttttaca atttctccaa atccttctcc tctcgatctt  28800
tcataaagat cccatagatt ttttggattt tgacatcgat atccaaaacg gattccatca  28860
tatttagcaa gattagatga agcttctgct tgtgctataa tataatatgc agaaatacat  28920
atatcattat gtttcattcg aatcgatttt aattttgctc ccatagattc gtattttttt  28980
aaagcatgtt gaatagttag ttcaatttta ggatccaatc cttttgaaaa ataatcttct  29040
ggaattccta tttttattcc ttttatagaa ttattaagta ttttagtaaa atcttttttta  29100
tgtgcaaaag aagatgtaga atcttttttta tcgtatccag aaataatatt aagtaataat  29160
gcacaatctt ctgctgaatt tcccatagga cctgcttgat caagactgga agcataagca  29220
attattccgt atcttgatac taaaccgtat gttggtttta aacctgtaat gttacacata  29280
gaagcaggtt ggcgaataga tcctcctgta tctgttccag ttgctatggg agttaaatta  29340
gcagatatag ccgcagcaga accacctgaa gatcctccag gtattctaga taaatcccaa  29400
ggattcttac aaggtccaaa ataactagat tcattagaag aacccatagc aaattcatcg  29460
agatttgttt ttcctaataa tactaaacca gactttttac aaagttttac tatgtgtgca  29520
tcataaggag aaataaaatt ttttaacatt ttagaagcac atgtagtttt tattcctttg  29580
gtacatatta aatctttatg tgctatagga attccagtta aaatattggc tttgccatct  29640
gctatttttt tatctgcata ttctgcttgt tttaaagcat gattatatgt aattgtaata  29700
aaacaattta atgttttatt atatttataa atacgatcga gataatactt tacaagttca  29760
acgctactaa tttttttttgt ttttaaagcg tttgaaattg atttaagaga atgatattct  29820
atcactttta tttattttcc ctaaataata cataatacaa ttttaattat attttcctta  29880
ttttgataaa aatgtaggaa ccaaaaataa tttattttca tgatctatag aaggagcatt  29940
ttttaatata tatttattat caaaatcttt tttaatagga ctgtcttctt gtaaaatttg  30000
agttttattt gaaatattat acaatggttt aatattatta gtattaatta atgaaatttt  30060
attcattaca ttaagacaaa tatctaattg tttttttgtt tgcaaaattt ctttattatc  30120
tatttttaga caagattttt tggataattt tttaatttct tctgtagtta aatacatttt  30180
```

```
atacataaaa taaaaaattt gttatttaaa taaaattaaa atatcataat atccaaaatg  30240
gataatattt caatttataa ttgactaaat taatgttaac tggaaacaaa gatattttat  30300
caaataattt taatattttg aatataattt tcttttgata taaagaaatt ttatttcaag  30360
attaaaaaat tggaggtaaa ttatggatat tttacaaaat gctaaagaag ttttattgtt  30420
ttccaacaat ttaacggaaa atgatattca aaaagaaatt aatattgcta tgtcatacaa  30480
tatagatttt atagatttat atttagaaaa atctgaaaca gaaaattgga ttttagatga  30540
taggattatt aaaacaggat attataatat ttcacaaggt ttaggagtta gaactttttt  30600
aggtgaaaca agaggatatt cttatgcaga tataataaat attaattctt taaaagaaag  30660
tataaaaaaa gcaaaaaata tatcttcatt tcgaaaaaat attaaattaa attattttaa  30720
taatattaaa aaaaatcatt gtgtatatat ttctaaaaat cctattgaag aatataaaca  30780
atttcaaaaa atttcttttt taaaagaaat agataaatat attcgcgaaa aaaatgcaaa  30840
cattattcaa gttatagttc aattatatag ttctttaaaa acaattttag ttgctgcttc  30900
tgacggtact tttgcagcag atatgcgtcc tatggttcaa ttgagaattt ctgttatttt  30960
acagataaat aataaaatag aacaaggaaa tgcaggaata ggaggaagat attcttatag  31020
agttttattt aatcctaaaa attggaaaaa aattgcagat gaagcaattc gaatagcatt  31080
aataaattta aaatctatac ctttatcagc tggattgatg ccagtagtat taggatctgg  31140
ttggccaggt gttttgttac acgaagctgt tggacatggt ttagaaggtg attttaatag  31200
aaaaggtgtg tcaaatttta gtcaaaaaat gggaaaatta attgcatctc cattatgtac  31260
tgttatagat aatggaacta tcaaagataa aagagggtct ttaaatattg atgatgaagg  31320
tacggaaaca aagaaaaata ttttaattga aaatggaaaa ttagttggat acatgttgga  31380
taaacataat gcattcttaa tgaaaaaaaa atcaacagga aatggaagaa gggaatctta  31440
tgcacatatt cctatgcctc gtatgacgaa cacttatatg ttacctggca attatgaatt  31500
acaagaaatg atttcttcta ttcaaaaggg aatttttgct gtaaatttta atggtgggga  31560
agttgatatt acatctggaa aatttgtatt tgttatgtct gaagcttatc ttattgaaaa  31620
aggcaaagta acaaaaccat taaaaggagc tactttaatt ggagatggtc cttctataat  31680
gaaaaaaata tctatggtag gcaatgattt atcttttgat ttaggaatag gtatttgtgg  31740
aaaaaatgga caaaatatac cagtaggagt aggacaacca agtttaaaaa tagatgaaat  31800
taatatagga ggaacaaaaa taaaataaaa aatgaattaa tatcaatctc gatttttata  31860
aactattttt gtatagtatc ttactaagaa tttagatcta aataaaattt aatttattta  31920
attatttaaa tgtattaagt tttccaataa acaaatatca atggtgaaaa ttatgataag  31980
atcaaggaat atctttttaa tcggtatgtc aggtgtaggg aagagtacaa ttggcaaaca  32040
acttgctaat gaactaaaaa tggtatttta tgactcagat gaaattattg aaaaacgatg  32100
tggtgcggaa attagttgga ttcttgatat agaaggtgaa gaaggattta gaaaacgtga  32160
aagcgatatt atttatgagt ttactgaaaa aaagggcatt gtgttagcaa caggtagtgg  32220
agtagttttg aaaaaatcta attgtaatcg actttctgct cgtggaacag tgatatattt  32280
aagagcgtca ttaaaattgc atgttgaaag atcattgcgt gataaaaaaa aatatctaat  32340
acaaaaacaa aatcaagaaa tagaattgag aaaaattcaa gaaaaaaggg atcccctata  32400
taatagaata tctgacataa ttattgatgc taattctagc agtattcgtt ctattgttaa  32460
taacatttta gataaattaa atgaaaaata ataaaacgaa tatagattaa ataaaatata  32520
```

```
tagaatatac aattattttt aaaaaaataa gagagaactc tcttattcat attactatga  32580
taaataatat tattagaatt ctctctataa ttctatgtta gatatatata aattaaatgt  32640
aaaataaatt tgaaaaatta gtttaaaata tacattattt attttaatag attaaaatga  32700
ttttttgtaa ttcaatttcc tttagtacgt tcatgacgtt cttttgcttc tttagcttga  32760
attgataaag tagcagttgg ccttgctaat aatcttttaa taccaattgg ttctccagtc  32820
tcttgacaat atccgtatgt accattttta atattttcta tggatttttg cactttttgt  32880
aataatttag attgtctttc cacagtcttt aaaaaaatct gttgcatttc ttgttttgtt  32940
gcaagatcag aaatatccga gctattttca ttttcagaaa gtctttttct tgtttcagaa  33000
atggataaaa taagatcttt tttttgttgg cataaaattt tttcaaaaaa ttcatattgt  33060
ttttgattca tatatgaatc tttagacata tttaacagtt cagtttttgt cagcattaat  33120
attcttaatt taaaaaaaat ataaaattta gcagatattt ataaaaaata aaaatatctt  33180
taataaaaaa attaaatatt aatttatttt gattattaat ttttattatt tatttttatt  33240
tttataaaaa ataactataa caccaaataa aataattatc cctcctaata aatttttcca  33300
tgatggtatt ttttttaaaa aaatccattc aaaaattata gataaaaaag gcacaaaata  33360
caaagaattt gctactactc ttctttgaag atgatttaaa caaaaactcc ataaagtgta  33420
agctaatgca ccaggaccaa ttccaagtaa aatgatagat attagttctg ttttgggagc  33480
atagtatatc tcttttattg caataggagc agaaaaagac atcgcaatag ttgcaaacca  33540
aatacaccat gaagttatct ctaaaggaga taattttttt aaaagtggtt tttgcattat  33600
agtataaaaa gcaccacaca atgcagaaaa acataagtat attacgccat aattaataga  33660
tttagattga ataaagatca tagtaattcc taccaaagaa ataaatatac ctatccaccc  33720
catagtatta attttttcat ttaaaaagaa aaaggttatt atagaaacaa atatcggtat  33780
aagactaata ataaaactag ttatggttgg atctactgtt ttttctccta aattaattaa  33840
tatagtatac attccaatac caatacttcc ggttattaat agcaaaaata tatcgtattg  33900
ttgaagaaca tattttttag gaattaagaa aaaataccat gggaaaataa ataaagatgc  33960
aaaaaagaat cgaagaaatc ctatagattc tggatgaaaa tagtttaatg tgtctttaat  34020
tcctacataa gagagagacc acattattat aacgcaaact aaagcaatat aagctattat  34080
atttttaaaa aaaaggaata tcattttatg aattatatta aaaatatttt ttaaatcatg  34140
cataataaaa atatattttt caagaaatta atgcattaaa aaaaataaat tgataaaaat  34200
attatattaa ttataaacta ttataattta agtactgttc tttaataaag ttaatttaag  34260
tatggatgtg aaataaaatt gaaaaatgat attatagttt ttgatgtttc taatttattt  34320
tatatttctg cttatagatt gacaaaaaaa aaaaaaatat taaaaataat aattataata  34380
taaatacaat ttatagtaat gctattcaat ttatgagaaa attatattat ttttttaaat  34440
ctaaacatat aatatttgca tgtgatagca cccaatatta ttggcgaagt aaatattttt  34500
ctgaatataa aaaaaataga aaaatgacaa ctttaagaaa aaatgtaaga aactcaataa  34560
aattttttaa agaaaaaaat tttaaattat gtattgaagt tcctggttgt gaagcagatg  34620
atattattta ttgtttgata aattataaaa ttcataataa tataattatt gttagttctg  34680
atagagattt tatacaattg caatctacaa gagtacgatt atttaatcca catacatata  34740
aatttcgtaa aattcctgaa aaattagaat atgaattatt tataaaatgt atacgaggag  34800
atgtttctga taatatccca tctgcttatc cgtatgtaag agaatctcta ataaaggaag  34860
catattataa tccatctaaa tttttttattt ttatgaaaaa aaaattatct gataatattg  34920
```

-continued

```
cagtatacaa aaaatatcaa agaaatcgat tattaatcga tatgaaattt ttaccaaaaa  34980

aatatatatc attaattaaa atattgatag ataaattatc tttaatagaa gattaattat  35040

aatgttcatt acaggaaaaa tatctaaaat agaaaataaa attgatgaat ttggtaaaat  35100

agattacttt cttttttgg atgaaaaaaa aatttttctt aacaattttc tcggaaaata  35160

tatttcatta gaacacataa aaaatttaat tttttgtata ggatgtcaaa aaaaaatgaa  35220

agcatggtat agaaataatt attgtttttt atgcaataaa aaactagcta tatgtgatat  35280

ttgtataata aaaccagaaa aatgccattt tcatttaaat acctgtcgtg aaccagaatg  35340

gggatggaaa tattgtatga atatacatta tgtttatctt tctataactt ca          35392
```

BIOSYNTHETIC PATHWAY FOR HETEROLOGOUS EXPRESSION OF A NONRIBOSOMAL PEPTIDE SYNTHETASE DRUG AND ANALOGS

CROSS-REFERENCE TO RELATED APPLICATIONS

This application is a U.S. National Phase of International Application No. PCT/US2011/032796 filed Apr. 15, 2011, incorporated herein by reference, which claims priority of U.S. Provisional Patent Application Ser. No. 61/324,639, filed Apr. 15, 2010, the disclosure of which is incorporated herein in its entirety.

STATEMENT OF GOVERNMENT INTEREST

This invention was made with government support under Grant Numbers 2R01DC04173, 3R01DC02148, 1 R01 AI080935-01, and 2RO1CA085419, awarded by the National Institutes of Health (NIH). The government has certain rights in the invention.

SEQUENCE LISTING

This application contains, as a separate part of the disclosure, a Sequence Listing in computer-readable form (filename: 45345A_SeqListing.txt; created: Apr. 15, 2011; 200,632 bytes—ASCII text file) which is incorporated by reference in its entirety.

FIELD OF THE INVENTION

The present invention is directed to the biosynthetic pathway for a nonribosomal peptide synthetase (NRPS) drug and analogs thereof. The invention also discloses polynucleotide sequences useful for heterologous expression in a microbial host for the synthesis of the NRPS drug.

BACKGROUND OF THE INVENTION

Nonribosomal peptide synthetases (NRPSs) are large multidomain enzymes responsible for the biosynthesis of many pharmacologically important bioactive compounds of great structural diversity [Marahiel et al., *Chem. Rev.* (Washington, D.C.) 97: 2651-2673 (1997); Schwarzer et al., *Nat. Prod. Rep.* 20: 275-287 (2003); Cane et al., *Science* 282, 63-68 (1998)]. Prominent examples are the antibiotics penicillin, vancomycin, and actinomycin D, the immunosuppressant cyclosporine A, the siderophore enterobactin, and the antitumor drug bleomycin. NRPSs are organized into distinct modules, each of them responsible for the incorporation of one amino acid into the nascent peptide chain. A module can be further subdivided into catalytic domains, which are responsible for the coordinated recognition and activation [adenylation (A) domain] [Stachelhaus et al., *Chem. Biol.* 6: 493-505 (1999)], covalent binding and transfer [peptidyl carrier protein (PCP) domain] [Stachelhaus et al., *Chem. Biol.* 3: 913-921 (1996)], and incorporation [condensation (C) domain] of a certain substrate amino acid into the peptide chain [Stachelhaus et al., *J. Biol. Chem.* 273: 22773-22781 (1998)]. In addition to these so-called core domains, optional domains catalyze the modification of incorporated residues, i.e., by epimerization (E) or N-methylation (MT) domains [Walsh et al., *Curr. Opin. Chem. Biol.* 5: 525-534 (2001)]. Product release is normally effected by a thioesterase (Te) domain, catalyzing the formation of linear, cyclic, or branched cyclic products, representative for the class of NRPSs [Trauger et al., *Nature* 407: 215-218 (2000)].

Because of the modular organization of NRPSs and the colinearity between biosynthetic template and product, the NRP assembly line mechanism accommodates an enormous potential for biocombinatorial approaches. Crucial for such approaches is a profound knowledge about the substrate selectivity of catalytic domains and the determinants of selective communication between modules. In this context, little is known about the intermolecular communication between NRPSs within the same biosynthetic complex [Hahn et al., *Proceeding of the National Academy of Sciences* (*USA*) 101 (44): 15585-15590 (2004)].

ET743 (Trabectedin) is a tetrahydroisoquinoline natural product with potent activity as a chemotherapeutic originally isolated from the tunicate *Ecteinascidia turbinata* [Zewail-Foote et al., *Journal of Medicinal Chemistry* 42: 2493-2497 (1999)]. This drug has been commercialized by PharmaMar in Europe as Yondelis® for patients with soft tissue sarcoma and a new drug application has been filed with the Food and Drug Administration after completion of a Phase III clinical trial with coadministration of Doxil. Improved clinical outcome was observed as compared to Doxil alone [Chuk et al., *Oncologist* 14: 794-799 (2009)]. ET743 has been found to have a unique mechanisms of action including low nM cytotoxicity [Izbicka et al., *Annals of Oncology* 9: 981 (1998)], sequence specific alteration of DNA transcription [D'Incalci, *The Oncologist* 7: 210 (2002); Minuzzo, *Proceedings of the National Academy of Sciences of the United States of America* 97: 6780 (2000); Seaman et al., *Journal of the American Chemical Society* 120: 13028-13041 (1998)], and induced DNA breakage [Takebayashi, *Proceedings of the National Academy of Sciences of the United States of America* 96: 7196 (1999)] attributed to the ability of ET743 to alkylate the minor groove of DNA [Pommier et al., *Biochemistry* 35: 13303-13309 (1996); Zewail-Foote et al., *Journal of Medicinal Chemistry* 42: 2493-2497 (1999)].

Obtaining sufficient amounts of ET743 has presented a challenge since it was first isolated in 0.0001% yield from the natural source [Rinehart et al., The Journal of Organic Chemistry 55: 4512-4515 (1990)]. Aquaculture has proven to be viable [Fusetani N (ed): Drugs from the Sea. Basel. Karger. 2000. pp120-133. Chapter: Dominick Mendola Aquacultural Production of Bryostatin 1 and ecteinascidin 743; Fusetani, Drugs from the Sea. (2000); Carballo, *Journal of the World Aquaculture Society* 31: 481 (2000)], although not an economical method for supplying ET743 for clinical trials and commercial use [Cuevas, *Natural product reports* 26: 322 (2009)]. Total synthesis of ET743 was first reported [Corey et al., *Journal of the American Chemical Society* 118: 9202-9203 (1996)] and further routes of synthesis have been published [Endo et al., *Journal of the American Chemical Society* 124: 6552-6554 (2002), Chen et al., *Journal of the American Chemical Society* 128: 87-89 (2005), Zheng et al., *Angewandte Chemie. International edition in English* 45: 1754 (2006), and Fishlock et al., *The Journal of Organic Chemistry* 73: 9594-9600 (2008)]. Commercial production by PharmaMar has used a semi-synthetic scheme in which cyanosafracin B is transformed into ET743 over eight steps [Cuevas et al., *Organic Letters* 2: 2545-2548 (2000)] as safracin B can be cultured on the kilogram scale from the wild-type producer *Pseudomonas fluorescens* [Ikeda, *Journal of Antibiotics*. Series B 36: 1290 (1983)].

The similarity of ET743 to three other bacterial derived natural products, safracin (*Pseudomonas fluorescens*) [Ikeda, *Journal of Antibiotics*. Series B 36: 1290 (1983)], saframycin (*Streptomyces lavendulae*) [Arai et al., *Cellular and Molecular Life Sciences* 36: 1025 (1980)], and saframycin Mx1 (*Myxococcus xanthus*) [Irschik, *Journal of Antibiotics*. Series B 41: 993 (1988)] has been put forth as evidence that ET743 is of prokaryotic origin, likely from a bacterium that is closely associated to *E. turbinata* [Piel, *Current Medicinal Chemistry* 13: 39 (2006)] (FIG. 1). Evidence for such a "symbiont hypothesis" has been generated for a diverse set of natural products isolated from macroscopic sources including bryostatin [Lopanik et al., *Oecologia* 139: 131 (2004); Sudek et al., *J. Nat. Prod.* 70: 67-74 (2007); Lopanik et al., *Chemistry & Biology* 15: 1175 (2008)], rhizoxin [Partida-Martinez, *Nature* 437: 884 (2005); Scherlach et al., *Journal of the American Chemical Society* 128: 11529-11536 (2006); Partida-Martinez et al., *International Journal of Systematic and Evolutionary Microbiology* 57: 2583-2590 (2007)], and onnamide/pederin [Piel, *Proceedings of the National Academy of Sciences of the United States of America* 99: 14002 (2002); Piel, *Proceedings of the National Academy of Sciences of the United States of America* 101: 16222 (2004); Schmidt, *Nature Chemical Biology* 4: 466 (2008)].

SUMMARY OF THE INVENTION

A common biosynthetic logic has been elucidated for the three known tetrahydroisoquinoline pathways, and was used to identify an ET743 biosynthetic scheme (FIG. 2). All three described biosynthetic pathways [Velasco et al., *Molecular Microbiology* 56: 144 (2005); Li et al., *Journal of Bacteriology* 190: 251-263 (2008); Pospiech et al., *Microbiology* 141: 1793 (1995)] consist of three nonribosomal peptide synthetase (NRPS) modules and numerous tailoring enzymes [Fischbach et al., *Chem Rev.* 106: 3468-3496. (2006)]. Each module contains one of the three core domains, an adenylation (A) domain, a condensation (C) domain, and a thiolation (T) domain, that act in concert to polymerize amino acid building blocks through amide linkages. Two of the three pathways are initiated in an uncharacterized manner by an acyl ligase (AL) domain and T-domain. All three NRPS trimodules are terminated by a rare RE-domain, which utilizes NAD(P)H to release the enzyme bound intermediate in reduced form as an activated aldehyde [Kopp et al., *Journal of the American Chemical Society* 128: 16478 (2006)]. Disclosed herein are polynucleotide and polypeptide sequences derived from the microbiome of *E. turbinata* that are involved in a biosynthetic pathway to synthesize ET743.

Accordingly, the present disclosure provides a protein comprising the polypeptide sequence of SEQ ID NO: 1 (EtuA1), the polypeptide sequence of SEQ ID NO: 2 (EtuA2), the polypeptide sequence of SEQ ID NO: 3 (EtuA3), the polypeptide sequence of SEQ ID NO: 4 (EtuD1), the polypeptide sequence of SEQ ID NO: 5 (EtuD2), the polypeptide sequence of SEQ ID NO: 6 (EtuD3), the polypeptide sequence of SEQ ID NO: 7 (EtuF1), the polypeptide sequence of SEQ ID NO: 8 (EtuF2), the polypeptide sequence of SEQ ID NO: 9 (EutF3), the polypeptide sequence of SEQ ID NO: 10 (EtuH), the polypeptide sequence of SEQ ID NO: 11 (EtuM1), the polypeptide sequence of SEQ ID NO: 12 (EtuM2), the polypeptide sequence of SEQ ID NO: 13 (EtuN1), the polypeptide sequence of SEQ ID NO: 14 (EtuN2), the polypeptide sequence of SEQ ID NO: 15 (EtuN3), the polypeptide sequence of SEQ ID NO: 16 (EtuO), the polypeptide sequence of SEQ ID NO: 17 (EtuP1), the polypeptide sequence of SEQ ID NO: 18 (EtuP2), the polypeptide sequence of SEQ ID NO: 19 (EtuR1), the polypeptide sequence of SEQ ID NO: 20 (EtuR2): the polypeptide sequence of SEQ ID NO: 21 (EtuR3), the polypeptide sequence of SEQ ID NO: 22 (EtuT), the polypeptide sequence of SEQ ID NO: 23 (EtuU1), the polypeptide sequence of SEQ ID NO: 24 (EtuU2), or the polypeptide sequence of SEQ ID NO: 25 (EtuU3)

Also provided is a polypeptide having a sequence that is 90% identical to the polypeptide sequence of SEQ ID NO: 1 (EtuA1), SEQ ID NO: 2 (EtuA2), SEQ ID NO: 3 (EtuA3), SEQ ID NO: 4 (EtuD1), SEQ ID NO: 5 (EtuD2), SEQ ID NO: 6 (EtuD3), SEQ ID NO: 7 (EtuF1), SEQ ID NO: 8 (EtuF2), SEQ ID NO: 9 (EutF3), SEQ ID NO: 10 (EtuH), SEQ ID NO: 11 (EtuM1), SEQ ID NO: 12 (EtuM2), SEQ ID NO: 13 (EtuN1), SEQ ID NO: 14 (EtuN2), SEQ ID NO: 15 (EtuN3), SEQ ID NO: 16 (EtuO), SEQ ID NO: 17 (EtuP1), SEQ ID NO: 18 (EtuP2), SEQ ID NO: 19 (EutR1), SEQ ID NO: 20 (EtuR2): SEQ ID NO: 21 (EtuR3), SEQ ID NO: 22 (EtuT), SEQ ID NO: 23 (EtuU1), SEQ ID NO: 24 (EtuU2), and SEQ ID NO: 25 (EtuU3).

In other embodiments, a polypeptide that is 91%, 92%, 93%, 94%, 95%, 96%, 97%, 98% or 99% identical to a polypeptide sequence of SEQ ID NO: 1 (EtuA1), SEQ ID NO: 2 (EtuA2), SEQ ID NO: 3 (EtuA3), SEQ ID NO: 4 (EtuD1), SEQ ID NO: 5 (EtuD2), SEQ ID NO: 6 (EtuD3), SEQ ID NO: 7 (EtuF1), SEQ ID NO: 8 (EtuF2), SEQ ID NO: 9 (EutF3), SEQ ID NO: 10 (EtuH), SEQ ID NO: 11 (EtuM1), SEQ ID NO: 12 (EtuM2), SEQ ID NO: 13 (EtuN1), SEQ ID NO: 14 (EtuN2), SEQ ID NO: 15 (EtuN3), SEQ ID NO: 16 (EtuO), SEQ ID NO: 17 (EtuP1), SEQ ID NO: 18 (EtuP2), SEQ ID NO: 19 (EutR1), SEQ ID NO: 20 (EtuR2); SEQ ID NO: 21 (EtuR3), SEQ ID NO: 22 (EtuT), SEQ ID NO: 23 (EtuU1), SEQ ID NO: 24 (EtuU2), and SEQ ID NO: 25 (EtuU3) is provided.

Also provided by the present disclosure is a polynucleotide (SEQ ID NO: 57) encoding the polypeptide sequences disclosed herein.

In another embodiment, the present disclosure provides a polynucleotide comprising the sequence of SEQ ID NO: 26 encoding EtuA1, the polynucleotide sequence of SEQ ID NO: 27 encoding EtuA2, the polynucleotide sequence of SEQ ID NO: 28 encoding EtuA3, the polynucleotide sequence of SEQ ID NO: 29 encoding EtuD1, the polynucleotide sequence of SEQ ID NO: 30 encoding EtuD2, the polynucleotide sequence of SEQ ID NO: 31 encoding EtuD3, the polynucleotide sequence of SEQ ID NO: 32 encoding EtuF1, the polynucleotide sequence of SEQ ID NO: 33 encoding EtuF2, the polynucleotide sequence of SEQ ID NO: 34 encoding EtuF3, the polynucleotide sequence of SEQ ID NO: 35 encoding EtuH, the polynucleotide sequence of SEQ ID NO:36 encoding EtuM1, the polynucleotide sequence of SEQ ID NO: 37 encoding EtuM2, the polynucleotide sequence of SEQ ID NO: 38 encoding EtuN1, the polynucleotide sequence of SEQ ID NO: 39 encoding EtuN2, the polynucleotide sequence of SEQ ID NO: 40 encoding EtuN3, the polynucleotide sequence of SEQ ID NO: 41 encoding EtuO, the polynucleotide sequence of SEQ ID NO: 42 encoding EtuP1, the polynucleotide sequence of SEQ ID NO: 43 encoding EtuP2, the polynucleotide sequence of SEQ ID NO: 44 encoding EtuR1, the polynucleotide sequence of SEQ ID NO: 45 encoding EtuR2, the polynucleotide sequence of SEQ ID NO:46 encoding EtuR3, the polynucleotide sequence of SEQ ID NO: 47 encoding EtuT, the polynucleotide sequence of SEQ ID NO: 48 encoding EtuU1, the polynucleotide sequence of SEQ ID NO: 49 encoding EtuU2, and the polynucleotide sequence of SEQ ID NO: 50 encoding EtuU3.

Also provided is a polynucleotide that is 90%, 91%, 92%, 93%, 94%, 95%, 96%, 97%, 98% or 99% identical to the polynucleotide sequence set out in SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, or SEQ ID NO: 50.

In another embodiment, the present disclosure provides an expression vector comprising a polynucleotide comprising the sequence of SEQ ID NO: 26 encoding EtuA1, the polynucleotide sequence of SEQ ID NO: 27 encoding EtuA2, the polynucleotide sequence of SEQ ID NO: 28 encoding EtuA3, the polynucleotide sequence of SEQ ID NO: 29 encoding EtuD1, the polynucleotide sequence of SEQ ID NO: 30 encoding EtuD2, the polynucleotide sequence of SEQ ID NO: 31 encoding EtuD3, the polynucleotide sequence of SEQ ID NO: 32 encoding EtuF1, the polynucleotide sequence of SEQ ID NO: 33 encoding EtuF2, the polynucleotide sequence of SEQ ID NO: 34 encoding EtuF3, the polynucleotide sequence of SEQ ID NO: 35 encoding EtuH, the polynucleotide sequence of SEQ ID NO:36 encoding EtuM1, the polynucleotide sequence of SEQ ID NO: 37 encoding EtuM2, the polynucleotide sequence of SEQ ID NO: 38 encoding EtuN1, the polynucleotide sequence of SEQ ID NO: 39 encoding EtuN2, the polynucleotide sequence of SEQ ID NO: 40 encoding EtuN3, the polynucleotide sequence of SEQ ID NO: 41 encoding EtuO, the polynucleotide sequence of SEQ ID NO: 42 encoding EtuP1, the polynucleotide sequence of SEQ ID NO: 43 encoding EtuP2, the polynucleotide sequence of SEQ ID NO: 44 encoding EtuR1, the polynucleotide sequence of SEQ ID NO: 45 encoding EtuR2, the polynucleotide sequence of SEQ ID NO:46 encoding EtuR3, the polynucleotide sequence of SEQ ID NO: 47 encoding EtuT, the polynucleotide sequence of SEQ ID NO: 48 encoding EtuU1, the polynucleotide sequence of SEQ ID NO: 49 encoding EtuU2, and the polynucleotide sequence of SEQ ID NO: 50 encoding EtuU3.

Also provided is an expression vector comprising a polynucleotide that is 90%, 91%, 92%, 93%, 94%, 95%, 96%, 97%, 98% or 99% identical to the polynucleotide sequence set out in SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, or SEQ ID NO: 50.

The disclosure further provides a polynucleotide comprising one or more of SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO:46, SEQ ID NO: 47, SEQ ID NO: 48, SEQ ID NO: 49, and SEQ ID NO: 50. Also provided is a polynucleotide comprising one or more sequences that is 90%, 91%, 92%, 93%, 94%, 95%, 96%, 97%, 98% or 99% identical to the polynucleotide sequence set out in SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, or SEQ ID NO: 50

The disclosure further provides an expression vector comprising a polynucleotide comprising one or more of SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO:46, SEQ ID NO: 47, SEQ ID NO: 48, SEQ ID NO: 49, and SEQ ID NO: 50. Also provided is an expression vector comprising a polynucleotide comprising one or more sequences that is 90%, 91%, 92%, 93%, 94%, 95%, 96%, 97%, 98% or 99% identical to the polynucleotide sequence set out in SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO:46, SEQ ID NO: 47, SEQ ID NO: 48, SEQ ID NO: 49, or SEQ ID NO: 50

In some embodiments, a transformed host cell is provided, wherein the host cell is transformed with a heterologous polynucleotide comprising the polynucleotide sequence set out in SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO:46, SEQ ID NO: 47, SEQ ID NO: 48, SEQ ID NO: 49, or SEQ ID NO: 50. In another embodiment, a host cell is provided which is transformed with a polynucleotide that is 90%, 91%, 92%, 93%, 94%, 95%, 96%, 97%, 98% or 99% identical to the polynucleotide sequence set out in the polynucleotide sequence set out in SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO:46, SEQ ID NO: 47, SEQ ID NO: 48, SEQ ID NO: 49, or SEQ ID NO: 50. In yet another embodiment, a transformed host cell is provided, wherein the host cell is transformed with one or more heterologous polynucleotides comprising the polynucleotide sequence set out in SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO:46, SEQ ID NO: 47, SEQ ID NO: 48, SEQ ID NO: 49, and SEQ ID NO: 50. In still another embodiment, a transformed host cell is provided comprising a polynucleotide that is 90%, 91%, 92%, 93%, 94%, 95%, 96%, 97%, 98% or 99% identical to one or more polynucleotide sequences set out in the polynucleotide sequences set out in SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO:46, SEQ ID NO: 47, SEQ ID NO: 48, SEQ ID NO: 49, and SEQ ID NO: 50.

Also provided is a host cell transformed with a polynucleotide encoding (i) EtuA1 (SEQ ID NO: 1) or a protein 90%, 91%, 92%, 93, 94%, 95%, 96%, 97%, 98% or 99% identical to SEQ ID NO: 1 having EtuA1 activity, and (ii) EtuA2 (SEQ ID NO:2) or a protein 90%, 91%, 92%, 93, 94%, 95%, 96%, 97%, 98% or 99% identical to SEQ ID NO: 2 having EtuA2 activity. In various embodiments, the host cell is further transformed with a polynucleotide encoding EtuF3 (SEQ ID NO: 3) or a protein 90%, 91%, 92%, 93, 94%, 95%, 96%, 97%, 98% or 99% identical to SEQ ID NO: 3 having EtuF3 activity. In still further embodiments, the host cell of is further transformed with a polynucleotide encoding EtuO (SEQ ID NO: 16) or a protein 90%, 91%, 92%, 93, 94%, 95%, 96%, 97%, 98% or 99% identical to SEQ ID NO: 16 having EtuO activity. In still other embodiments, the host cell is further transformed with a polynucleotide encoding EtuA3 (SEQ ID NO: 3) or a protein 90%, 91%, 92%, 93, 94%, 95%, 96%, 97%, 98% or 99% identical to SEQ ID NO: 3 having EtuA3 activity. In other embodiments, host cell is further transformed with a polynucleotide encoding (i) EtuH (SEQ ID NO: 10) or a protein 90%, 91%, 92%, 93, 94%, 95%, 96%, 97%, 98% or 99% identical to SEQ ID NO: 10 having EtuH activity (ii) EtuM2 (SEQ ID NO: 12) or a protein 90%, 91%, 92%, 93, 94%, 95%, 96%, 97%, 98% or 99% identical to SEQ ID NO: 12 having EtuM2 activity (iii) EtuM1 (SEQ ID NO:11) or a protein 90%, 91%, 92%, 93, 94%, 95%, 96%, 97%, 98% or 99% identical to SEQ ID NO: 11 having EtuM1 activity.

Also provided is a host cell transformed with a polynucleotide encoding (i) EtuA1 (SEQ ID NO: 1) or a protein 90%, 91%, 92%, 93, 94%, 95%, 96%, 97%, 98% or 99% identical to SEQ ID NO: 1 having EtuA1 activity, and (ii) EtuA2 (SEQ ID NO:2) or a protein 90%, 91%, 92%, 93, 94%, 95%, 96%, 97%, 98% or 99% identical to SEQ ID NO: 2 having EtuA2 activity, the host cell further transformed with a polynucleotide encoding EtuA3 (SEQ ID NO: 3) or a protein 90%, 91%, 92%, 93, 94%, 95%, 96%, 97%, 98% or 99% identical to SEQ ID NO: 3 having EtuA3 activity. In various embodiments, the host cell is further transformed with a polynucleotide encoding EtuF3 (SEQ ID NO: 9) or a protein 90%, 91%, 92%, 93, 94%, 95%, 96%, 97%, 98% or 99% identical to SEQ ID NO: 9 having EtuF3 activity. In still other embodiments, the host cell is further transformed with a polynucleotide encoding EtuO (SEQ ID NO: 16) or a protein 90%, 91%, 92%, 93, 94%, 95%, 96%, 97%, 98% or 99% identical to SEQ ID NO: 16 having EtuO activity. In still other embodiments, the host cell is further transformed with a polynucleotide encoding EtuH (SEQ ID NO: 10) or a protein 90%, 91%, 92%, 93, 94%, 95%, 96%, 97%, 98% or 99% identical to SEQ ID NO: 10 having EtuH activity (ii) EtuM2 (SEQ ID NO: 12) or a protein 90%, 91%, 92%, 93, 94%, 95%, 96%, 97%, 98% or 99% identical to SEQ ID NO: 12 having EtuM2 activity (iii) EtuM1 (SEQ ID NO: 11) or a protein 90%, 91%, 92%, 93, 94%, 95%, 96%, 97%, 98% or 99% identical to SEQ ID NO: 11 having EtuM1 activity.

Also provided is a host cell transformed with a polynucleotide encoding EtuO (SEQ ID NO: 16) or a protein 90%, 91%, 92%, 93, 94%, 95%, 96%, 97%, 98% or 99% identical to SEQ ID NO: 16 having EtuO activity. In various embodiments, the host cell is further transformed with a polynucleotide encoding (i) EtuF3 (SEQ ID NO: 9) or a protein 90%, 91%, 92%, 93, 94%, 95%, 96%, 97%, 98% or 99% identical to SEQ ID NO: 9 having EtuF3 activity (ii) EtuA1 (SEQ ID NO: 1) or a protein 90%, 91%, 92%, 93, 94%, 95%, 96%, 97%, 98% or 99% identical to SEQ ID NO: 1 having EtuA1 activity (iii) EtuA2 (SEQ ID NO: 2) or a protein 90%, 91%, 92%, 93, 94%, 95%, 96%, 97%, 98% or 99% identical to SEQ ID NO: 2, having EtuA2 activity. In other aspects, the host cell is further transformed with a polynucleotide encoding EtuA3 (SEQ ID NO: 3) or a protein 90%, 91%, 92%, 93, 94%, 95%, 96%, 97%, 98% or 99% identical to SEQ ID NO: 3 having EtuA3 activity. In still other aspects, the host cell is further transformed with a polynucleotide encoding EtuH (SEQ ID NO: 10) or a protein 90%, 91%, 92%, 93, 94%, 95%, 96%, 97%, 98% or 99% identical to SEQ ID NO: 10 having EtuH activity (ii) EtuM2 (SEQ ID NO: 12) or a protein 90%, 91%, 92%, 93, 94%, 95%, 96%, 97%, 98% or 99% identical to SEQ ID NO: 12 having EtuM2 activity (iii) EtuM1 (SEQ ID NO: 11) or a protein 90%, 91%, 92%, 93, 94%, 95%, 96%, 97%, 98% or 99% identical to SEQ ID NO: 11 having EtuM1 activity.

The present disclosure additionally provides a method for synthesizing a nonribosomal peptide synthetase (NRPS) derived drug, an analog of an NRPS derived drug, or a metabolic intermediate in the NRPS derived drug synthetic pathway in a host cell comprising the step of culturing a host cell of the present disclosure under conditions suitable to produce the nonribosomal peptide synthetase (NRPS) derived drug and/or analog. In some aspects, the NRPS derived drug is ET743.

In various embodiments, the host cell is a prokaryote. In some aspects, the prokaryote is selected from the group consisting of *E. coli, Streptomyces lavendulae, Myxococcus xanthus*, and *Pseudomonas fluorescens*.

In some embodiments, the host cell comprises one or more heterologous polynucleotides encoded on an expression vector. In some aspects, the one or more heterologous polynucleotides are present in a single expression vector. In further aspects, the expression vector comprises a sequence that encodes the polypeptide sequence as set forth in SEQ ID NO: 4.

In some embodiments, the at least two heterologous polynucleotides are encoded on separate expression vectors. In some aspects, the at least two of the heterologous polynucleotides are encoded on a single expression vector.

DETAILED DESCRIPTION OF THE INVENTION

Figure 1:
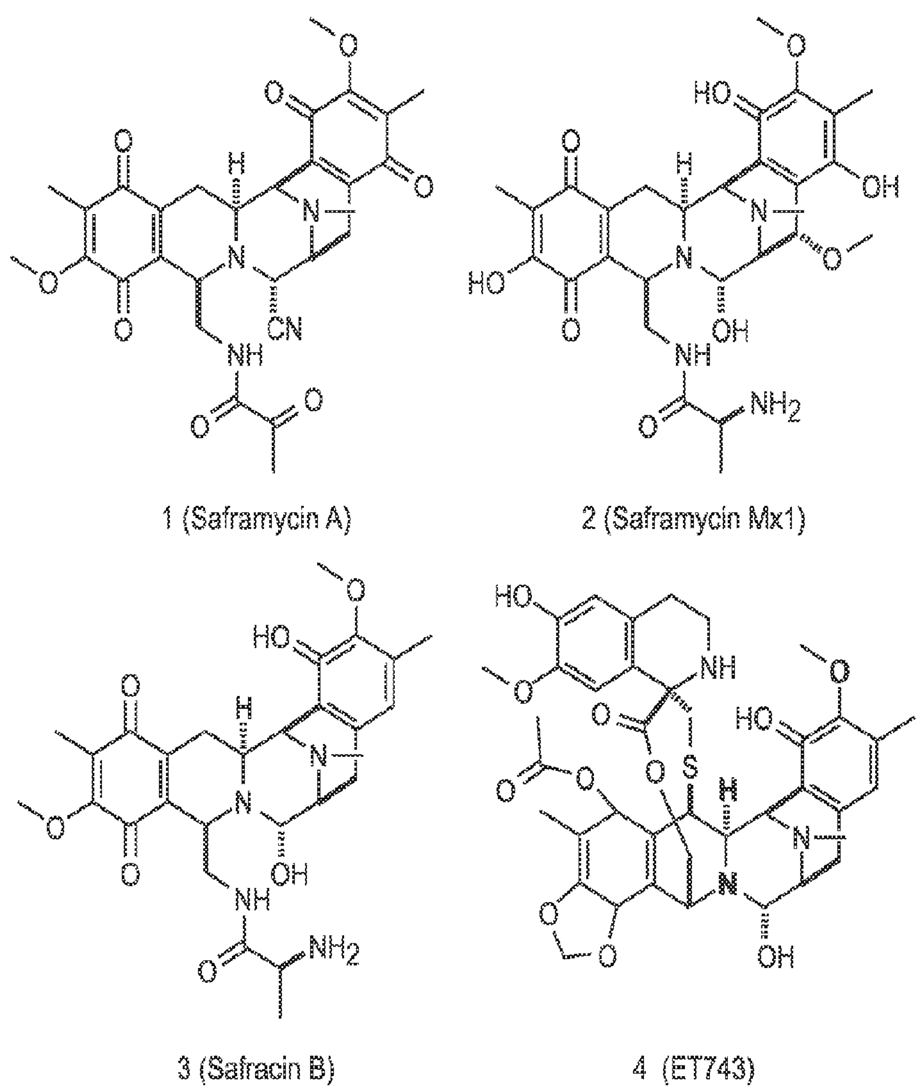
FIG. 1 depicts four tetrahydroquinoline antibiotics. 1. Saframycin A (*Streptomyces lavendulae*), 2. Saframycin Mx1 (*Myxococcus xanthus*), 3. Safracin (*Pseudomonas fluorescens*), 4. ET743.
Figure 2:
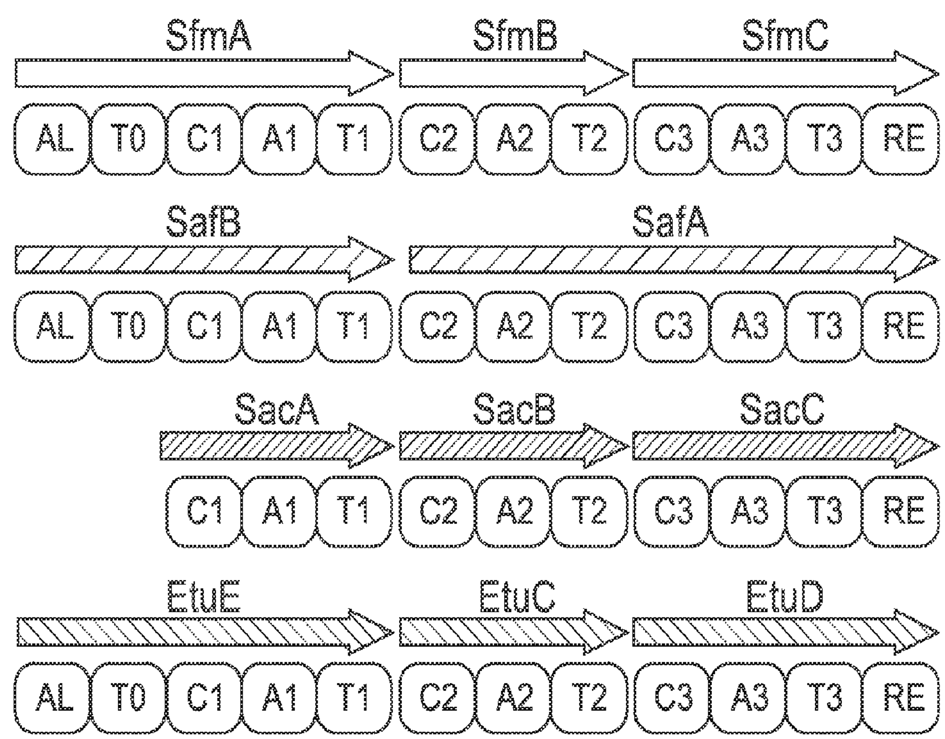
FIG. 2 depicts the three known and one hypothesized biosynthetic pathway for Saframycin A (Sfm), Saframycin Mx1 (Saf), Safracin (Sac), and ET743 (Etu).

Disclosed herein is a biosynthetic pathway for production of a NRPS derived drug, ET743. Knowledge of this pathway enables economical access to the drug and analogs through heterologous expression [Tang et al., *Science* 287: 640-642 (2000); Wenzel et al., *Current Opinion in Biotechnology* 16: 594 (2005)] and pathway engineering [Nguyen et al., *Proceedings of the National Academy of Sciences of the United States of America* 103: 17462 (2006)]. The disclosure of the polynucleotide and polypeptide sequences herein began with collection of the tunicate *E. turbinata*. Presence of ET743 in the sample collected was verified by mass spectrometry as a surrogate for the presence of the presumed symbiont. Two rounds of metagenomic Roche 454 FLX™ Platinum sequencing were performed and after multiple rounds of gap filling by PCR and Sanger sequencing, assembly and annotation, a putative gene cluster for ET743 biosynthesis was identified. Key proteins in the proposed biosynthetic pathway were heterologously expressed and activity was determined in vitro with mass spectrometry and radioassays, confirming key steps at the initiation, cyclization, and termination of ET743 biosynthesis. This work has broad implications for accessing other unknown natural products from complex assemblages. In one embodiment, the present disclosure provides a method for directly accessing this potent drug through fermentation.

Accordingly, the present disclosure provides a polynucleotide sequence encoding the one or more polypeptides in the pathway for production of Etu disclosed herein. Those polypeptides include the polypeptide sequence of SEQ ID NO: 1 (EtuA1), the polypeptide sequence of SEQ ID NO: 2 (EtuA2), the polypeptide sequence of SEQ ID NO: 3 (EtuA3), the polypeptide sequence of SEQ ID NO: 4 (EtuD1), the polypeptide sequence of SEQ ID NO: 5 (EtuD2), the polypeptide sequence of SEQ ID NO: 6 (EtuD3), the polypeptide sequence of SEQ ID NO: 7 (EtuF1), the polypeptide sequence of SEQ ID NO: 8 (EtuF2), the polypeptide sequence of SEQ ID NO: 9 (EutF3), the polypeptide sequence of SEQ ID NO: 10 (EtuH), the polypeptide sequence of SEQ ID NO: 11 (EtuM1), the polypeptide sequence of SEQ ID NO: 12 (EtuM2), the polypeptide sequence of SEQ ID NO: 13 (EtuN1), the polypeptide sequence of SEQ ID NO: 14 (EtuN2), the polypeptide sequence of SEQ ID NO: 15 (EtuN3), the polypeptide sequence of SEQ ID NO: 16 (EtuO), the polypeptide sequence of SEQ ID NO: 17 (EtuP1), the polypeptide sequence of SEQ ID NO: 18 (EtuP2), the polypeptide sequence of SEQ ID NO: 19 (EutR1), the polypeptide sequence of SEQ ID NO: 20 (EtuR2): the polypeptide sequence of SEQ ID NO: 21 (EtuR3), the polypeptide sequence of SEQ ID NO: 22 (EtuT), the polypeptide sequence of SEQ ID NO: 23 (EtuU1), the polypeptide sequence of SEQ ID NO: 24 (EtuU2), or the polypeptide sequence of SEQ ID NO: 25 (EtuU3). Polypeptides contemplated also include those comprising an polypeptide that is 90%, 91%, 92%, 93%, 94%, A polynucleotide sequence is also provided that encodes the polypeptide sequence of SEQ ID NO: 1 (EtuA1), the polypeptide sequence of SEQ ID NO: 2 (EtuA2), the polypeptide sequence of SEQ ID NO: 3 (EtuA3), the polypeptide sequence of SEQ ID NO: 4 (EtuD1), the polypeptide sequence of SEQ ID NO: 5 (EtuD2), the polypeptide sequence of SEQ ID NO: 6 (EtuD3), the polypeptide sequence of SEQ ID NO: 7 (EtuF1), the polypeptide sequence of SEQ ID NO: 8 (EtuF2), the polypeptide sequence of SEQ ID NO: 9 (EutF3), the polypeptide sequence of SEQ ID NO: 10 (EtuH), the polypeptide sequence of SEQ ID NO: 11 (EtuM1), the polypeptide sequence of SEQ ID NO: 12 (EtuM2), the polypeptide sequence of SEQ ID NO: 13 (EtuN1), the polypeptide sequence of SEQ ID NO: 14 (EtuN2), the polypeptide sequence of SEQ ID NO: 15 (EtuN3), the polypeptide sequence of SEQ ID NO: 16 (EtuO), the polypeptide sequence of SEQ ID NO: 17 (EtuP1), the polypeptide sequence of SEQ ID NO: 18 (EtuP2), the polypeptide sequence of SEQ ID NO: 19 (EutR1), the polypeptide sequence of SEQ ID NO: 20 (EtuR2): the polypeptide sequence of SEQ ID NO: 21 (EtuR3), the polypeptide sequence of SEQ ID NO: 22 (EtuT), the polypeptide sequence of SEQ ID NO: 23 (EtuU1), the polypeptide sequence of SEQ ID NO: 24 (EtuU2), or the polypeptide sequence of SEQ ID NO: 25 (EtuU3).

A polynucleotide sequence is also provided that encodes a polypeptide that is 90%, 91%, 92%, 93%, 94%, 95%, 96%, 97%, 98%, or 99% identical to the polypeptide sequence of SEQ ID NO: 1 (EtuA1), the polypeptide sequence of SEQ ID NO: 2 (EtuA2), the polypeptide sequence of SEQ ID NO: 3 (EtuA3), the polypeptide sequence of SEQ ID NO: 4 (EtuD1), the polypeptide sequence of SEQ ID NO: 5 (EtuD2), the polypeptide sequence of SEQ ID NO: 6 (EtuD3), the polypeptide sequence of SEQ ID NO: 7 (EtuF1), the polypeptide sequence of SEQ ID NO: 8 (EtuF2), the polypeptide sequence of SEQ ID NO: 9 (EutF3), the polypeptide sequence of SEQ ID NO: 10 (EtuH), the polypeptide sequence of SEQ ID NO: 11 (EtuM1), the polypeptide sequence of SEQ ID NO: 12 (EtuM2), the polypeptide sequence of SEQ ID NO: 13 (EtuN1), the polypeptide sequence of SEQ ID NO: 14 (EtuN2), the polypeptide sequence of SEQ ID NO: 15 (EtuN3), the polypeptide sequence of SEQ ID NO: 16 (EtuO), the polypeptide sequence of SEQ ID NO: 17 (EtuP1), the polypeptide sequence of SEQ ID NO: 18 (EtuP2), the polypeptide sequence of SEQ ID NO: 19 (EutR1), the polypeptide sequence of SEQ ID NO: 20 (EtuR2): the polypeptide sequence of SEQ ID NO: 21 (EtuR3), the polypeptide sequence of SEQ ID NO: 22 (EtuT), the polypeptide sequence of SEQ ID NO: 23 (EtuU1), the polypeptide sequence of SEQ ID NO: 24 (EtuU2), or the polypeptide sequence of SEQ ID NO: 25 (EtuU3).

Exemplary polynucleotides encoding polypeptides of the disclosure are set out in Table 1.

TABLE 1

| Etu Gene | Polypeptide Sequence ID Number | Polynucleotide Sequence ID Number |
|---|---|---|
| A1 | 1 | 26 |
| A2 | 2 | 27 |
| A3 | 3 | 28 |
| D1 | 4 | 29 |
| D2 | 5 | 30 |
| D3 | 6 | 31 |
| F1 | 7 | 32 |
| F2 | 8 | 33 |
| F3 | 9 | 34 |
| H | 10 | 35 |
| M1 | 11 | 36 |
| M2 | 12 | 37 |
| N1 | 13 | 38 |
| N2 | 14 | 39 |
| N3 | 15 | 40 |
| O | 16 | 41 |
| P1 | 17 | 42 |
| P2 | 18 | 43 |
| Rl | 19 | 44 |
| R2 | 20 | 45 |
| R3 | 21 | 46 |
| T | 22 | 47 |
| U1 | 23 | 48 |
| U2 | 24 | 49 |
| U3 | 25 | 50 |

Accordingly, the disclosure provides a polynucleotide comprising the sequence of SEQ ID NO: 26 encoding EtuA1, the polynucleotide sequence of SEQ ID NO: 27 encoding EtuA2, the polynucleotide sequence of SEQ ID NO: 28 encoding EtuA3, the polynucleotide sequence of SEQ ID NO: 29 encoding EtuD1, the polynucleotide sequence of SEQ ID NO: 30 encoding EtuD2, the polynucleotide sequence of SEQ ID NO: 31 encoding EtuD3, the polynucleotide sequence of SEQ ID NO: 32 encoding EtuF1, the polynucleotide sequence of SEQ ID NO: 33 encoding EtuF2, the polynucleotide sequence of SEQ ID NO: 34 encoding EtuF3, the polynucleotide sequence of SEQ ID NO: 35 encoding EtuH, the polynucleotide sequence of SEQ ID NO:36 encoding EtuM1, the polynucleotide sequence of SEQ ID NO: 37 encoding EtuM2, the polynucleotide sequence of SEQ ID NO: 38 encoding EtuN1, the polynucleotide sequence of SEQ ID NO: 39 encoding EtuN2, the polynucleotide sequence of SEQ ID NO: 40 encoding EtuN3, the polynucleotide sequence of SEQ ID NO: 41 encoding EtuO, the polynucleotide sequence of SEQ ID NO: 42 encoding EtuP1, the polynucleotide sequence of SEQ ID NO: 43 encoding EtuP2, the polynucleotide sequence of SEQ ID NO: 44 encoding EtuR1, the polynucleotide sequence of SEQ ID NO: 45 encoding EtuR2, the polynucleotide sequence of SEQ ID NO:46 encoding EtuR3, the polynucleotide sequence of SEQ ID NO: 47 encoding EtuT, the polynucleotide sequence of SEQ ID NO: 48 encoding EtuU1, the polynucleotide sequence of SEQ ID NO: 49 encoding EtuU2, and the polynucleotide sequence of SEQ ID NO: 50 encoding EtuU3.

Also provided is a polynucleotide that is 90%, 91%, 92%, 93%, 94%, 95%, 96%, 97%, 98% or 99% identical to the polynucleotide sequence set out in SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO:46, SEQ ID NO: 47, SEQ ID NO: 48, SEQ ID NO: 49, or SEQ ID NO: 50.

Also provided by the present disclosure is a host cell transformed with a heterologous polynucleotide comprising any one or more of the polynucleotide sequences comprising the sequence of SEQ ID NO: 26 encoding EtuA1, the polynucleotide sequence of SEQ ID NO: 27 encoding EtuA2, the polynucleotide sequence of SEQ ID NO: 28 encoding EtuA3, the polynucleotide sequence of SEQ ID NO: 29 encoding EtuD1, the polynucleotide sequence of SEQ ID NO: 30 encoding EtuD2, the polynucleotide sequence of SEQ ID NO: 31 encoding EtuD3, the polynucleotide sequence of SEQ ID NO: 32 encoding EtuF1, the polynucleotide sequence of SEQ ID NO: 33 encoding EtuF2, the polynucleotide sequence of SEQ ID NO: 34 encoding EtuF3, the polynucleotide sequence of SEQ ID NO: 35 encoding EtuH, the polynucleotide sequence of SEQ ID NO:36 encoding EtuM1, the polynucleotide sequence of SEQ ID NO: 37 encoding EtuM2, the polynucleotide sequence of SEQ ID NO: 38 encoding EtuN1, the polynucleotide sequence of SEQ ID NO: 39 encoding EtuN2, the polynucleotide sequence of SEQ ID NO: 40 encoding EtuN3, the polynucleotide sequence of SEQ ID NO: 41 encoding EtuO, the polynucleotide sequence of SEQ ID NO: 42 encoding EtuP1, the polynucleotide sequence of SEQ ID NO: 43 encoding EtuP2, the polynucleotide sequence of SEQ ID NO: 44 encoding EtuR1, the polynucleotide sequence of SEQ ID NO: 45 encoding EtuR2, the polynucleotide sequence of SEQ ID NO:46 encoding EtuR3, the polynucleotide sequence of SEQ ID NO: 47 encoding EtuT, the polynucleotide sequence of SEQ ID NO: 48 encoding EtuU1, the polynucleotide sequence of SEQ ID NO: 49 encoding EtuU2, and the polynucleotide sequence of SEQ ID NO: 50 encoding EtuU3. Host cells are also provided comprising one or more polynucleotides that is/are 90%, 91%, 92%, 93%, 94%, 95%, 96%, 97%, 98% or 99% identical to one or more polynucleotide sequences set out in the polynucleotide sequences set out in SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO:46, SEQ ID NO: 47, SEQ ID NO: 48, SEQ ID NO: 49, and SEQ ID NO: 50. Additionally, host cells are provided comprising a polynucleotide encoding one or more polypeptides selected from the group consisting of the polypeptide sequence of SEQ ID NO: 1 (EtuA1), the polypeptide sequence of SEQ ID NO: 2 (EtuA2), the polypeptide sequence of SEQ ID NO: 3 (EtuA3), the polypeptide sequence of SEQ ID NO: 4 (EtuD1), the polypeptide sequence of SEQ ID NO: 5 (EtuD2), the polypeptide sequence of SEQ ID NO: 6 (EtuD3), the polypeptide sequence of SEQ ID NO: 7 (EtuF1), the polypeptide sequence of SEQ ID NO: 8 (EtuF2), the polypeptide sequence of SEQ ID NO: 9 (EutF3), the polypeptide sequence of SEQ ID NO: 10 (EtuH), the polypeptide sequence of SEQ ID NO: 11 (EtuM1), the polypeptide sequence of SEQ ID NO: 12 (EtuM2), the polypeptide sequence of SEQ ID NO: 13 (EtuN1), the polypeptide sequence of SEQ ID NO: 14 (EtuN2), the polypeptide sequence of SEQ ID NO: 15 (EtuN3), the polypeptide sequence of SEQ ID NO: 16 (EtuO), the polypeptide sequence of SEQ ID NO: 17 (EtuP1), the polypeptide sequence of SEQ ID NO: 18 (EtuP2), the polypeptide sequence of SEQ ID NO: 19 (EutR1), the polypeptide sequence of SEQ ID NO: 20 (EtuR2): the polypeptide sequence of SEQ ID NO: 21 (EtuR3), the polypeptide sequence of SEQ ID NO: 22 (EtuT), the polypeptide sequence of SEQ ID NO: 23 (EtuU1), the polypeptide sequence of SEQ ID NO: 24 (EtuU2), or the polypeptide sequence of SEQ ID NO: 25 (EtuU3) In still other aspects, a host cell is provided comprising a polynucleotide encoding one or more polypeptides that is 90%, 91%, 92%, 93%, 94%, 95%, 96%, 97%, 98%, or 99% identical to the polypeptide sequence of SEQ ID NO: 1 (EtuA1), the polypeptide sequence of SEQ ID NO: 2 (EtuA2), the polypeptide sequence of SEQ ID NO: 3 (EtuA3), the polypeptide sequence of SEQ ID NO: 4 (EtuD1), the polypeptide sequence of SEQ ID NO: 5 (EtuD2), the polypeptide sequence of SEQ ID NO: 6 (EtuD3), the polypeptide sequence of SEQ ID NO: 7 (EtuF1), the polypeptide sequence of SEQ ID NO: 8 (EtuF2), the polypeptide sequence of SEQ ID NO: 9 (EutF3), the polypeptide sequence of SEQ ID NO: 10 (EtuH), the polypeptide sequence of SEQ ID NO: 11 (EtuM1), the polypeptide sequence of SEQ ID NO: 12 (EtuM2), the polypeptide sequence of SEQ ID NO: 13 (EtuN1), the polypeptide sequence of SEQ ID NO: 14 (EtuN2), the polypeptide sequence of SEQ ID NO: 15 (EtuN3), the polypeptide sequence of SEQ ID NO: 16 (EtuO), the polypeptide sequence of SEQ ID NO: 17 (EtuP1), the polypeptide sequence of SEQ ID NO: 18 (EtuP2), the polypeptide sequence of SEQ ID NO: 19 (EutR1), the polypeptide sequence of SEQ ID NO: 20 (EtuR2): the polypeptide sequence of SEQ ID NO: 21 (EtuR3), the polypeptide sequence of SEQ ID NO: 22 (EtuT), the polypeptide sequence of SEQ ID NO: 23 (EtuU1), the polypeptide sequence of SEQ ID NO: 24 (EtuU2), and or the polypeptide sequence of SEQ ID NO: 25 (EtuU3).

It will be understood by those of skill in the art that a host cell can be transformed with 1, 2, 3, 4, 5, 6, 7, 8, 9 or all of the polynucleotides identified in Table 1. In various aspects, a transformed host cell comprises one, two, three or more expression vectors. Suitable host cells are known to those of ordinary skill in the art, and include without limitation prokaryotic host cells.

"Heterologous," as used herein, means of different natural origin or of synthetic origin. For example and without limitation, if a host cell is transformed with a polynucleotide sequence that does not occur in the untransformed host cell, that nucleic acid sequence is said to be heterologous with respect to the host cell. The transforming nucleic acid optionally includes, in various embodiments, a heterologous promoter, heterologous coding sequence, and/or heterologous termination sequence. Alternatively, the transforming polynucleotide in another embodiment, is completely heterologous or includes any possible combination of heterologous and endogenous polynucleotide sequences. Similarly, "heterologous" refers to a polynucleotide sequence derived from and inserted into the same natural, original cell type, but which is present in a non-natural state, e.g., a different copy number, or under the control of different regulatory elements. The term "heterologous" applies to cells, including plant and bacterial cells, and also to plasmids, plastids, and viruses.

As used herein, "analog" means that a described compound shares a structural or functional characteristic with a parent compound from which it was derived or designed.

Figure 3A:
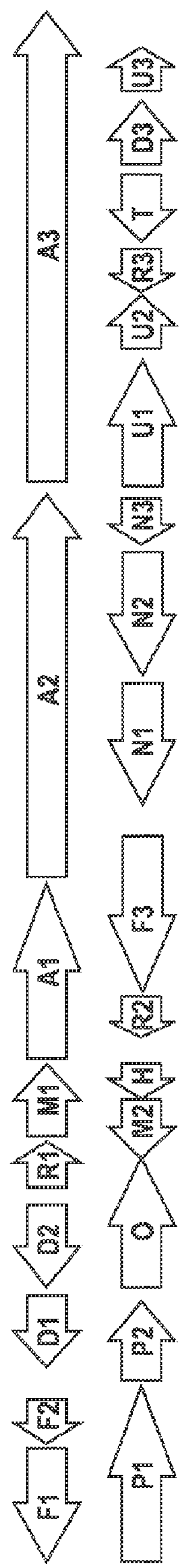
FIG. 3 depicts the ET-743 biosynthetic gene cluster (a). Gene names relate to proposed function for each protein: EtuA-NRPS, EtuD-DNA processing, EtuF-fatty-acid enzymes, EtuH-hydroxylase, EtuM-methyltransferases, EtuN-amidotransferases, EtuO-monoxygenase, EtuP-pyruvate cassette, EtuR-regulatory enzymes, EtuT-drug transporter, EtuU-unknown function. Proposed biosynthetic pathway for ET-743. (b) Named intermediates (characterized), enzymes (if assigned) and enzyme intermediates (thioester-bound) are shown.
Figure 3B:
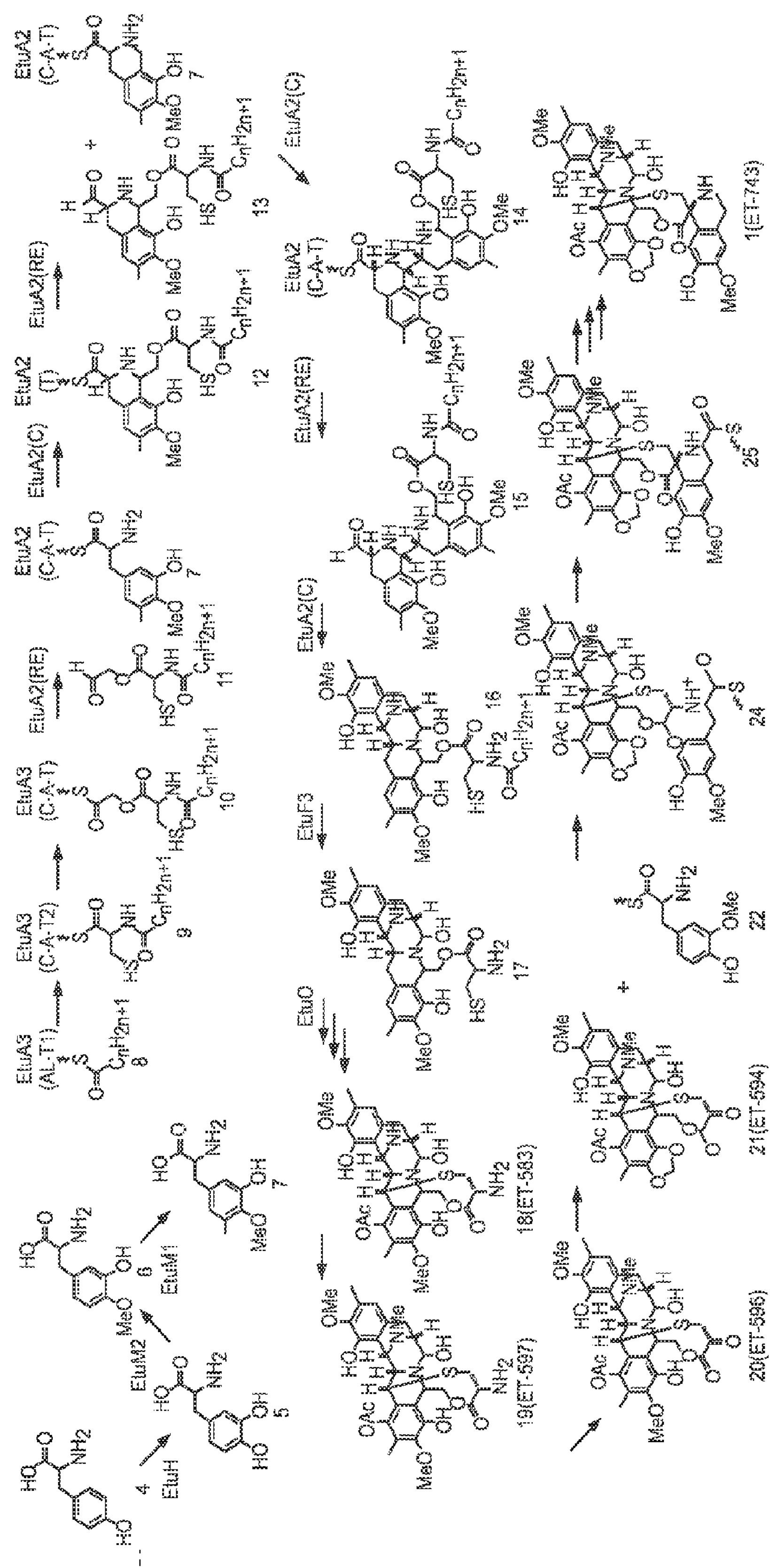

It is understood that the term "intermediate" as used means that a compound may be subjected to further processing steps, for example and without limitation as disclosed herein for the synthesis of ET743. The term "intermediate" is used interchangeably with the term "metabolic intermediate" herein. FIG. 3 sets out a pathway for production of ET743 with various intermediates in the synthetic pathway. Intermediates are contemplated without limitation for their immediate use, for isolation and storage for use at a later time, for use in the production of analogs, and as semi-synthetic precursors of the NRPS not limited to ET743. In some embodiments, inter mediates are contemplated for the production of semi-synthetic compounds that have antimicrobial, anticancer, and/or anti-inflammatory activity. The person of skill in the art will appreciate that intermediates as described herein are also useful in themselves, or useful for production of, for example, ET743 by their modification in an in vitro systems incorporating one or more isolated polypeptides as described herein and in FIG. 3 that allow for production of ET743. Alternatively, intermediates are used to in vivo systems wherein a transformed host cell as described here is capable of taking up the intermediate and further processing the intermediate to provide ET743.

In an embodiment, the present disclosure provides a method for synthesizing a nonribosomal peptide synthetase (NRPS) derived drug and/or analog and/or intermediate in a host cell comprising the step of culturing the host cell as described herein under conditions suitable to produce the nonribosomal peptide synthetase (NRPS) derived drug and/or analog. Illustrative host cells include prokaryotic, yeast, avian, fungal, insect, mammalian, and plant cells. Prokaryotic host cells contemplated herein include without limitation *E. coli, Streptomyces lavendulae, Myxococcus xanthus*, and *Pseudomonas fluorescens. E. coli* host cells contemplated herein include without limitation laboratory and/or industrial strains of *E. coli* cells, such as BL21 or K12-derived strains (e.g., C600, DH1α, DH5α, HB101, INV1, JM109, TB1, TG1, and X-1Blue). Such strains are available from the ATCC or from commercial vendors such as BD Biosciences Clontech (Palo Alto, Calif.) and Stratagene (La Jolla, Calif.). For detailed descriptions of nucleic acid manipulation techniques, see Ausubel et al., eds., Current Protocols in Molecular Biology, Wiley Interscience, 2006, and Sambrook and Russell, Molecular Cloning: A Laboratory Manual, Cold Spring Harbor Press, NY, 2001, each of which is incorporated herein by reference in its entirety.

As used herein, "expression vector" refers to a polynucleotide sequence capable of directing expression of a particular polynucleotide sequence in an appropriate host cell, including a promoter operably linked to the polynucleotide sequence of interest, which is optionally operably linked to 3' sequences, such as 3' regulatory sequences or termination signals. In some aspects, an expression vector also includes sequences required for proper translation of the polynucleotide sequence if any such sequences are needed.

Methods are also provided wherein a host cell transformed with one or more expression vectors, encoding one or more polypeptides of the present disclosure, produces an intermediate compound in the synthesis of a NRPS drug. In some aspects of the method, the intermediate is isolated. In various other aspects of the method, the intermediate is used to complete synthesis of the NRPS drug. The synthesis method is, in various aspects, completed in the same host cell. In other aspects, the synthesis method is completed in a different host cell. In further aspects, methods are provided wherein the different host cell is transformed with one or more expression vectors encoding one or more polypeptides that are useful for the completion of said synthesis. The one or more polypeptides are, in some aspects, any of the polypeptides described herein, and in some aspects are heterologous polypeptides that catalyze the same or similar steps in the biosynthetic pathway. It will be understood by those of ordinary skill in the art that polypeptides from genetically related or unrelated organisms may have the same or similar enzymatic capabilities as those disclosed herein. Accordingly, it is contemplated that such polypeptides may be used in combination with the polypeptides described herein in the synthesis of a NRPS drug and/or analog and/or intermediate.

In some embodiments, at least two heterologous polynucleotides are encoded on separate expression vectors. In some embodiments, at least two of the heterologous polynucleotides are encoded on a single expression vector.

It is noted here that, as used in this specification and the appended claims, the singular forms "a," "an," and "the" include plural reference unless the context clearly dictates otherwise.

Enzymes in Et743 Synthesis

EtuA1, EtuA2, EtuA3 are Three Predicted NRPSs with Catalytic Domains Bearing Predicted Amino Acid Specificity Motifs.

Sequence analysis and deep annotation revealed that biosynthetic pathway architecture is non-collinear (as with SafA-B) and is represented by EtuA3→EtuA1→EtuA2 EtuA3 (AL-T-C-A-T) contains the AL-T starter module that is common to the saframycin, and saframycin Mx1 metabolic systems. The role of this module was elucidated for the saframycin biosynthetic pathway, where acylation of the precursor is required for further chain extension, cyclization and RE processing (Pictet-Spenglerase). The NRPS A-domain, based upon the amino acid specificity motif, was predicted to utilize cysteine with 100% sequence identity to the top three cysteine A domain sequence motifs. EtuA3 specificity is, therefore, unique to the Etu biosynthetic pathway and a key differentiator compared to other characterized tetrahydroisoquinoline systems, which all utilize alanine. EtuA1 (C-A-T) has the greatest homology to SafA module 1 by BLASTx; however, the protein sequence identity and similarity are relatively low (29/54) compared to the other NRPSs in the pathway. An A-domain selectivity motif cannot be identified in EtuA1. Based on structural analysis of ET-743, a glycolic acid unit may be loaded and activated by the EtuA1 A-domain. Loading of hydroxy acids and formation of esters by NRPS modules have been characterized previously. This extender unit represents another key difference relative to characterized tetrahydroisoquinoline antibiotics, for which a conserved core motif (7/8 amino acid identity) is both predicted and observed to select glycine. EtuA2 (C-A-T-RE) contains the same A-domain specificity motif for the final NRPS module as all known tetrahydroisoquinoline biosynthetic pathways. As verified in the saframycin biosynthetic system, the EtuA2 homolog SfmC iteratively extends two 3H-4O-Me-5Me-Tyr residues. The terminal EtuR2 RE domain serves as a key marker of the pathway and was examined biochemically to assess its activity in elaborating the tetrahydroisoquinoline core molecule DNA Processing Enzymes are Unusual to Observe in a Natural Product Biosynthetic Pathway.

It is hypothesized EtuD1-3 may have a role in repairing damage induced by ET-743 given its mechanism of action. EtuD1 appears to be a homolog of the TatD Mg2+ dependent DNAse while EtuD2 shows similarity to a DNA polymerase III subunit δ', which has been characterized as part of the DNA-enzyme assembly complex. EtuD3 is a homolog of the 5'→3' exonuclease domain from DNA polymerase I.

Fatty Acid Processing Enzymes.

Pathway components that mediate production of essential cofactors or substrates are often encoded within biosynthetic gene clusters21. EtuF1 and EtuF2 appear to represent subunits of an acetyl-CoA carboxylase. These enzymes transform acetyl-CoA to malonyl-CoA for fatty acid biosynthesis, and may supply substrate for synthesis of the fatty acid for EtuA3 AL. EtuF3 appears to be a penicillin acylase40. It is proposed that this key enzyme may act to release the predicted fatty acid modified intermediate of ET-743 after formation of the tetradepsipeptide and Pictet-Spengler cyclization (FIG. 4) prior to further processing into mature intermediates that are isolable from the tunicate.

Generation of 3-hydroxy-4-O-methyl-5-methyl-tyrosine (Hydroxylase and Methyltransferases).

ET-743 is derived from at least two units of the unusual amino acid 3H-40-Me-5Me-Tyr. The intermediate may be generated through 3-hydroxylation, 4-O-methylation, and 5-methylation of tyrosine. EtuH, an SfmD homolog, is predicted to hydroxylate tyrosine at the 3-position, whereas EtuM1, a SacF homolog, may be a SAM-dependent methyltransferase and a candidate for C-methylation at the 5-position. SafC, an EtuM2 homolog, has been characterized in vitro as a catechol 4-O-methyltransferase41. Biochemical studies in the saframycin pathway revealed that SfmD (EtuH homolog), SfmM2 (EtuM1 homolog) and SmfM3 (EtuM2 homolog) form a minimal unit for 3H-4O-Me-5Me-Tyr production thus diverting tyrosine to secondary metabolism.

EtuO is an FAD-Dependent Monooxygenase that Shows High Similarity to SfmO2 and SacJ.

EtuO may catalyze modification of the tetrahydroisoquinoline to produce the hydroxylated species based on previous work involving sacJ gene disruption (FIG. 3 17-18). In vitro biochemical characterization of this enzyme will require synthesis of an advanced intermediate to determine its precise activity.

Regulatory Enzymes.

EtuR1 has significant similarity (59%) to S29x, a protein previously shown to have a role in host-symbiont interactions between Amoeba proteus and the symbiotic Gram-negative X-bacteria. This fascinating protein is excreted from the bacterium, and localized to the A. proteus nucleus. The role of S29x in host-symbiont interactions is unclear with no other homologs characterized. The presence of a homolog to a characterized symbiont-derived gene in the Etu cluster suggests that regulated host-symbiont interactions may be involved in ET-743 biosynthesis. BLASTx analysis of EtuR2 shows (34/58%) identity/similarity to a MerR family transcriptional regulator. This class of regulators has been found in diverse classes of bacteria and responds to toxic effectors including heavy metals and antibiotics45. EtuR3 resembles the TraR/DksA transcriptional regulator that functions as a DNAK suppressor protein.

EtuT Appears to be a Drug Transporter Protein.

Members of this superfamily are commonly represented in natural product biosynthetic pathways and could serve as part of a resistance/export mechanism for ET-743.

Synthesis of ET743

ET743 is derived from an unusual amino acid precursor 3-hydroxy-5-methyl-O-methyl-tyrosine (3h5mOmY). Previously, gene cassettes have been described and characterized for the generation of this key and unusual intermediate. As shown in FIG. 3, the pathway provided herein includes 3-hydroxylation of tyrosine, 4-O methylation of tyrosine, followed by 5-methylation of tyrosine.

The overall scheme for ET743 biosynthesis is also depicted in FIG. 3. Using cell-free extracts, Kerr and Miranda identified tyrosine and cysteine as biosynthetic building blocks, but incorrect coupling [Kerr et al., *Journal of Natural Products* 58: 1618 (1995)]. Tunicate was harvested, lysed, and an active-cell free extract was fed radioactive tyrosine and cysteine. Based on this experiment, it was established that both tyrosine and cysteine are utilized in ET743 biosynthesis, although their biosynthetic scheme is incorrect given subsequent development of the model for NRPS biosynthesis.

Without being bound by a specific mechanism, ET743 synthesis begins with assembly of the key subunit 3H-4O-Me-5Me-Tyr (7) (FIG. 3). This non-proteinogenic amino acid is formed by 3-hydroxylation of (4), 4-O methylation of (5), and 5-methylation (6) catalyzed by EtuH, EtuM2, and EtuM141, respectively. Next, the fatty acid CoA ligase of EtuA3 loads a fatty acid (8) onto the T domain. This fatty acid is condensed with cysteine that is activated and loaded by the C-A-T module of EtuA3 (9). Cysteine condenses with a T-loaded glycolate on EtuA1 to form the acylated-depsipeptide (10). Based on Koketsu's model, (10) is reductively released by the EtuA2 RE-domain as an aldehydo-depsipeptide (11) from the EtuA1 T-domain. Such a "reach-back" model is not unprecedented in natural product biosynthesis48. EtuA2 loaded with 3H-4O-Me-5Me-Tyr (7) is then condensed with (11) to form the cyclic aldehydo-tridepsipeptide (12) through the presumed Pictet-Spenglerase activity of the EtuA2 C domain. Intermediate (12) is released from the EtuA2 T by the RE-domain activity as an aldehyde (13). Based on Koketsu's model it is proposed that EtuA2 catalyzes a second Pictet-Spengler reaction between another unit of 3H-4O-Me-5Me-Tyr (7) and (13). The protein-bound tetradepsipeptide (14) is then reductively released to form aldehyde (15) that may undergo a further enzyme-catalyzed Pictet-Spengler reaction to form the fatty-acid bound carbinolamine pre-ET-743 (16). The penicillin acylase EtuF3 (16) is then proposed to cleave the fatty acid unit, which may serve to sequester substrate in the EtuA2 active site during repeated loading/release, forming pre-ET-743 (17). Proposed intermediates ET-583 (18), ET-597 (19), ET-596 (20), and ET-594 (21) have all been isolated, characterized30, and all except ET-596 (20) have been confirmed by our secondary metabolite analysis (FIG. S3). It is further proposed that pre-ET-743 (17) is hydroxylated by EtuO, acetylation and formation of the thioether ring are both catalyzed by unknown enzymes/mechanisms and intermediates to form ET-583 (18). An unidentified N-methyltransferase acts on ET-583 (18) to generate ET-597 (19). In accordance with Sakai, it is also proposed that a transamination reaction proceeds on (19) to produce ET-596 (20). Another unknown protein catalyzes formation of a methylene dioxybridge in the A ring to generate ET-594 (21). Since compounds (18-21) are isolable, and tryptophan analogs of ET-743 have also been observed, it is reasonable to propose that the final subunit to complete biosynthesis of the drug is added at a late stage, perhaps by formation of an imine to the β-carbonyl and the new tyrosine analog. In both ET-743 total synthesis and semi-synthesis schemes, the α-ketone (21) is transformed to the final tetrahydroisoquinoline ring system by addition of 4-O-methyl-tyrosine under mild conditions 8,10. Further processing steps are hypothetical, with neither enzyme nor intermediate identified. It is proposed that another tyrosine analog, 4-O-methyl-tyrosine (22) is condensed with ET-594 (21). The proposed imine intermediate (24) may then undergo another Pictet-Spengler-type reaction to form the final ring system (25). It is unknown if this unusual cyclization reaction and reduction is catalyzed by EtuA2 or an additional enzyme. The mechanism by which the proposed thioester of ET-743 is released from the proposed enzyme as ET-743 (1) remains to be established. Full validation of this proposed pathway will require synthesis of the predicted enzyme substrates, and direct biochemical analysis.

EXAMPLES

Example 1

Collection of *Ecteinascidia turbinata*

*Ecteinascidia turbinata* is widely distributed in the Caribbean and Mediterranean in warm waters at relatively shallow depths often near mangroves. *E. turbinata* and their larvae are unpalatable to fish, with substance removable by dialysis which cannot be denatured, suggesting that a small molecule such as ET743 is serving as a serve as a chemical defense [Young et al., *Marine Biology* 96: 539 (1987)]. Interestingly, the larvae of *Bugula neritina*, the bryostatin source, are similarly unpalatable due to production of bryostatin by bacteria that are specifically located. *E. turbinata* samples were collected near the Mote Marine Laboratory Tropical Research Laboratory on Summerland Key in Florida. Tunicate samples were washed, and then frozen on dry ice for shipping. Alternatively, DNA was prepared on-site according to a CTAB method [Piel et al., *Proceedings of the National Academy of Sciences* 101: 16222-16227 (2004)]. To verify ET743 production, which would serve as a marker for the presence or absence of the hypothesized symbiont, 250 grams of tunicate were extracted with organic solvent as previously described [Rinehart et al., *The Journal of Organic Chemistry* 55: 4512-4515 (1990)]. The organic extract was then analyzed by LCMS and FTICR-MS/MS (FIG. 4). A strongly absorbing peak at 240 nm and 287 nm was observed to have a $mH^+$ of 744.3 Da. This same parent ion was subjected to MS/MS with CID and IRMPD in an FTICR-MS with a fragmentation pattern matching that previously reported for ET743 with mass errors of <20 ppm [Rinehart et al., *The Journal of Organic Chemistry* 55: 4512-4515 (1990); Rinehart, *Medicinal Research Reviews* 20: 1 (2000)].

Example 2

High-Throughput Sequencing of *E. turbinata*

The *E. turbinata* samples collected were then prepared for high throughput sequencing and subjected to two rounds of Roche 454 FLX™ Platinum sequencing. Of the more than 90,000 strains identified in the sample, the best candidate for ET743 production was identified. Previously, Moss and coworkers had examined 16S rRNA genes from *E. turbinata* and found that three bacterial species dominated, with one accounting for >50% of clones examined and assigned as a δ-proteobacteria, *Candidatus Endoecteinascidia frumentensis* (AY054370). In-situ hybridization was used to identify specific intracellular localization of the bacteria and it was also identified in the larvae—suggesting that a symbiosis or other close relationship may be occurring [Moss et al., *Marine Biology* 143: 99 (2003)]. *E. turbinata* collected from multiple sites was later shown to contain five persistent strains of bacteria [Perez-Matos et al., *Antonie van Leeuwenhoek* 92(2): 155 (2007)]. Again, *C. Endoecteinascidia frumentensis* was found across all sites, and was the only identified bacteria present in both studies. An 11.2 kb contig was assembled from DNA sequencing reads and was found to match the *C. Endoecteinascidia frumentensis* 16S rRNA gene with 99% identity. The presence of this sequence in the pool is strong evidence that the ET743 biosynthetic pathway should be present within the metagenomic DNA.

Based on the similar biosynthetic origins between saframycin [Li et al., *Journal of Bacteriology* 190: 251-263 (2008)] (GenBank Accession Number DQ838002), saframycin Mx1 [Pospiech et al., *Microbiology* 141:1793 (1995)] (GenBank Accession Number MXU24657), and safracin [Velasco et al., *Molecular Microbiology* 56: 144 (2005)] (GenBank Accession Number AY061859), the identified biosynthetic genes in these pathways were identified from the total metagenomic DNA which was translated in all six reading frames and blastP was used to search against the identified biosynthetic genes from those pathways. FIG. 5 depicts the 19 kb assembled contig containing the 10 putative ET743 biosynthetic genes, nearest matches, and proposed functions. The contig was extended and confirmed by Sanger sequencing. The left-hand limit of the cluster is contemplated to be identified herein, as in the negative direction a conserved gene DNA polymerase III delta subunit is present as determined by four out of the top five hits from NCBI BLAST. Interestingly, three out of the top five are identified as coming from marine γ-proteobacteria.

Example 3

Secondary Metabolite Identification

Field-collected tunicate samples of *E. turbinata* from the Florida Keys were confirmed to contain ET-743 and related metabolites using high-resolution, high-mass accuracy, liquid chromatography-Fourier transform ion cyclotron resonance mass spectrometry (LC-FTICR-MS). Known biosynthetic precursors were identified from the tunicate by extracted ion chromatograms at ±20 ppm, including the $M+H^+$ and $(M-H2O)+H^+$ for ET-743 (1), ET-597 (19), ET-594 (21) and ET-583 (18). Confirmation by LC-MS/MS was performed on-line with FTICR-MS and an iontrap-mass spectrometer (IT-MS). Since all four compounds identified had previously been characterized by MS/MS, assignment of product ions was straightforward as observed fragmentation was consistent between earlier studies using fast atom bombardment (FAB)-collision induced dissociation (CID) [Sakai et al., J. Am. Chem. Soc. 118: 9017-9023 (1996)], and work by the inventors with electrospray ionization (ESI)-(CID) on FTICR and IT instruments. The presence of both ET-743 and presumed precursors indicated that ET-743 biosynthesis occurred within the field-collected animal, and thus that the producing symbiont was present.

Briefly, tunicate samples were deproteinized with methanol (2:1 ratio, 1 hr at −20° C.), the protein was removed by centrifugation (14,000 RCF×G), and the supernatant was concentrated 5-fold. Fifty microliters of this sample was analyzed on a Luna C18 100 Å 2×250 mm 5 μm column (Phenomenex). The following gradient was generated on an Agilent 1100 HPLC: 0 (98.2), 10 (98.2), 95 (2.98), 100 (2.98) and 105 (98.2). Values are given as Time (% A, % B). Time is given in minutes with the total run time being 120 minutes at a flow rate of 0.2 ml/min. A column heater was operated at 50° C. The flow was diverted for the first 10 minutes of the run. Buffer A consisted of 0.1% formic acid in DDI water and Buffer B consisted of 0.1% FA in acetonitrile.

FTICR MS was performed on an APEX-Q (Apollo II ion source, 7T magnet, Bruker Daltonics). Data were gathered by ESI in positive ion mode (2,400 V, m/z 150-1,000, transient 128K, 1 scan/spectrum) with external ion accumulation (0.33 s), dynamic trapping, and 1 ICR cell fill per spectrum. External calibration utilized HP-mix (Agilent). For FTICR MS/MS experiments auto-MS/MS was selected with Q-isolation (10 m/z, 5 precursor ions, collision energy of −16 to −21 V). A peak list of possible ET-743 related metabolites was used for precursor ion selection. Data were processed in Data Analysis (Bruker Daltonics) and MS/MS spectra were interpreted manually. Metabolite peaks were detected over multiple samples and runs. Iontrap-MS/MS was performed with HPLC conditions as above, except with a Surveyor HPLC (ThermoFisher). An LTQ Deca XP Ion trap MS (ThermoFisher) was employed for data-dependent MS/MS (1 precursor ion scan, 400-1800 m/z, 7 MS/MS events, isolation width 3 m/z, normalized collision energy 35%). Data analysis was performed in Excalibur version 3.0 (Thermo) and MS/MS spectra were interpreted manually.

Example 4

Metagenomic Sequencing and Phylogenetics 454 and 16S rRNA gene library construction and sequencing methods. Metagenomic DNA was extracted from frozen *E. turbinata* samples using a DNeasy Tissue kit (Qiagen). DNA was used to prepare a 16S rRNA gene targeted amplicon library using primers TGCTGCCTCCCGTAGGAGT (SEQ ID NO: 51) and AGAGTTTGATCCTGGCTCAG (SEQ ID NO: 52) and a random shotgun 454 FLX library. Sequencing was performed on a Roche/454 Life Sciences FLX Sequencer. Later, a second shotgun library was prepared using the 454 Titanium upgrade. Tunicate raw sequencing reads from the first FLX run were assembled using the 454 Newbler assembler (v2.0.00.20). The second 454 Titanium sequencing run was assembled together with the first sequencing run data producing a second assembly (Newbler v2.0.01.14).

NRPS module identification. Reads/contigs were filtered by protein homology to the saframycin, saframycin Mx1, and safracin NRPS genes characterized in *S. lavendulae* (DQ838002), *M. xanthus* (U24657), and *P. fluorescens* (AY061859) using BLASTx/tBLASTn searches. Primers were designed from the ends of filtered sequences (VectorNTI 9, Informax) and PCR reactions were designed based on the location of the BLAST hit on the reference sequences. Sequencing of positive reactions with linked sequences was performed with Sequencher 4.9, Gene Codes. Flanking sequence from high interest contigs was obtained by restriction-site PCR (RS-PCR) including two rounds of PCR using a semi-degenerate primer in conjunction with nested primers of known sequence [Ragin et al., Int. J. Cancer 110: 701-709 (2004)].

Analysis of the Metagenomic Population.

Classification of the raw reads and total assembly was performed with MG-RAST [Meyer et al., BMC Bioinform. 9: 386-386 (2008)]. Sequences were classified by protein homology to a manually curated database (the SEED). The 16S rRNA gene amplicon sequencing run was analyzed by assembling the raw reads with an identity threshold of 95%. The assembled contigs were submitted to the Ribosomal Database Project (RDP) for classification [Wang et al., Ap. Environ. Microbiol 73: 5261-5267 (2007)]. Multiple sequence alignment (MSA) for 16S rRNA gene sequences was performed by [DeSantis et al., Ap. Environ. Microbiol 72: 5069-5072 (2006); DeSantis et al., Nuc. Acids Res. 34: W394-399 (2006)]. Default parameters were used except for minimum length (300) and minimum % identity (50%). Formatting was changed to "remove common alignment gap characters" to provide an equal length MSA. The correct tree-building model was selected [Keane et al., BMC Evol. Biol. 6: 29-29 (2006)], and assembled using the maximum likelihood method with the HYK nucleotide substitution matrix and additional parameters selected by Modelgenerator (Phym1 v2.4.4) [Guindon et al., Sys. Biol. 52: 696-704 (2003)]. The cladeorgram was displayed (FigTree v1.3.1) using midpoint rooting and colored with clade annotation. Gene-finding was performed on the NRPS contig, *E. frumentensis* 16S contig (contig00422), and random contigs from the total shotgun assembly (AMIgene with manual curation) [Bocs et al., Nucleic Acids Research 31: 3723-3726 (2003)]. Relative Synonymous Codon Usage (RSCU) analysis and CAI analysis was performed with codonW [Wang et al., Proc. Nat. Acad. Sci. USA 104: 7612-7616 (2007)]. Further phylogenetic classification of the NRPS contig and contig00422 was performed using the Naïve Bayesian Classification Tool using the 3- and 6-mer setting [Hicks et al., ACS Chem. Biol. 1:93-102 (2006)].

Based on identification of ET-743 from field-collected tunicates, total hologenomic DNA from *E. turbinata* samples was prepared. This DNA was used to prepare a 16S rRNA gene amplicon library and a random shotgun fragment library for 454 based FLX pyrosequencing. Raw reads from the first shotgun sequencing run, and an assembly of these data were filtered using relatedness of the translated protein sequences to the saframycin and safracin non-ribosomal peptide synthetases (NRPSs) (MXU24657, DQ838002, AY061859) using BLASTx and tBLASTn. Linkage of these sequences was performed using a combination of traditional PCR and restriction-site PCR (RS-PCR) yielding six contigs of high interest containing NRPS domains for biosynthesis of ET-74331. A second sequencing run combined with the first generated another assembly of 839,923 reads with an average read length of 332 bp, bearing 77,754 total contigs, and 15,097 contigs larger than 500 bp. A 22 kb contig was identified that linked 4/6 of the high interest contigs from the first assembly and extended this putative NRPS-containing contig to >35 kb using RS-PCR. This DNA fragment was PCR amplified and Sanger sequenced for confirmation. Twenty-six ET-743 biosynthetic genes were identified in this contig and annotated with proposed function using BLASTx against the NCBI NR database, Genbank HQ609499). The individual genes appear to be of bacterial origin, suggesting that the cluster is not derived from the tunicate genome. In addition to the 35 kb putative NRPS contig, sequences containing ribosomal RNA (rRNA) fragments were identified. One of these rRNA sequences was located in a large contig (contig00422) that was extended to >26 kb with RS-PCR. Contig00422 (Genbank HQ542106) contains a full 16S rRNA gene, which aligns (>99% identity) to the 16S rRNA gene reported previously for *E. frumentensis* (AY054370) (DQ494516) [Moss et al., Mar. Biol. 143: 99-110 (2003); D'Agostino et al., Int. J. Gynecol. Cancer. 16: 71-76 (2006)].

Taxonomic classification of the raw reads and of the total assembly was performed using the Metagenomic Rapid Annotations with Subsystems pipeline (MG-RAST) [Meyer et al., BMC Bioinform. 9: 386-394 (2008)]. Results from both sets were consistent, with ~40% of the classified sequences being of eukaryotic origin (mainly *Ciona* [sea squirt/tunicate]) and the remaining 60% being largely proteobacterial sequence (>90%) of which there were two major populations: α-proteobacterial (largely *Rhodobacteraceae,* 78-85%) and γ-proteobacterial (10-17%). 16S rRNA gene amplicon sequencing runs identified 30 variants but only three significant ones (>1% of the total reads). The largest population of 16S rRNA gene reads was classified as *Rhodobacteraceae* (~78%), consistent with the classification of shotgun reads by MG-RAST. This 16S rRNA gene variant aligns to contig09113 from the shotgun sequence assembly, found previously in two of the three tunicate sampling sites from the Caribbean (clone 2j, DQ494507) [Parez-Matos et al., Antonie van Leeuwenhoek 92: 155-164 (2007)]. The second most abundant 16S rRNA gene variant is an unclassified γ-proteobacterium (~19%) that aligns to contig00422 and represents *E. frumentensis* in the sample. A third small population of 16S rRNA gene reads was identified as unclassified bacteria and corresponded to one read from the shotgun sequencing runs (also identified previously) [Moss et al., Mar. Biol. 143: 99-110 (2003)]. These three variants account for >97% of the 16S rRNA gene sequencing reads. None of these three strains form a close phylogenetic relationship with *S. lavendulae, M. xanthus*, or *P. fluorescens*, producers of the three tetrahydroisoquinoline antibiotics whose pathways have been previously characterized.

The putative ET-743 35 kb biosynthetic gene cluster was then linked to the *E. frumentensis* 16s contig00422 by evaluating the codon usage bias. Bacteria typically do not employ synonymous codons equally and this can be exploited as a unique marker [Sharp et al., ISME J. 1: 693-702 (2007)]. A Relative Synonymous Codon Usage (RSCU) analysis was performed using the annotated NRPS contig and contig00422 as well as ORFs identified in several contigs chosen at random. The RSCU score is the observed frequency of a codon divided by the frequency expected for equal usage of all synonymous codons, thereby making it a measure of non-randomness [Sharp et al., ISME J. 1: 693-702 (2007)]. RSCU scores for each codon were similar between the genes on the contig bearing the presumed NRPS biosynthetic genes and the *E. frumentensis* 16S rRNA gene-containing contig00422, but varied compared to RSCU scores from genes located in the random contigs from the total assembly. The extremely low GC content of the contig bearing the putative ET-743 NRPS genes (~23%) closely matches the GC content (26%) of the contig bearing the 16S rRNA gene corresponding to *E. frumentensis*, providing another strong marker of genetic linkage. On the other hand, *Rhodobacteraceae* appear to have uniformly high GC content (54%-70%) according to current whole genome sequencing data, indicating that the contig containing NRPS genes is unlikely to be linked to this organism. The only fully sequenced and annotated tunicate genome, *Ciona intestenilis*, is 35% GC. (NZ_AABS00000000) To account for GC bias in codon usage random genes from the low GC bacterium (~29%) *Clostridium botulinum* str. Okra were included. A comparison of the mean RSCU values for each codon revealed that only 12/60 values differed significantly ($p<0.05$) between the putative ET-743 NRPS and contig00422 genes while 18/60 differed between the putative NRPS genes and random genes from *C. botulinum*. The significant differences between *C. botulinum* genes are most evident in the codons encoding isoleucine (AUU, AUC, AUA), lysine (AAA, AAG), aspartic acid (GAU, GAC), glutamic acid (GAA, GAG) and arginine (CGU, CGC, CGA, CGG, AGA, AGG). 49/60 codons differed significantly between the putative NRPS genes and random tunicate metagenome genes. In addition to RSCU analysis the contig containing the 26 predicted ET-743 pathway genes was used in a correspondence analysis using codonW to generate a codon adaptive index (CAI). This index was then used as a reference for comparison with the same genes used in the RSCU analysis. Although all CAI scores differed significantly from the NRPS contig CAI score ($p<0.05$), the *C. botulinum* CAI score and random gene CAI scores differed to a larger degree. The contig bearing the NRPS genes and contig00422 was also analyzed with the Naïve Bayesian Classifier (NBC) tool, a composition-based metagenome fragment classifier that uses N-mer frequency profiles [Yamamoto et al., J. Bacteriol. 190: 1308-1316 (2008)]. NBC analysis based on 3- and 6-mer profiles resulted in high confidence classification of both contigs as γ-proteobacteria/Enterobacteriaceae. This same *E. frumentensis* 16S rRNA gene sequence has now been linked to *E. turbinata* collections from the Mediterranean, Caribbean, and Florida Keys. Taken together, the sequence contig bearing NRPS module genes are derived from the same organism as contig00422 (*E. frumentensis*).

Biochemical Confirmation of a Key Enzymatic Activity.

Briefly, the biochemical reaction of compound (26) to (27) was performed as described by Koketsu [Koketsu et al., Nat. Chem. Biol 6: 408-411]. Reactions took place in reaction buffer with either no enzyme, EtuA RE-domain, or SfmC. Cofactors were then added from concentrated stocks. Compound (26) was then added in DMF followed by incubation overnight at room temperature. LC-FTICR MS was then run to monitor the reaction products.

Specifically, the transformation of thioester-bound acylated-depsipeptide (10) to the aldehydo-didepsipeptide (11) is a key enzymatic step thought to be catalyzed by the EtuA2 RE domain. Therefore, the excised EtuA2 RE domain was cloned and overexpressed to test this activity To make the SfmC over-expression construct, the sfmC gene was amplified using genomic DNA from *Streptomyces lavendulae* NRRL 11002 as template and SfmC_F (5'-GCAGAATTC CATATGGTGACCCGGCACGAGCC-3', NdeI site underlined (SEQ ID NO: 53) and SfmC_R (5'-TTTGGATCC AAGCTTTCATCGCTCCTCCTCCAGCGTGC-3', HindIII site underlined SEQ ID NO: 54) as primers. The PCR product was digested with NdeI and HindIII and cloned to the same sites of pET-28a to generate pET28a-sfmC. PfuTurbo® DNA Polymerase (Stratagene) was used in sfmC cloning.

To make the over-expression construct for the RE domain of EtuA3, the RE coding sequence (1,251 bp) was amplified via PCR using the metagenomic DNA mixture as template and EtA3RE_F (5'-GCAGAATTC CATATGACCTTGCAAAAAGAAGGAATTG-3', NdeI site underlined (SEQ ID NO: 55) and EtA3RE_R (5'-CGCG-GATC CTCGAGTTATATTTTTTCGGATGAGGAAAG-3', XhoI site underlined (SEQ ID NO: 56) as primers, digested with NdeI and XhoI, and further cloned to the same sites on pET-28a to generate pET28a-RE. KOD DNA Polymerase (Novagen) was used in the cloning of the EtuA3 RE domain.

The N-$His_6$-tagged RE domain protein and the N-$His_6$-tagged SfmC protein expression constructs were separately transformed into *E. coli* BL21 (DE3)+pRare. The two strains were grown at 37° C. in 0.5 L TB medium to an $OD_{600}$ of approximately 0.8 in 2 L flasks. The cultures were cooled to 18° C., and isopropyl β-D-thiogalactopyranoside was added to a final concentration of 0.2 mM and grown 12-16 hours with shaking. The cells were harvested by centrifugation and frozen at −80° C. Cell pellets were thawed to 4° C. and resuspended in 5× volume of lysis buffer (20 mM HEPES, pH 7.8, 300 mM NaCl, 20 mM imidazole, 1 mM Tris(2-carboxyethyl) phosphine (TCEP), approximately 20 mg CelLytic Express (Sigma-Aldrich)) before lysis via sonication. Centrifugation at 40,000×g for 30 min provided clear lysates. Proteins were purified using affinity chromatography with Nickel-NTA resin (Qiagen). Briefly, after filtration of the supernatant through 0.45 μm membrane, the solution was loaded onto a 1 mL gravity flow column. The column was washed with 10 column volumes of wash buffer (20 mM HEPES, pH 7.8, 300 mM NaCl, 50 mM imidazole, 1.0 mM TCEP, 10% glycerol) and eluted with 20 mM HEPES, pH 7.8, 300 mM NaCl, 400 mM imidazole, 1.0 mM TCEP, 10% glycerol. Fractions were pooled, concentrated, and loaded onto a PD10-desalting column (GE Healthcare Life Sciences) equilibrated with storage buffer (20 mM HEPES, pH 7.4, 150 mM NaCl, 1.0 mM TCEP, 20% glycerol). Fractions were combined, concentrated, frozen, and stored at −80° C. Protein concentrations were calculated using A280 and predicted protein extinction coefficients. Proteins were approximately 80% and 95% pure by SDS-PAGE with yields of 1 mg/L for EtuA2 RE and 3 mg/L for SfmC.

Koketsu and coworkers had shown the same activity for the matching saframycin substrate analogs (25→26) with the SfmC A-T-RE-tridomain [Koketsu et al., Nat. Chem. Biol 6: 408-411]. Therefore, the known saframycin substrate analog (25) was synthesized and transformed to the previously characterized saframycin aldehydo-dipeptide (26) by the EtuA2 RE domain. As a positive control, substrate (25) was converted with high efficiency to (26) by purified apo-SfmC (C-A-T-RE). The differential activity was expected as (25), while clearly an acceptable substrate, is missing the cysteine-derived thiol and has a glycine in place of the glycolic acid compared to the native substrate (10). Experimental data was in agreement with a synthetic authentic standard aldehydo-dipeptide (27). Confirmation of RE enzyme activity links the predicted biochemical scheme to demonstrated function in the ET-743 biosynthetic pathway.

Metaproteomics to Identify ET-743 Biosynthetic Proteins.

Briefly, tunicate protein samples were precipitated with acetone then resolubilized, reduced, alkylated, diluted, and digested with trypsin. The sample was fractionated over 40 minutes into 20 fractions using SCX chromatography. The 20 peptide fractions were analyzed once on an LTQ-Orbitrap XL interfaced with a nanoLC 2D system. Peptides were separated on a capillary column in-house packed with C18 resin after loading on a C18 trap column. LC eluent was introduced into the instrument via a chip-based nanoelectrospray source in positive ion mode. The LTQ-orbitrap was operated in data-dependent mode. The 20 peptide fractions were also analyzed in duplicate on a Solarix 12T hybrid Q-FTICR interfaced with a nanoLC system. Peptides were separated on a capillary column packed in-house with C18 resin after loading on a C18 trap column. The FTICR operated in data-dependent mode. All scans were collected in the profile mode and peak picking was performed from the profile mode spectra. Bioinformatics analysis was performed with the Transproteomic Pipeline and all assigned Etu peptides were validated by comparison with synthetic peptide standards.

Specifically, total tryptic peptides from the field-collected *E. turbinata* sample were fractionated by strong-cation-exchange chromatography, desalted, and then analyzed by reverse phase nano-LC MS/MS. Datasets were collected on LTQ-Orbitrap and 12T Q-FTICR mass spectrometers, with high-resolution/mass-accuracy MS 1 spectra (and MS2 for FTICR only). Data were processed in Trans Proteomic Pipeline49 with four distinct search engines (X!tandem, OMSSA, Inspect, and Spectrast) and the peptide and protein prophet probability models with false discovery rates at the protein level of 0.6-0.9%. The database searched consisted of a six-frame translation of the total metagenome assembly filtered to contain all possible polypeptides >60 amino acids in length (SI). Sequence length-based cutoffs were utilized rather than ORF prediction due to the short length of many metagenomic contigs derived from the 454 metagenomic sequencing. Filtering resulted in a six-fold reduction in total sequence length versus the unfiltered six-frame translation. A 60 amino acid cut-off represents a 0.2% chance of any random sequence producing a translation without a stop codon appearing. Based upon 23S/16S analysis the closest fully sequenced organisms to the four principle constituents of the assemblage were included to assign homologous proteins derived from genes that may have been incompletely sequenced in the metagenomic analysis (tunicate: *Ciona intestinalis* NZ_AABS00000000, α-proteobacteria: *Ruegeria pomeroyi* DSS-3 NC 003911, γ-proteobacteria: *Coxiella burnetii* RSA 331 NC_010115, unknown bacteria: *Mycoplasma mycoides* subsp. *mycoides* SC str. PG1 NC_005364). Reversed sequences for all proteins were included as decoys in the search database.

A total of 289 proteins were identified at a probability >95% from interprophet pooled analysis of all four search engines prior to Protein Prophet analysis. Three of the proteins identified were derived from the Etu pathway with two identified by Orbitrap and one by FTICR and Orbitrap MS. The penicillin acylase EtuF3 was identified with two unique peptides, 3+ TIQHEIELSDIGPIINNLIQEN115NQINKK (N115=deamidated) and 2+ RPIELR, and the protein was identified in 3/4 search engines providing a total protein probability of 99.99%. The bacterial symbiont protein EtuR1 was identified with two unique peptides, 2+ GSNIHYDLENDHNDYEK and 3+ GSNIHYDLENDHNDYEK, identified by 3/4 search engines at the protein level with a combined protein probability of 100.00%. The EtuM1 SAM dependent methyltransferase was identified by one unique peptide, 2+ LLDVGGGTAINAIALAK and 2/4 search engines at the protein level with a probability of 99.16%. All identified Etu peptides were validated by comparison with synthetic peptide standards by LC elution time (±2 minutes on the same nano-LC system), and MS/MS fragmentation spectra. Detailed spectral information was obtained. These three biosynthetic proteins identified with high probabilities and confidence levels by multiple search algorithms and comparison with authentic standards strongly suggests that ET-743 biosynthetic genes are expressed in the tunicate microbial symbiont assemblage.

The overall constitution of the collected assemblage proteome was also characterized using a BlastP analysis of metagenomic contigs, restricted to tunicate and bacterial sequences. The 289 proteins identified represent the minimum number of distinct DNA sequences that fully represent the assigned dataset, however as many as 391 distinct DNA sequences can be assigned to this same set of peptides (e.g., multiple copy genes, homologous genes, shared peptides). Of the maximum possible 391 proteins 283 were tunicate derived, 91 were bacterial derived, and 17 produced no significant similarity. Of the 91 bacterial proteins identified 71 appeared to be of proteobacterial origin and 20 could not be assigned at the family level. Of the 71 proteobacterial proteins identified 24 were α-proteobacterial, 26 were γ-proteobacterial origin, and 21 could not be assigned beyond proteobacterial. Apparent distribution of predominant species (tunicate, α-proteobacterial, γ-proteobacterial) roughly correlates with metagenomics/16S rRNA genes with higher amounts of tunicate proteins observed than would be expected from a direct correlation of DNA and protein levels. More γ-proteobacterial proteins were observed compared to α-proteobacterial assuming DNA is proportional to expression level.

The inability to culture the vast majority of bacterial and fungal symbionts (outside of their natural host or environmental niche) that produce secondary metabolites have limited access to a huge genetic diversity relating to untapped chemical resources for therapeutic and other industrial applications. This includes complex marine (e.g., sponge, tunicates, dinoflagellates) and terrestrial (e.g., plant-microbe, biofilm, insect-gut, human-gut) microbial consortia where the presence of large populations of diverse microorganisms and their corresponding genomes that bear natural product gene clusters remain unexplored. This new source of metabolic and chemical diversity will lead to important new basic knowledge, and also contribute to ongoing drug discovery efforts against many disease indications.

In these studies, several steps were taken to obtain evidence for identification of the ET-743 biosynthetic pathway and the corresponding producing microbial symbiont. First, the presence of the ET-743 natural product and intermediates were used as markers for the producing bacterium in the tunicate/microbial consortium. Second, codon usage similarity between the biosynthetic gene cluster and a contig containing a 16S rRNA gene sequence support *E. frumentensis* as the bacterial producer of ET-743. Direct functional analysis of a key biosynthetic enzyme confirmed its predicted catalytic assignment in the pathway. Finally, symbiont-derived expression of three ET-743 biosynthetic enzymes was confirmed by metaproteomic and bioinformatic analysis, enabling the direct correlation between natural product, the Etu gene cluster, and predicted biosynthetic proteins. This tiered strategy provides a general approach for future efforts to characterize orphan and target natural product biosynthetic systems from complex marine and terrestrial microbial assemblages including animal-microbe symbiont consortia, and dinoflagellates.

While the present invention has been described in terms of various embodiments and examples, it is understood that variations and improvements will occur to those skilled in the art. Therefore, only such limitations as appear in the claims should be placed on the invention.

What is claimed is:

1. A host cell transformed with a polynucleotide encoding (i) the EtuA1 polypeptide (SEQ ID NO: 1) of a nonribosomal peptide synthetase or a protein 95% identical to SEQ ID NO: 1 having EtuA1 activity, and (ii) the EtuA2 polypeptide (SEQ ID NO: 2) of a nonribosomal peptide synthetase or a protein 95% identical to SEQ ID NO: 2 having EtuA2 activity.

2. The host cell of claim 1 further transformed with a polynucleotide encoding the EtuF3 polypeptide (SEQ ID NO: 9) of a nonribosomal peptide synthetase or a protein 95% identical to SEQ ID NO: 9 having EtuF3 activity.

3. The host cell of claim 2 further transformed with a polynucleotide encoding the EtuO polypeptide (SEQ ID NO: 16) of a nonribosomal peptide synthetase or a protein 95% identical to SEQ ID NO: 16 having EtuO activity.

4. The host cell of claim 3 further transformed with a polynucleotide encoding the EtuA3 polypeptide (SEQ ID NO: 3) of a nonribosomal peptide synthetase or a protein 95% identical to SEQ ID NO: 3 having EtuA3 activity.

5. The host cell of claim 4 further transformed with a polynucleotide encoding (i) the EtuH polypeptide (SEQ ID NO: 10) of a nonribosomal peptide synthetase or a protein 95% identical to SEQ ID NO: 10 having EtuH activity (ii) the EtuM2 polypeptide (SEQ ID NO: 12) of a nonribosomal peptide synthetase or a protein 95% identical to SEQ ID NO: 12 having EtuM2 activity (iii) the EtuM1 polypeptide (SEQ ID NO: 11) of a nonribosomal peptide synthetase or a protein 95% identical to SEQ ID NO: 11 having EtuM1 activity.

6. The host cell of claim 1 further transformed with a polynucleotide encoding EtuA3 (SEQ ID NO: 3) or a protein 95% identical to SEQ ID NO: 3 having EtuA3 activity.

7. The host cell of claim 6 further transformed with a polynucleotide encoding EtuF3 (SEQ ID NO: 9) or a protein 95% identical to SEQ ID NO: 9 having EtuF3 activity.

8. The host cell of claim 7 further transformed with a polynucleotide encoding EtuO (SEQ ID NO: 16) or a protein 95% identical to SEQ ID NO: 16 having EtuO activity.

9. The host cell of claim 8 further transformed with a polynucleotide encoding EtuH (SEQ ID NO: 10) or a protein 95% identical to SEQ ID NO: 10 having EtuH activity (ii) EtuM2 (SEQ ID NO: 12) or a protein 95% identical to SEQ ID NO: 12 having EtuM2 activity (iii) EtuM1 (SEQ ID NO: 11) or a protein 95% identical to SEQ ID NO: 11 having EtuM1 activity.

10. A host cell transformed with a polynucleotide encoding EtuO (SEQ ID NO: 16) or a protein 95% identical to SEQ ID NO: 16 having EtuO activity.

11. The host cell of claim 10 further transformed with a polynucleotide encoding (i) EtuF3 (SEQ ID NO: 9) or a protein 95% identical to SEQ ID NO: 9, having EtuF3 activity (ii) EtuA1 (SEQ ID NO: 1) or a protein 95% identical to SEQ ID NO: 1, having EtuA1 activity (iii) the EtuA2 polypeptide (SEQ ID NO: 2) of a nonribosomal peptide synthetase or a protein 95% identical to SEQ ID NO: 2, having EtuA2 activity.

12. The host cell of claim 11 further transformed with a polynucleotide encoding EtuA3 (SEQ ID NO: 3) or a protein 95% identical to SEQ ID NO: 3 having EtuA3 activity.

13. The host cell of claim 12 further transformed with a polynucleotide encoding EtuH (SEQ ID NO: 10) or a protein 95% identical to SEQ ID NO: 10 having EtuH activity (ii) EtuM2 (SEQ ID NO: 12) or a protein 95% identical to SEQ ID NO: 12 having EtuM2 activity (iii) EtuM1 (SEQ ID NO: 11) or a protein 95% identical to SEQ ID NO: 11 having EtuM1 activity.

14. The host cell of claim 5 further transformed with a polynucleotide encoding a protein selected from the group consisting of:

a. the EtuD1 polypeptide (SEQ ID NO: 4) of a nonribosomal peptide synthetase or a protein 95% identical to SEQ ID NO: 4 having EtuD1 activity, b. the EtuD2 polypeptide (SEQ ID NO: 5) of a nonribosomal peptide synthetase or a protein 95% identical to SEQ ID NO: 5 having EtuD2 activity, c. the EtuD3 polypeptide (SEQ ID NO: 6) of a nonribosomal peptide synthetase or a protein 95% identical to SEQ ID NO: 6 having EtuD3 activity, d. the EtuF1 polypeptide (SEQ ID NO: 7) of a nonribosomal peptide synthetase or a protein 95% identical to SEQ ID NO: 7 having EtuF1 activity, e. the EtuF2 polypeptide (SEQ ID NO: 8) of a nonribosomal peptide synthetase or a protein 95% identical to SEQ ID NO: 8 having EtuF2 activity, f. the EtuN1 polypeptide (SEQ ID NO: 13) of a nonribosomal peptide synthetase or a protein 95% identical to SEQ ID NO: 13 having EtuN1 activity, g. the EtuN2 polypeptide (SEQ ID NO: 14) of a nonribosomal peptide synthetase or a protein 95% identical to SEQ ID NO: 14 having EtuN2 activity, h. the EtuN3 polypeptide (SEQ ID NO: 15) of a nonribosomal peptide synthetase or a protein 95% identical to SEQ ID NO: 15 having EtuN3 activity, i. the EtuP1 polypeptide (SEQ ID NO: 17) of a nonribosomal peptide synthetase or a protein 95% identical to SEQ ID NO: 17 having EtuP1 activity, j. the EtuP2 polypeptide (SEQ ID NO: 18) of a nonribosomal peptide synthetase or a protein 95% identical to SEQ ID NO: 18 having EtuP2 activity, k. the EtuR1 polypeptide (SEQ ID NO: 19) of a nonribosomal peptide synthetase or a protein 95% identical to SEQ ID NO: 19 having EtuR1 activity, l. the EtuR2 polypeptide (SEQ ID NO: 20) of a nonribosomal peptide synthetase or a protein 95% identical to SEQ ID NO: 20 having EtuR2 activity, m. the EtuR3 polypeptide (SEQ ID NO: 21) of a nonribosomal peptide synthetase or a protein 95% identical to SEQ ID NO: 21 having EtuR3 activity, n. the EtuT polypeptide (SEQ ID NO: 22) of a nonribosomal peptide synthetase or a protein 95% identical to SEQ ID NO: 22 having EtuT activity, o. the EtuU1 polypeptide (SEQ ID NO: 23) of a nonribosomal peptide synthetase or a protein 95% identical to SEQ ID NO: 23 having EtuU1 activity, p. the EtuU2 polypeptide (SEQ ID NO: 24) of a nonribosomal peptide synthetase or a protein 95% identical to SEQ ID NO: 24 having EtuU2 activity, and q. the EtuU3 polypeptide (SEQ ID NO: 25) of a nonribosomal peptide synthetase or a protein 95% identical to SEQ ID NO: 25 having EtuU3 activity.

15. The host cell of claim 14 transformed with 2, 3, 4, 5, 6, 7, 8, 9, 10, 11, 12, 13, 14, 15, 16 or 17 polynucleotides individually encoding a polypeptide selected from the group consisting of:

a. the EtuD1 polypeptide (SEQ ID NO: 4) of a nonribosomal peptide synthetase or a protein 95% identical to SEQ ID NO: 4 having EtuD1 activity, b. the EtuD2 polypeptide (SEQ ID NO: 5) of a nonribosomal peptide synthetase or a protein 95% identical to SEQ ID NO: 5 having EtuD2 activity, c. the EtuD3 polypeptide (SEQ ID NO: 6) of a nonribosomal peptide synthetase or a protein 95% identical to SEQ ID NO: 6 having EtuD3 activity, d. the EtuF1 polypeptide (SEQ ID NO: 7) of a nonribosomal peptide synthetase or a protein 95% identical to SEQ ID NO: 7 having EtuF1 activity, e. the EtuF2 polypeptide (SEQ ID NO: 8) of a nonribosomal peptide synthetase or a protein 95% identical to SEQ ID NO: 8 having EtuF2 activity, f. the EtuN1 polypeptide (SEQ ID NO: 13) of a nonribosomal peptide synthetase or a protein 95% identical to SEQ ID NO: 13 having EtuN1 activity, g. the EtuN2 polypeptide (SEQ ID NO: 14) of a nonribosomal peptide synthetase or a protein 95% identical to SEQ ID NO: 14 having EtuN2 activity, h. the EtuN3 polypeptide (SEQ ID NO: 15) of a nonribosomal peptide synthetase or a protein 95% identical to SEQ ID NO: 15 having EtuN3 activity, i. the EtuP1 polypeptide (SEQ ID NO: 17) of a nonribosomal peptide synthetase or a protein 95% identical to SEQ ID NO: 17 having EtuP1 activity, j. the EtuP2 polypeptide (SEQ ID NO: 18) of a nonribosomal peptide synthetase or a protein 95% identical to SEQ ID NO: 18 having EtuP2 activity, k. the EtuR1 polypeptide (SEQ ID NO: 19) of a nonribosomal peptide synthetase or a protein 95% identical to SEQ ID NO: 19 having EtuR1 activity, l. the EtuR2 polypeptide (SEQ ID NO: 20) of a nonribosomal peptide synthetase or a protein 95% identical to SEQ ID NO: 20 having EtuR2 activity, m. the EtuR3 polypeptide (SEQ ID NO: 21) of a nonribosomal peptide synthetase or a protein 95% identical to SEQ ID NO: 21 having EtuR3 activity, n. the EtuT polypeptide (SEQ ID NO: 22) of a nonribosomal peptide synthetase or a protein 95% identical to SEQ ID NO: 22 having EtuT activity, o. the EtuU1 polypeptide (SEQ ID NO: 23) of a nonribosomal peptide synthetase or a protein 95% identical to SEQ ID NO: 23 having EtuU1 activity, p. the EtuU2 polypeptide (SEQ ID NO: 24) of a nonribosomal peptide synthetase or a protein 95% identical to SEQ ID NO: 24 having EtuU2 activity, and q. the EtuU3 polypeptide (SEQ ID NO: 25) of a nonribosomal peptide synthetase or a protein 95% identical to SEQ ID NO: 25 having EtuU3 activity.

16. A method for producing ET-743 or a metabolic intermediate for producing ET-743 comprising the step of growing the host cell of claim 1 under conditions to express the protein encoded by the transformed polynucleotide and producing ET-743 or the metabolic intermediate for producing ET-743.

17. An isolated protein comprising an amino acid sequence that is selected from the group consisting of the sequence set out in:

(i) SEQ ID NO: 1 or a protein 95% identical to SEQ ID NO: 1 having EtuA1 activity; and (ii) SEQ ID NO: 2 or a protein 95% identical to SEQ ID NO: 2 having EtuA2 activity.

18. An expression vector comprising a polynucleotide encoding the protein of claim 17.

* * * * *

UNITED STATES PATENT AND TRADEMARK OFFICE
CERTIFICATE OF CORRECTION

PATENT NO. : 8,815,562 B2
APPLICATION NO. : 13/640815
DATED : August 26, 2014
INVENTOR(S) : David H. Sherman et al.

It is certified that error appears in the above-identified patent and that said Letters Patent is hereby corrected as shown below:

On the Title Page:
At item (73), line 1, "Regenys" should be -- Regents --.

Signed and Sealed this
Twenty-seventh Day of October, 2015

Michelle K. Lee
*Director of the United States Patent and Trademark Office*